United States Patent [19]

Shapiro

[11] Patent Number: 5,668,117
[45] Date of Patent: Sep. 16, 1997

[54] METHODS OF TREATING NEUROLOGICAL DISEASES AND ETIOLOGICALLY RELATED SYMPTOMOLOGY USING CARBONYL TRAPPING AGENTS IN COMBINATION WITH PREVIOUSLY KNOWN MEDICAMENTS

[76] Inventor: Howard K. Shapiro, 214 Price Ave. F32, Narberth, Pa. 19072

[21] Appl. No.: 62,201

[22] Filed: Jun. 29, 1993

Related U.S. Application Data

[63] Continuation-in-part of Ser. No. 26,617, Feb. 23, 1993, abandoned, which is a continuation of Ser. No. 660,561, Feb. 22, 1991, abandoned.

[51] Int. Cl.$^6$ ............ A01N 43/04; A01N 61/00; C07H 1/00; C08B 37/08
[52] U.S. Cl. .......... 514/55; 514/54; 514/23; 514/1; 514/811; 514/866; 514/878; 514/879; 514/903; 514/912; 436/518; 436/74; 536/1.11; 536/20
[58] Field of Search .............. 514/55, 54, 23, 514/1, 811, 866, 878, 879, 903, 912; 435/6, 7.9; 436/518, 74, 87; 536/1.11, 20

[56] References Cited

U.S. PATENT DOCUMENTS

| | | | |
|---|---|---|---|
| 4,665,069 | 5/1987 | Rosenberg | 514/817 |
| 4,673,669 | 6/1987 | Yoshikumi et al. | 514/42 |
| 4,757,054 | 7/1988 | Yoshikumi et al. | 514/42 |
| 4,771,075 | 9/1988 | Cavazza | 514/556 |
| 4,801,581 | 1/1989 | Yoshikumi et al. | 514/42 |
| 4,874,750 | 10/1989 | Yoshikumi et al. | 514/42 |
| 4,956,391 | 9/1990 | Sapse | 514/810 |
| 4,957,906 | 9/1990 | Yoshikumi et al. | 514/25 |
| 4,983,586 | 1/1991 | Bodor | 514/58 |
| 5,015,570 | 5/1991 | Scangos et al. | 435/6 |
| 5,037,851 | 8/1991 | Cavazza | 514/912 |
| 5,252,489 | 10/1993 | Macri | 436/87 |
| 5,297,562 | 3/1994 | Potter | 128/898 |
| 5,324,667 | 6/1994 | Macri | 436/87 |
| 5,324,668 | 6/1994 | Macri | 436/87 |

*Primary Examiner*—John Kight
*Assistant Examiner*—Louise Leary
*Attorney, Agent, or Firm*—D. J. Perrella

[57] ABSTRACT

Therapeutic compositions comprising an effective amount of at least one carbonyl trapping agent alone or in combination with a therapeutically effective of a co-agent or medicament are disclosed. The compositions are used to treat a mammal suffering from a neurological disease characterized by covalent bond crosslinking between the nerve cells, other cellular structures and their intracellular and extracellular components, with disease induced carbonyl-containing aliphatic or aromatic hydrocarbons present in mammals.

29 Claims, No Drawings

METHODS OF TREATING NEUROLOGICAL DISEASES AND ETIOLOGICALLY RELATED SYMPTOMOLOGY USING CARBONYL TRAPPING AGENTS IN COMBINATION WITH PREVIOUSLY KNOWN MEDICAMENTS

RELATED PATENT APPLICATION

This invention is a continuation in part of U.S. patent application Ser. No. 08/026,617, filed on Feb. 23, 1993, now abandoned, entitled "Method of Treating Neurological Diseases and Etiologically Related Symptomology Using Carbonyl Trapping Agents," which in turn is a continuation of U.S. patent application Ser. No. 07/660,561, filed on Feb. 22, 1991 entitled "Method of Treating Neurological Diseases and Etiologically Related Symptomology Using Carbonyl Trapping Agents," now abandoned, the entire disclosures of which are incorporated by reference herein.

BACKGROUND OF THE INVENTION

1. Field of the Invention

This invention relates to the clinical treatment of neurodegenerative diseases, including hereditary motor and sensory neuropathies (HMSN, also known as Charcot-Marie-Tooth disease), diabetic polyneuropathy, Alzheimer's presenile and senile dementia, Down's syndrome, Parkinson's disease, olivopontocerebellar atrophy, Huntington's disease, amyotrophic lateral sclerosis, age-onset neurological deterioration, alcoholic polyneuropathy, tinnitus, multiple sclerosis, and pathophysiologically symptomology.

2. Description of Prior Art

The logic and potential value, even synergistic value, of using two or more therapeutic agents in combination has been recognized previously (Ghose and coworkers, 1983; Goldstein and coworkers, 1990, pg. 102; Rinne, 1991). For example, in a study on two-drug combinations of memory enhancing agents Flood and coworkers (1988) noted that:

> The potential for clinically desirable drug interactions has been emphasized for drugs in general (1) and for memory enhancing drugs in particular (2,3). For example, individual cholinergic drugs which improve memory retention test scores (4,5,6) do so in two-drug combinations at substantially lower doses than would be predicted if the two drugs acted additively (7,8,9).
> 
> In prior studies of the effect of two-drug combinations on memory processing (8,9), we determined the effect of varying the dose of two drugs while holding the ratio constant. The ratio was based on the optimal memory enhancing doses of each drug administered singly. These studies showed that drugs administered in certain combinations require 67 to 96% less drug to improve retention, than when the same drugs were administered alone. This type of drug interaction was said to yield supra-additivity.

The present disclosure describes the inventive concept of using the therapeutic technology of U.S. patent application Ser. No. 08/026,617, filed Feb. 23, 1993, now abandoned in combination witch pharmaceutical agents previously recognized as having, or possibly having some medicinal value for treatment of the disease entities noted above. No pharmacological treatment of comprehensive effectiveness is currently available for any of the neurological disorders discussed herein. However, a variety of pharmaceutical agents have been described which may offer at least some degree of symptomatic relief from the clinical effects of these diseases.

The 16th edition of the *Merck Manual* (Berkow, 1992, pp. 1497–1499) has defined symptomatic clinical treatment of Parkinson's disease to consist of: (a) oral co-administration of levodopa, the metabolic precursor of dopamine, and carbidopa, a peripheral decarboxylase inhibitor [in compositions such as Sinemet CR]; (b) co-agent use of amantadine HCl [Symmetrel; 1-amino-adamantane, a rye ergot alkaloid and neuronal transmission enhancer]; (c) co-agent use of ergot alkaloids such as bromocriptine mesylate [Parlodel, which has a dopamine agonist activity for $D_2$ receptors and antagonist activity at $D_1$ receptors] and pergolide mesylate [Permax, a dopamine-receptor agonist active at both $D_1$ and $D_2$ receptor subtypes (Robin, 1991)]; (d) selegiline HCl [Eldepryl, a selective inhibitor of monoamine oxidase B which prolongs the action of dopamine (Rinne, 1991)]; (e) co-agent use of anticholinergic medications such as benztropine mesylate [Cogentin], trihexylphenidyl [Artane], procyclidine [Kemadrin], biperiden and ethopropazine [Paridol]; (f) co-agent use of antihistamines such as diphenhydramine [Benadryl] and orphenadrine; (g) co-agent use of tricyclic antidepressants such as amitriptyline, imipramine, nortriptyline and doxepin; and (h) co-agent use of propranolol.

Other well established or experimental therapeutic approaches for clinical treatment of Parkinson's disease, which may or may not be used in conjunction with L-dopa, have been publicly disclosed. These include possible use of (a) selegiline in combination with tocopherol (Greenamyre and O'Brien, 1991); (b) D-cycloserine with or without a cholinesterase inhibitor co-agent (Francis and coworkers, 1991); (c) other dopamine receptor agonists such as (+)-4-propyl-9-hydroxynaphthoxazine (Martin and coworkers, 1984), apomorphine and ciladopa (Koller and coworkers, 1986; Goldstein and coworkers, 1990); (d) neurotransmission enhancer drugs such as lisuride, a rye ergot alkaloid (Rinne, 1989; Rinne, 1991); (e) known antioxidants such as ascorbic acid, alpha-tocopherol, beta-carotene (Mathews-Roth, 1987), N-acetylcysteine (Smilkstein and coworkers, 1988), penicillamine or cysteamine (Harris, 1982), as increased levels of lipid peroxidation are apparent in parkinsonian tissue (Ceballos and coworkers, 1990; Fahn, 1989); (f) other peripheral decarboxylase inhibitors such as benserazide (Madopar HBS) (Pinder and coworkers, 1978; Pletscher, 1990); and (g) N-methyl-D-asparate (NMDA) glutamate receptor antagonists such as dizocilpine (Clineschmidt and coworkers, 1982; Woodruff and coworkers, 1987) and milacemide (Youdim, 1988; Ferris, 1990) or use of the possible antagonist 1-amino-3,5-dimethyl adamantane (Memantine) (Fischer and coworkers, 1977; Schmidt and coworkers, 1990; Greenamyre and O'Brien, 1991); (h) tacrine (Cognex, an experimental agent of Warner-Lambert Co.) and a hydroxy derivative thereof, (±)-9-amino-1,2,3,4-tetrahydroacridin-1-ol (Shutske and coworkers, 1988); and (i) tiapride (Price and coworkers, 1978).

Since activation of NMDA glutamate receptors has also been implicated in the etiologies of Huntington's disease, amyotrophic lateral sclerosis, olivopontocerebellar atrophy and Alzheimer's disease, use of NMDA glutamate receptor antagonists such as those listed above may be of clinical benefit for patients having these diseases (Woodruff and coworkers, 1987; Greenamyre and O'Brien, 1991; Giuffra and coworkers, 1992), as well as for patients suffering from certain neurodegenerative effects of aging (Ferris, 1990). Drugs which may enhance acetylcholine synthesis or release such as phosphatidylcholine, 3,4-diaminopyridine (Ferris, 1990; Harvey and Rowan, 1990) and choline (Sitaram and coworkers, 1978a), as well as the muscarinic cholinergic agonist arecoline (Tariot and coworkers, 1988), have also been proposed for treatment of Huntington's disease.

The use of L-dopa as the primary therapeutic agent for treatment of Parkinson's disease may serve as an example of the limitations of present technology. Citing earlier work, Robin (1991) has noted that " . . . chronic exposure to high dose L-dopa may accelerate the progression of Parkinson's disease." Indeed, clinical benefits to be obtained from L-dopa therapy are predictably limited to perhaps three to five years. After that period, continued use of L-dopa will not provide clinical benefit. This situation exists because L-dopa therapy depends on conversion of this physiological precursor into dopamine within a population of substantia nigra neurons which is selectively deteriorating in this disease. Once the last of these nerve cells is gone, the therapeutic strategy has lost its physiological basis.

However, use of the invention originally disclosed in U.S. patent application Ser. No. 07/660,561, filed Feb. 21, 1991, now abandoned, may serve to sequester and remove aldehyde and ketone products of lipid peroxidation process known to exist in parkinsonian substantia nigra tissue (Fahn, 1989; Youdim, 1990). This may at least partially address the etiological basis of the disease. Use of the invention originally disclosed in U.S. patent application Ser. No. 07/660,561, filed Feb. 21, 1991, now abandoned, in combination with, or originally prior to, present L-dopa therapeutic technology should serve to further advance prior art technology for treatment of Parkinson's disease. Hence, the invention described herein may serve to delay the necessity of initiating L-dopa therapy and, once L-dopa therapy has begun, may serve to permit use of a smaller dosage of the dopamine precursor. This, in turn, may permit a decreased level of metabolic stress on substantia nigra nerve cells.

Similar reasoning applies in the case of prospective treatment of Alzheimer's disease and age-related neuron degeneration. As noted by Ceballos and coworkers (1990):

. . . The development of clinical features in AD [Alzheimer's disease] is linked to the amount of deposition of amyloid in the limbic areas and cerebral cortex. Moreover, amyloid formation may arise as a consequence of membrane damage . . . due to lipid peroxidation . . . About 6% of PHF [paired helical filaments] is composed of the amino-acid, hydroxyproline. This amino-acid is not a constituent of cytoplasmic protein in normal brain and the abundance of hydroxyproline in cytoplasmic PHF involves non-enzymatic hydroxylation of proline residues probably by hydroxyl free radicals. This free radical hypothesis of PHF formation suggests that AD is an acceleration of the normal aging process in affected brain regions.

This background information, in addition to that provided in U.S. patent application Ser. No. 08/026,617, filed Feb. 23, 1993, now abandoned, provides the conceptual basis for use of the invention described herein for treatment of humans suffering from Alzheimer's disease and age-related neuron degeneration. Recently reported strategies for clinical treatment of Alzheimer's disease include possible use of (a) vasodilator or other nootropic direct brain metabolic enhancer drugs such as idebenone (Nagaoka and coworkers, 1984; Shimizu, 1991), propentophylline (Hindmarch and Subhan, 1985; Shimizu, 1991), pentoxifylline (Moos and Hershenson, 1989), citicoline (Moos and Hershenson, 1989), piracetam (Franklin and coworkers, 1986; Becker and Giacobini, 1988), oxiracetam (Spignoli and Pepeu, 1987; Villardita and coworkers, 1987), aniracetam (Cumin and coworkers, 1982; Spignoli and Pepeu, 1987), pramiracetam (Franklin and coworkers, 1986), pyroglutamic acid (Spignoli and coworkers, 1987; Porsolt and coworkers, 1988), tenilsetam (Moos and coworkers, 1988, pg. 362; Pepeu and Spignoli, 1989), rolziracetam (Moos and Hershenson, 1989), etiracetam (Franklin and coworkers, 1986), dupracetam, vinpocetine (Groo and coworkers, 1987; Moos and Hershenson, 1989), ebiratide (Hock and coworkers, 1988), beta-carbolines (Jensen and coworkers, 1987), naloxone (Jensen and coworkers, 1980; Reisberg and coworkers, 1983; Rush, 1986; Henderson and coworkers, 1989; Pepeu and Spignoli, 1990, pgs. 247–248; Cooper, 1991; Whitehouse, 1991), ergoloid mesylates such as Hydergine (Moos and Hershenson, 1989; Cooper, J. K., 1991), bromvincamine (Moos and Hershenson, 1989), cyclandelate (Ananth and coworkers, 1985; Moos and Hershenson, 1989), isoxsuprene (Moos and Hershenson, 1989), nafronyl (Moos and Hershenson, 1989), papaverine (Moos and Hershenson, 1989), suloctidil (Moos and Hershenson, 1989), vinburnine (Moos and Hershenson, 1989), vincamine (Moos and Hershenson, 1989), vindeburnol (Moos and Hershenson, 1989), flunarizine (Holmes and coworkers, 1984; Moos and Hershenson, 1989; Cooper, 1991), nimodipine (Moos and Hershenson, 1989; Cooper, 1991; Whitehouse, 1991), nicergoline (sermion) (Battaglia and coworkers, 1989; Moos and Hershenson, 1989), razobazam (Hock and McGaugh, 1985; Moos and Hershenson, 1989), exifone (Moos and Hershenson, 1989), rolipram (Moos and Hershenson, 1989), sabeluzole (Clincke and coworkers, 1988; Moos and Hershenson, 1989), phosphatidylserine (Delwaide and coworkers, 1986; Zanotti and coworkers, 1986; Amaducci and coworkers, 1987; Moos and Hershenson, 1989; Ferris, 1990; Wurtman and coworkers, 1990, pg. 123; Cooper, 1991)) and ifenprodil (Carron and coworkers, 1971); (b) neurotransmission enhancer drugs (Shimizu, 1991) such as amantadine, calcium hopantenate (Umeno and coworkers, 1981), lisuride, bifemelane (Kikumoto and coworkers, 1981; Egawa and coworkers, 1987; Tobe and coworkers, 1981) and indeloxazine (Tachikawa and coworkers, 1979; Hayes and Chang, 1983; Mizuno and coworkers, 1988); (c) tiapride, a selective $D_2$ blocker (Peselow and Stanley, 1982; Shimizu, 1991); (d) psychotherapeutic drugs such as haloperidol, bromperidol (Niemegeers and Janssen, 1979; Woggon and coworkers, 1979), thioridazine, thiothixene, fluphenazine, perphenazine and molindone (Shimizu, 1991; and Cooper, 1991); (e) antioxidants such as tocopherols, ascorbic acid (Ceballos and coworkers, 1990) or deferoxamine (Halliwell, 1991, pg. 593), as oxidant stress appears to be part of the cytopathology of Alzheimer's disease; (f) acetylcholinesterase inhibitors such as physostigmine (optionally with lecithin) (Thal and Altman Fuld, 1983; Bartus and Dean, 1988; Becker and Giacobini, 1988; Beller and coworkers, 1988; Stern and coworkers, 1988; Thal and coworkers, 1989), heptylphysostigmine (Brufani and coworkers, 1987; Moos and Hershenson, 1989), tetrahydroaminoacridine (tacrine) (Summers and coworkers, 1986; Bartus and Dean, 1988; Mesulam and Geula, 1990, pg. 235) and a hydroxy derivative thereof, (±)-9-amino-1,2,3,4-tetrahydroacridin-1-ol (Shutske and coworkers, 1988; Davies, 1991, pg. S-25), metrifonate (Becker and Giacobini, 1988), velnacrine maleate (Cooper, 1991; Cutler and coworkers, 1992), galanthamine (Nivalin) (Ferris, 1990; Sweeney and coworkers, 1990), sulfonyl fluorides such as methanesulfonyl fluoride (Moos and Hershenson, 1989) and phenylmethylsulfonyl fluoride (Ferris, 1990; Pope and Padilla, 1990), huperzines A and B (Tang and coworkers, 1989; Ferris, 1990), edrophonium (Flood and coworkers, 1988) and miotine and derivatives therof (Moos and Hershenson, 1989); (g) calcium channel blocker agents such as diltiazem, verapamil, nifedipine, nicardipine, isradipine, amlodipine and felodipine; (h) biogenic amines and agents related thereto (Moos and Hershenson, 1989) such as clonidine, a noradrenergic alpha$_2$-receptor agonist (Ferris, 1990; Cooper, 1991), guanfacine, an adrenergic agonist (Cooper, 1991), alaproclate, fipexide, zimeldine and citalopram; (i) anti-rage drugs such as propranolol, carbamazepine and fluoxetine (Cooper, 1991); (j) minor tranquilizers such as benzodiazepine agents (Cooper, 1991); (k) angiotensin-converting enzyme inhibitors such as captopril (Capoten, or in combination with hydrochlorothiazide, Capozide) (Ondetti, 1988; Ferris, 1990; Cooper, 1991; Whitehouse, 1991); (l) agents which may enhance acetylcholine synthesis, storage or release (Moos and Hershenson, 1989) such as phosphatidylchloine, 4-aminopyridine (Sellin and Laakso, 1987; Ferris, 1990; Harvey and Rowan, 1990, pg. 228; Wurtman and coworkers, 1990, pg. 122), bifemelane, 3,4-diaminopyridine (Bartus and Dean, 1988), choline (Summers and coworkers, 1986; Harvey and Rowan, 1990, pgs. 229–232; Sitaram and coworkers, 1978a; Siteram and coworkers, 1978b), vesamicol (Moos and Hershenson, 1989), secoverine, bifemelane, tetraphenylurea (Moos and Hershenson, 1989) and nicotinamide (Moos and Hershenson, 1989); (m) postsynaptic receptor agonists such as arecoline (Sitaram and coworkers, 1978b; Tariot and coworkers, 1988), oxotremorine (Cho and coworkers, 1964; Baratti and coworkers, 1984; Flood and coworkers, 1988; Ferris, 1990), bethanechol (Chan-Palay, 1990, pg. 255; Ferris, 1990), ethyl nipecotate (Moos and Hershenson, 1989) and levacecarnine (Bonavita, 1986; Tempesta and coworkers, 1987; Parnetti and coworkers, 1992); (n) N-methyl-D-aspartate glutamate receptor antagonists such as milacemide (Ferris, 1990; Dysken and coworkers, 1992); (o) ganglioside GM$_1$, as a factor which may potentiate the release of nerve growth factor (Ferris, 1990); (p) mixed cow brain gangliosides (Cronassial) as a composition for induction of nerve axonal sprouting (Bradley, 1990); (q) specific monoamine oxidase-A inhibitors such as moclobemide (Larsen and coworkers, 1984; Wiesel and coworkers, 1985; Burkard and coworkers, 1989; Anand and Wesnes, 1990, pgs. 261–268; Chan-Palay, 1992); (r) monoamine oxidase B inhibitors such as selegiline (Cooper, 1991); (s) thiamine (Cooper, 1991) and a derivative thereof, sulbutiamine (Micheau and coworkers, 1985); (t) D-cycloserine (Francis and coworkers, 1991); (u) anfacine (Ferris, 1990): (v) linopirdine; (w) nonsteroidal anti-inflammatory agents such as those recognized for treatment of rheumatoid arthritis, as well as deferoxamine (McGeer and Rogers, 1992); and (x) serotoneregic receptor antagonists such as ketanserin (Ketan) and mianserin (Mian) (Normile and Altman, 1988).

Some published work has reported that L-deprenyl (selegiline) may work in part by slowing the aging process (Sanchez-Ramos, 1991, pg. 400). Monoamine oxidase B (MAO-B) activity, which is thought to increase with aging in some areas of the brain, generates $H_2O_2$, which in turn may generate neurocytotoxic hydroxyl free radicals (HO$^-$) and leads to subsequent lipid peroxidation. Hence, use of MAO-B inhibitors such as L-deprenyl may have an anti-aging clinical effect (Youdim, 1990). The use of L-deprenyl as a clinical agent for treatment of canine age-related dementia is an example of the potential veterinary applications of the prior art drugs included in this invention (Milgram, 1992).

Other recognized experimental anti-aging agents include (a) vasodilator and other nootropic direct brain metabolic enhancer drugs such as beta-carbolines (Moos and Hershenson, 1989), sabeluzole (Clincke and coworkers, 1988; Moos and Hershenson, 1989; Crook, 1990), razobazam (Hock and McGaugh, 1985; Moos and Hershenson, 1989), exifone (Moos and Hershenson, 1989), idebenone (Moos and Hershenson, 1989), pentoxifylline (Moos and Hershenson, 1989), rolipram (Moos and Hershenson, 1989), vinpocetine (Moos and Hershenson, 1989), citicoline (Moos and Hershenson, 1989), bromvincamine (Moos and Hershenson, 1989), cyclandelate (Ananth and coworkers, 1985; Moos and Hershenson, 1989), ergoloid mesylates such as Hydergine (Moos and Hershenson, 1989), isoxsuprene (Moos and Hershenson, 1989), nafronyl (Moos and Hershenson, 1989), nicergoline (Moos and Hershenson, 1989), papaverine (Moos and Hershenson, 1989), suloctidil (Moos and Hershenson, 1989), vinburnine (Moos and Hershenson, 1989), vincamine (Moos and Hershenson, 1989), vindeburnol (Moos and Hershenson, 1989), nimodipine (Moos and Hershenson, 1989), naloxone (Jensen and coworkers, 1980; Rush, 1986), piracetam (Moos and Hershenson, 1989), pramiracetam (Moos and Hershenson, 1989), aniracetam (Cumin and coworkers, 1982; Moos and Hershenson, 1989), oxiracetam (Franklin and coworkers, 1986; Spignoli and Pepeu, 1987; Crook, 1990), rolziracetam (Moos and Hershenson, 1989), tenilsetam (Pepeu and Spignoli, 1989; Saletu and coworkers, 1989), flunarizine, phosphatidylserine (Delwaide and coworkers, 1986; Zanotti and coworkers, 1986; Amaducci and coworkers, 1987; Crook and Larrabee, 1991), dupracetam (Ferris, 1990; Pepeu and Spignoli, 1990; Cooper, 1991; Whitehouse, 1991), propentophylline (Hindmarch and Subhan, 1985), ebiratide, pyroglutamic acid and etiracetam; (b) acetylcholinesterase inhibitors such as miotine and derivatives thereof (Moos and Hershenson, 1989), physostigmine (Davis and coworkers, 1978; Bartus and Dean, 1988; Beller and coworkers, 1988; Stern and coworkers, 1988), heptylphysostigmine (Brufani and coworkers, 1987; Moos and Hershenson, 1989), tacrine (Bartus and Dean, 1988; Moos and Hershenson, 1989) and a hydroxy derivative thereof, ($\pm$)-9-amino-1,2,3,4-tetrahydroacridin-1-ol (Shutske and coworkers, 1988), sulfonyl fluorides such as methanesulfonyl fluoride (Moos and Hershenson, 1989; Pope and Padilla, 1990), huperzine A (Moos and Hershenson, 1989), huperzine B (Tang and coworkers, 1989), edrophonium (Flood and coworkers, 1988), galantamine (Nivalin) (Sweeney and coworkers, 1990), metrifonate (Moos and Hershenson, 1989) and velnacrine (Cutler and coworkers, 1992); (c) cholinergic muscarinic agonists such as arecoline (Sitaram and coworkers, 1978b; Tariot and coworkers, 1988), oxotremorine (Cho and coworkers, 1964; Baratti and coworkers, 1984; Flood and coworkers, 1988), bethanechol (Moos and Hershenson, 1989), ethyl nipecotate (Moos and Hershenson, 1989) and levacecarnine (Bonavita, 1986; Tempesta and coworkers, 1987; Moos and Hershenson, 1989; Maccari and coworkers, 1990; Parnetti and coworkers, 1992); (d) biogenic amines and co-agents related thereto such as clonidine (Moos and Hershenson, 1989), alaproclate (Moos and Hershenson, 1989; Ferris, 1990), guanfacine (Moos and Hershenson, 1989; Crook, 1990, pg. 213), fipexide (Moos and Hershenson, 1989), zimeldine (Moos and Hershenson, 1989) and citalopram (Moos and Hershenson, 1989); (e) anfacine (Ferris, 1990); (f) acetylcholine synthesis, storage or release modulators such as choline (Sitaram and coworkers, 1978a; Sitaram and coworkers, 1978b; Franklin and coworkers, 1986), phosphatidylcholine (Crook, 1990, pg. 212), 4-aminopyridine (Sellin and Laakso, 1987; Wurtman and coworkers, 1990), 3,4-diaminopyridine (Bartus and Dean, 1988; Harvey and Rowan, 1990, pgs. 229–232), vesamicol (Moos and Hershenson, 1989), tetraphenylurea (Moos and Hershenson, 1989), secoverine (Moos and Hershenson, 1989), bifemelane (Moos and Hershenson, 1989) and nicotinamide (Moos and Hershenson, 1989); (g) N-methyl-D-aspartate glutamate receptor antagonists (Clineschmidt and coworkers, 1982; Crook, 1990, pg. 214; Ferris, 1990) such as milacemide (Moos and Hershenson, 1989), dizocilpine (Moos and Hershenson, 1989) and memantine (Moos and Hershenson, 1989); (h) ganglioside $GM_1$ (Moos and Hershenson, 1989); (t) angiotensin-converting enzyme inhibitors such as captopril (Ondetti, 1988; Moos and Hershenson, 1989; Crook, 1990; Ferris, 1990) and quinapril (Moos and Hershenson, 1989); (j) prostaglandin $B_1$ oligomers ($PGB_x$, Franson and coworkers, 1991) and other antioxidants (Ceballos and coworkers, 1990); (k) the free radical scavenger agent acetylhomocysteine thiolactone (Citiolase) (Totaro and coworkers, 1985); (l) sulbutiamine, a derivative of thiamine (Micheau and coworkers, 1985); and (m) serotoneregic receptor antagonists such as ketanserin (Ketan) and mianserin (Mian) (Normile and Altman, 1988).

Drugs recognized or suggested as experimental symptomatic agents for treatment of tinnitus (nerve deafness) include: (a) antidepressants or antianxiety medications such as amitriptyline HCl (Elavil), perphenazine/amitriptyline combinations (such as Triavil), alprazolam (Xanax) and triptolene: (b) anticonvulsants such as primidone (Mysoline), phenytoin (Dilantin) and carbamazepine (Tegretol); (c) intraveneous lidocaine (Schleuning, 1991); (d) tocainide and flecinide, derivatives of lidocaine which can be administered orally; (e) flunarizine; (f) nicotinamide; (g) aminooxyacetic acid; (h) praxilene; (i) aniracetam; and (j) piracetam (Brummett, 1989). In addition in vitro evidence has been presented which indicates that retinoic acid has a stimulatory effect on differentiation of cochlear hair cells (Sporn and coworkers, 1977; Ott and Lachance, 1979; Travis, 1992).

Presently recognized clinical therapeutic technology for treatment of diabetes, or experimental treatment of diabetes includes use of: (a) various insulin derivatives and compositions such as Humulin 70/30, Mixtard 70/30 or Novolin 70/30; (b) various oral sulfanilamide derivative hypoglycemic agents such as tolbutamide (Orinase), acetohexamide, tolazamide (Tolinase), chlorpropamide (Diabenese), glipizide (Glucotrol) and glyburide (Diabeta, Micronase) (Reed and Mooradian, 1991); (c) vitamin supplements such as vitamin C, vitamin $B_1$ and vitamin $B_6$; (d) angiotensin-converting enzyme inhibitors such as captopril, epi-captopril and zofenopril, which also have free radical scavenging properties (Westlin and Mullane, 1988); (e) antihyperlipidemia agents such as fibric acid derivatives, including gemfibrozil (Lopid) (Garg and Grundy, 1990), bezafibrate (Olsson and Lang, 1978a; Olsson and Lang, 1978b; Zimmermann and coworkers, 1978; Monk and Todd, 1987) and fenofibrate (Elsom and coworkers, 1976; Wulfert and coworkers, 1976); metformin (Hermann, 1979); guar gum (Lalor and coworkers, 1990); 3-hydroxy-3-methylglutaryl-CoA reductase inhibitors such as lovastatin (Mevacor) (Garg and Grundy, 1990), pravastatin and simvastatin; acipimox, an analogue of nicotinic acid (Fuccella and coworkers, 1980; Lovisolo and coworkers, 1981); nicotinic acid (Fuccella and coworkers, 1980); or bile acid sequestrants such as cholestyramine (Garg and Grundy, 1990) and colestipol (Durrington, 1991; Stern and Haffner, 1991); (f) antioxidants such as probucol (Halliwell, 1991, pg. 583; Stern and Haffner, 1991) or $PGB_x$, a polymerized derivative of prostaglandin $B_1$ (Moss and coworkers, 1978; Polis and Polis, 1979; Polis and Cope, 1980; Franson and coworkers, 1991) and, by inference, 2-aminomethyl-4-tert-butyl-6-iodophenol,2-aminomethyl-4-tert-butyl-6-propionylphenol and 2,6-di-tert-butyl-4-[2'-thenoyl]phenol (Swingle and coworkers, 1985; Halliwell, 1991, pg. 596); (g) immunosuppressive drugs such as cyclosporine (Sandimmune) or azathioprine/glucocorticoids (Marks and Skyler, 1991; Skyler, 1991); (h) agents which decrease blood platelet aggregation such as salicylates and dipyridamole (Persantine) (Skyler, 1991); (i) agents which decrease blood viscosity such as pentoxifylline (Trental) (Skyler, 1991); (j) purified cow brain mixed gangliosides (Cronassial) (Bradley, 1990); (k) various agents for treatment of diabetes-related nephrotic syndrome such as furosemide, metolazone, lovastatin, heparin, warfarin, and aminoguanidine (Brownlee and coworkers, 1986); (l) aldose reductase inhibitors (Skyler, 1991) such as sorbinil (Sima and coworkers, 1988), alrestatin (Kikkawa and coworkers, 1983); (E)-3-carboxymethyl-5-[(2E)-methyl-3-phenylpropenylidene]rhodanine (Kikkawa and coworkers, 1983), statil (Daniels and Hostetter, 1989), and tolrestat (Dyck, 1989); and (m) analgesic agents such as acetaminophen for treatment of chronic pain (Weglicki and coworkers, 1990; Cooper, 1991; Guthrie, 1991; Skyler, 1991; Woodley and Whelan, 1992, pg. 224).

Various immunosuppressive agents have been proposed for the treatment of multiple sclerosis (Goodin, 1991). These include: (a) azathioprine (Ellison and coworkers, 1988); (b) copolymer-1 (Bornstein and coworkers, 1988); (c) cyclosporine (Dommasch, 1988); (d) interferons (Knobler, 1988); (e) corticosteroids (Carter and coworkers, 1988); and (f) cyclophosphamide (Carter and coworkers, 1988). Other experimental therapeutic agents for treatment of multiple sclerosis include the use of 4-aminopyridine (Sellin and Laakso, 1987) and 3,4-diaminopyridine (Bever and coworkers, 1990).

Recent studies on amyotrophic lateral sclerosis have included experimental use of purified cow brain mixed gangliosides, and this agent has also been used in experimental clinical trials on alcoholic polyneuropathy and hereditary motor and sensory neuropathies (HMSN) (Bradley, 1990). Thyrotropin releasing factor (Bradley, 1990), serine, glycine and L-threonine (Roufs, 1991) have also been proposed as a possible therapeutic agents for treatment of amyotrophic lateral sclerosis. Other agents which have been proposed as therapeutic agents for treatment of alcoholism include (a) tiapride, a substituted benzamide (Shaw and coworkers, 1987); (b) 4-aminopyridine (Sellin and Laakso, 1987); (c) physostigmine (Stojek and coworkers, 1986); (d) piracetam (Moos and coworkers, 1988, pg. 361); and (e) cyclandelate (Ananth and coworkers, 1985). 3,4-Diaminopyridine is another agent which has been proposed for the treatment of hereditary motor and sensory neuropathy (Windebank, A. J., Mayo Clinic, study in progress as of 1993).

Numerous prior art publications have disclosed that vitamin E (alpha-tocopherol) functions physiologically as a lipid-soluble antioxidant free radical trapping agent. Prior art publications have also described methionine as a water-soluble agent, an essential amino acid, an antioxidant and a free radical trapping agent. Many attempts have been made to clinically treat neuromuscular diseases with antioxidants, generally with little success. For example, Williams and coworkers (1990) reported that dietary supplementation with vitamin E had no significant effect on the clinical status of HMSN patients, while Gerster (1991) reported that dietary supplementation with a combination of vitamin C, vitamin E, beta-carotene, and selenium had the effect of halting or improving degenerative retinal changes in some patients having either age-related macular degeneration or diabetic retinopathy. Additional work of this conceptual nature includes the work of Muller (1990), who reported that alpha-tocopherol has a positive effect on the clinical status of patients suffering from tardive dyskinesia. Yet none of these studies has disclosed the invention contained in copending U.S. patent application Ser. No. 08/026,617, filed Feb. 23, 1993, now abandoned that is, treatment of neurodegenerative diseases by use of primary agents which are primary amine and amine-related substances to inhibit aldehyde-mediated protein and lipid crosslinking, said primary agents capable of being used in combination with known antioxidants and related substances as co-agents.

Vitamin C (ascorbic acid) is widely recognized as a water-soluble antioxidant vitamin. However, numerous published studies which have appeared since 1980 document that vitamin C also can act physiologically as a pro-oxidant (Gutteridge and Wilkins, 1982), an agent which stimulates lipid peroxidation (Chojkier and coworkers, 1989, pgs. 16957 and 16961), and that it is a strong protein glycosylating agent (Ortwerth and Olesen, 1988, pgs. 12, 14, 16, 18 and 20). Thus, for example, in vitro studies have documented the ability of vitamin C to accelerate the process of cataract formation (Slight and coworkers, 1990, pgs. 369–373). In addition, some evidence suggests that ascorbic acid may act as a factor which stimulates certain reactions which are characteristic of inflammatory diseases. For example, the presence of ascorbic acid in the synovial fluid of the arthritic joint may contribute to degradation of hyaluronic acid (Wong and coworkers, 1981; Higson and coworkers, 1988). In light of such information, use of ascorbic acid has been withdrawn from the invention originally disclosed in U.S. patent application Ser. No. 07/660, 561, filed Feb. 21, 1991, now abandoned.

As discussed in U.S. patent application Ser. No. 08/026, 617, filed Feb. 23, 1993, now abandoned a considerable body of prior art publications has provided evidence suggesting that the etiologies of certain neurodegenerative diseases include evidence of chemical crosslinking of neurofilaments. Such studies include work on hereditary motor and sensory neuropathies (Hughes and Brownell, 1972; Brimijoin and coworkers, 1973; van Weerden and coworkers, 1982; and Goebel and coworkers, 1986), giant axon neuropathy (Prineas and coworkers, 1976), diabetic polyneuropathy (Yamamura and coworkers, 1982; Sidenius and Jakobsen, 1982; and Tomlinson and Mayer, 1984), Alzheimer's disease (Wisniewski and coworkers, 1970; Iqbal and coworkers, 1978, and Wisniewski and coworkers, 1982, pp. 110–112), Down's syndrome (Goodison and coworkers, 1989), Pick's disease (Yoshimura, 1989), Parkinson's disease (Oppenheimer, 1976, pp. 612–614; and Cohan, 1989, pg. 167), amyotrophic lateral sclerosis (Carpenter, 1968), infantile spinal muscular atrophy (Lee and coworkers, 1989), Friedreich's ataxia (Lamarche and coworkers, 1982) and alcoholic polyneuropathy (Appenzeller and Richardson, 1966).

Likewise, evidence of increased deposition of lipofuscin in various neurodegenerative diseases has been presented. This observation has been documented in studies on amyotrophic lateral sclerosis (Carpenter, 1968), Guam Parkinsonism-dementia (Tan and coworkers, 1981), Alzheimer's disease (and Tsuchida and coworkers, 1987; Moran and Gomez-Ramos, 1989;), Huntington's disease (Tellez-Nagel and coworkers, 1974), Meniere's disease (Ylikoski and coworkers, 1980), and juvenile ceroid-lipofuscinosis (Schwendemann, 1982). Heart lipofuscin has been shown to have the following general composition: lipids, 20–50%; protein, 30–60%; and strongly pigmented resin-like hydrolysis-resistant material, 9–20%. Although the exact nature of the hydrolysis-resistant chemical bonds remains to be unequivically defined, the similarity between lipofuscin fluorescence and that of Schiff bases formed between malonaldehyde and primary amines suggests that similar chemical crosslinks may be part of lipofuscin structure (Tsuchida and coworkers, 1987).

The results of several published research studies suggest that dysfunctional lipid peroxidation may be a contributing factor in the etiology of Parkinson's disease (Fahn, 1989), multiple sclerosis (Hunter and coworkers, 1985) and Duchenne muscular dystrophy (Kar and Pearson, 1979; Jackson and coworkers, 1984; Hunter and Mohamed, 1986).

Age-related changes share much in common with other disease entities discussed in this invention. At the biochemical level, the two most clearly defined pathological events within aging mammalian cells appear to be (1) the progressive accumulation of lipofuscin and (2) concomitant appearance of high molecular weight protein aggregates and/or polymeric lipid-protein complexes (Shimasaki and coworkers, 1984). Age-onset peripheral nerve damage has been recognized in both man and experimental animals. Such polyneuropathy is extremely common in the elderly (Cohan, 1989). Examination of human sural nerve biopsies has revealed age-related degeneration of both myelinated and non-myelinated fibers. This process includes the occurrence of unusual inclusions within axons consisting of filament bundles which appear more dense than those of normal neurofilaments (Ochoa and Mair, 1969). As peripheral, autonomic and central nervous system neurons lose functional ability as part or the aging process a variety of body functions under their control are adversely affected.

Autonomic nervous system functions include urinary continence, peristaltic movement of the digestive tract, sexual response and breathing. Forms of neurological dysfunction lying within the scope of this invention which may cause urinary incontinence include: Alzheimer's senile dementia, demyelinating diseases such as multiple sclerosis, peripheral nerve lesions, diabetes mellitus and alcoholic polyneuropathy (Palmer, 1985, pg. 27). Causes of urinary incontinence which may be classified as urological/gynecological, psychological or environmental (Palmer, 1985, pg.22) do not fall within the scope of this invention. Drugs which are presently recognized for use in treatment include cholinergics such as bethanechol, anti-cholinergics such as belladonna and alpha-adrenergics such as ephedrine (Palmer, 1985, pg. 58). None of these therapeutic agents have been heretofore recognized as drugs falling within the pharmacological scope of U.S. patent application Ser. No. 08/026,617, filed Feb. 23, 1993, now abandoned, although this inventor regards the alpha-adrenergics ephedrine, which contains a secondary amine group, and phenylpropanolamine, which contains a primary amine group, as potential carbonyl-trapping agents.

Peristaltic movement of the digestive tract, which is controlled by the autonomic nervous system, may be adversely affected due to aging, diabetes (Bergmann and coworkers, 1992) or other clinical disorders. Drugs presently recognized for the treatment of gastroesophageal reflux disease, hypoperistalsis and/or delayed gastric emptying include (a) metoclopramide (Reglan); (b) cisapride (Prepulsid) (Bergmann and coworkers, 1992); (c) famotidine (Pepcid); (d) cimetidine (Tagamet); (e) ranitidine (Zantac); (f) omeprazole (Prilosec); and galanthamine (Sweeney and coworkers, 1990).

In their study on human senile and diabetic cataracts, Rao and Cotlier (1986) noted evidence that crosslinking of lens proteins via nonenzymatic glycosylation appears to be an underlying pathological mechanism for both cataract types. In their analysis of senile cataracts these investigators observed statistically significant decreases in soluble protein content, increases in insoluble proteins, decreases in free epsilon-amino groups of insoluble proteins and increases in observed 5-hydroxymethyl furfural levels (that is, reducible Maillard products) in insoluble proteins. Similar data were obtained from diabetic cataracts. Earlier studies showed the appearance of covalently crosslinked protein polymers during senile cataract formation (Selkoe and coworkers, 1982). Evidence of increased lipid peroxidation in the aged human lens has also been presented (Bhuyan and coworkers, 1986).

In addition, several published studies have presented evidence which implicates lipid peroxidation products in the etiology of atherosclerosis (Halliwell, 1991, pg. 583). 4-Hydroxy-2,3-transnonenal covalently binds to lysine and other peptide residues of low-density lipoprotein much more readily than malondialdehyde. Hence, it (as well as other aldehydes) may play a role in the etiology of atherosclerotic lesions (Jurgens and coworkers, 1986; and Esterbauer and coworkers, 1987). As summarized by Steinbrecher (1987), there is reason to believe that reactive lipid peroxidation agents form Schiff base adducts with the lysine epsilon-amino groups of low density lipoproteins (LDL). Such modified LDL's are recognized by high-affinity acetyl-LDL receptors located on macrophages, which results in lipid accumulation. Lipid-laden macrophages appear to be precursors of the foam cells which populate early atherosclerotic lesions (Steinbrecher, 1987). Use of the invention of U.S. patent application Ser. No. 08/026,617, filed Feb. 23, 1993, now abandoned, in combination with previously recognized medicaments for treatment of atherosclerosis, hypertension and ischemic heart disease, as defined herein, may provide additional clinical benefit for patients suffering from these chronic, age-related diseases. Previously recognized drugs for treatment of atherosclerosis include hypolipidemic agents such as fenofibrate (Elsom and coworkers, 1976; Wulfert and coworkers, 1976), bezafibrate (Olsson and Lang, 1978a; Olsson and Lang, 1978b; Zimmermann and coworkers, 1978; Monk and Todd, 1987), metformin (Hermann, 1979), nicotinic acid (Fuccella and coworkers, 1980), acipimox (Fuccella and coworkers, 1980; Lovisolo and coworkers, 1981) and guar gum (Lalor and coworkers, 1990), as well as antioxidants such as probucol (Halliwell, 1991, pg. 583; Stern and Haffner, 1991) and prostaglandin $B_1$ oligomers ($PGB_x$) (Moss and coworkers, 1978; Polis and Cope, 1980). Previously known medicaments for treatment of hypertension (Woodley and Whelan, 1992, pp. 64–75) include diuretics, beta-adrenergic antagonists, calcium antagonists, angiotensin-converting enzyme inhibitors, centrally acting alpha-adrenergic agonists, direct-acting vasodilators, alpha-adrenergic antagonists and peripherally acting anti-adrenergic agents. At least one peptide-based renin inhibitor (A-725517, Abbott Laboratories) has also been mentioned as a prospective anti-hypertensive agent (Kleinert and coworkers, 1992). Previously known medicaments for treatment of ischemic heart disease include nitroglycerin, beta-adrenergic antagonists, calcium channel antagonists and aspirin (Woodley and Whelan, 1992, pp. 81–84). Recognized ventricular antiarrhythmic drugs include sotalol, mexilitene, propafenone, quinidine gluconate, procainamide and pirmenol (Toivonen and coworkers, 1986). Some published information indicates that at least part of the physiological activity of some cardioprotective drugs may be due to their possessing certain free radical scavenging and/or antioxidant properties. This appears to be the case for (a) beta-blocker agents such as propranolol, pindolol, metoprolol, atenolol and sotalol; (b) calcium channel blockers such as nifedipine, verapamil and diltiazem; (c) probucol; and (d) angiotensin converting enzyme inhibitors such as captopril, epicaptopril and zofenopril (van Gilst and coworkers, 1986; Ondetti, 1988; Weglicki and coworkers, 1990).

This inventor has published the findings of a study which may describe part of the physiological basis of one of the hereditary motor and sensory neuropathies (Shapiro and coworkers, 1986; Shapiro and Kahn, 1990). In this study urine samples from five autosomal dominant chromosome 17 HMSN patients of the same family and five urine samples from age- and sex-matched normal control subjects were examined. By use of gas chromatography/mass spectrometry the urine concentrations of approximately 150 organic acids could be estimated in each sample. Average HMSN organic acid values differed most notably from normal values in a set of three physiologically related metabolites, 5-hydroxymethyl-2-furoic acid, 2,5-furandicarboxylic acid and 5-carboxy-2-furoylglycine. Average patient urine concentrations of these three organic acids were 29% 50% and 37% of controls, respectively.

5-Carboxy-2-furoylglycine is a mono-glycine conjugate of 2,5-furandicarboxylic acid. Hence 2,5-furandicarboxylic acid was measured directly as the dicarboxylic acid and indirectly as its mono-glycine conjugate. Glycine conjugation is a well recognized liver detoxication/excretion reaction, applied broadly to the

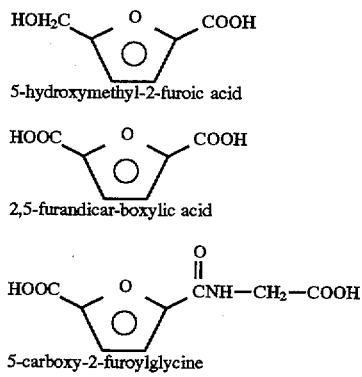

carboxylic acid products of many endogenous metabolites, dietary components and drugs (Williams, 1959, pp. 349–353).

Previous research studies have determined that 5-hydroxymethyl-2-furoic acid and 2,5-furandicarboxylic acid are oxidation products of an aldehyde precursor, 5-hydroxymethyl-2-furfural (Jellum and coworkers, 1973). Decreased levels of furancarboxylic acid excretion suggest that this metabolite, and possibly other aldehyde precursors suck as 2,5-furandialdehyde, is not being detoxicated and cleared in a normal manner. Several enzymes may be involved in the normal detoxication of furanaldehydes. Oxidation of furanaldehydes to carboxylic acid products is known to occur in mammalian tissues (Williams, 1959, pp. 550–551), but a specific furanaldehyde dehydrogenase has not been characterized.

Prior art studies have demonstrated the existance of several mammalian aldehyde dehydrogenases which possess wide substrate specificities (Hjelle and Petersen, 1983; Lindahl and Evces, 1984). These are NAD(P)-dependent enzymes. Normal detoxication of furanaldehydes may involve roles for one or more of these enzymes, or their flavin-dependent counterpart, and the HMSN patients studied by this inventor and coworkers may have a genetic defect in this process.

5-Hydroxymethyl-2-furfural should be regarded as a potential protein crosslinking agent (Jellum and coworkers, 1973, pg. 200). 2,5-Furandialdehyde is even more suspect as a potential crosslinking agent, as it bears two highly reactive aldehyde groups. It is a close structural analogue of 2,5-hexanedione, a potent chemical peripheral neurotoxin implicated in the covalent crosslinking of neurofilaments.

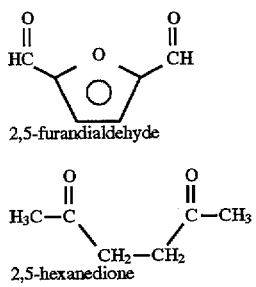

Hence 2,5-furandialdehyde appears to be a particularly interesting metabolite. It is cleared from the body only with difficulty in patients having a genetic peripheral neuropathy; and its size, three dimensional shape and analogous bi-carbonyl structure make it structurally related to a chemical known to induce peripheral neuropathy in mammals after relatively trace levels of exposure (Krasavage and coworkers, 1980). Covalent chemical crosslinking of neurofilaments has been shown to be the basis of 2,5-hexanedione neurotoxicity (Carden and coworkers, 1986).

There is reason to believe that 5-hydroxymethyl-2-furfural and 2,5-furandialdehyde can originate as by-products of either of two general areas of metabolism, that of sugars and lipids. The thought that secondary products of lipid peroxidation might include metabolites such as 5-hydroxymethyl-furanaldehyde and 2,5-furandialdehyde has attracted little, if any, attention within the biomedical research community prior to submission of U.S. patent application Ser. No. 07/660,561, filed Feb. 21, 1991, now abandoned. As described in that disclosure, 2,5-dimethyl furan appears to be a key intermediate in the process leading to the appearance of these aldehydes.

5-Hydroxymethyl-2-furfural and 2,5-furandialdehyde can also form spontaneously from glucose or fructose under mildly acidic aqueous conditions and, as they are readily generated during food cooking, they are part of the human diet. There is reason to believe that these aldehydes, among others, may play a significant role in the etiology of diabetic polyneuropathy. As discussed in U.S. patent application Ser. No. 08/026,617, filed Feb. 23, 1993, now abandoned, it is the understanding of this inventor that conversion of fructose to 5-hydroxymethyl furfural and possibly 2,5-furandialdehyde may in fact be the basis of neurotoxic consequences resulting from activation of the polyol pathway seen in diabetic polyneuropathy.

Studies during the past decade have clearly established that long-term hyperglycemia associated with diabetes leads to generalized non-enzymatic addition of reducing sugar residues to proteins via covalent addition to amine functional groups located on amino acid sidechains. Following initial addition, several structural rearrangements occur which can result in intra- and intermolecular crosslinking of proteins (Brownlee, 1990). This is a complex series of non-enzymatic reactions which are not completely defined at this time. Yet, as discussed in U.S. patent application Ser. No. 08/026,617, filed Feb. 23, 1993, now abandoned, there is reason to believe that this phenomenon is involved in diabetic vascular changes, diabetic nephropathy, cataracts, diabetic retinopathy and other secondary diabetic symptomology. Such reactions may also underlie much of the biochemistry of aging (Pongor and coworkers, 1984).

The nature of the chemical bonds responsible for holding together the neurofibrillary tangles of Alzheimer's disease (AD) and other neurodegenerative diseases is still poorly understood. What limited information is publicly available on this question is comparable with the overall inventive concept of U.S. patent application Ser. No. 08/026,617, filed Feb. 23, 1993, now abandoned; that cytotoxic consequences result from various forms of spurious covalent bond protein crosslinking, at least some forms of which may be clinically treated by the pharmacological procedures described therein.

Both AD senile plaques and neurofibrillary tangles consist largely of networks of intermediate size protein filaments helically wound in pairs having a periodicity of 80 nm (Selkoe and coworkers, 1982). Isolated paired helical filament (PHF) has proven to have remarkable properties of chemical stability. PHF chemical cross-linking bonds are not broken by sodium dodecyl sulfate, beta-mercaptoethanol, 9.5M urea, two percent Triton X-100, one percent NP-40, 6M guanidine hydrochloride, 0.2N HCl or 0.2N NaOH. As heating of PHF in the presence of either reducing agents such as beta-mercaptoethanol or detergents such as Triton X-100 or NP-40 did not solubilize PHF, bonds other than disulfide are implicated in amino acid crosslinking of this type of rigid intracellular polymer. This unusual chemical stability has seriously impeded PHF analysis by gel electrophoresis (Selkoe and coworkers, 1982). As a postulated mechanism for such unusual crosslinking Selkoe and coworkers (1982) noted that "different protein polymers in senile cataracts, terminally differentiated epidermal cells, and red blood cells are covalently crosslinked by gamma-glutamyl-epsilon-lysine sidechain bridges." Like PHF, these other protein complexes are insoluble in sodium dodecyl sulfate and not solubilized by reducing agents. Selkoe and coworkers (1982) speculated that such gamma-glutamyl-epsilon-lysine crosslinks may also form pathologically in nerve cells, as human brain contains a transglutaminase capable of acting on normal neurofilament to form an insoluble high molecular weight filamentous polymer.

The clinical neurology literature includes many descriptions of patients having an incipient form of a disease, patients showing the recognized symptoms of a disease and additional symptomology, and patients demonstrating concurrent clinical symptomology of two or more recognized disease entities. Such clinical disorders are frequently excluded from biochemical studies due to inherent problems of classification and their happenstance occurrence. Hence comparatively little research information is available on such clinical phenomena. Yet it is the understanding of this inventor that information available on the etiologies of well recognized neurological disorders, as summarized herein, can also be extrapolated to infer that the drug therapies described in this invention may also be applied with success to the incipient and more complex forms of the diseases mentioned above.

OBJECTS OF THE INVENTION

Accordingly, it is a general object of this invention to treat neurological diseases and etiologically related symptomology by use of carbonyl trapping agents in combination with known antioxidant free radical trapping co-agents, and in combination with various additional known medicaments which have been shown to or may contribute to the alleviation of symptomology of the diseases addressed herein, so as to overcome the disadvantages of the prior art.

In particular, it is an object of the present invention that the drug compositions originally described in U.S. patent application Ser. No. 07/660,561, filed Feb. 21, 1991, now abandoned, may be combined with known medicaments so as to provide increased clinical value in the treatment of disease symptomology for disorders featuring well defined neurofilament associated pathology, lipofuscin accumulation and/or aberrant lipid peroxidation, including: diabetic polyneuropathy and related metabolic symptomology; Alzheimer's presenile/senile dementia; Down's syndrome; Parkinson's disease; amyotrophic lateral sclerosis; age-related atrophy of peripheral sensory and motor nerves, autonomic nerves, and neurons of the central nervous system, and pathophysiologically related changes in the cardiovascular system, kidney, and optic lens; alcoholic polyneuropathy; multiple sclerosis; olivopontocerebellar atrophy; Huntington's disease and disorders clinically related thereto.

It is another object of the present invention that in so far as the therapeutic procedures described herein may serve to delay the necessity of initiating the use of known medicaments or to decrease the dosages of known medicaments required to achieve beneficial effects, the period of prior art drug therapeutic value may be extended and detrimental clinical side effects resulting from use of known medicaments may be decreased, so that overall patient treatment may be improved.

It is another object of the present invention that in so far as the therapeutic procedures described herein may be of benefit for improvements in autonomic nervous system function, it is claimed that such procedures may better ameliorate symptomology of urinary incontinence.

It is yet another object of the present invention that in so far as the therapeutic procedures described herein may serve to covalently bind and sequester agents which may underlie, in part, the etiology of atherosclerosis, it is believed that such procedures may be of benefit in treatment of this age-related disorder.

It is a further object of this invention that the absorbable amine and amine-related substances and derivatives thereof described herein when used in combination with specified co-agents may be clinically applied to treat veterinary disorders comparable to those human disorders described above.

It is a further object of this invention to draw attention to and originally recognize that the appearance of one or more chromosome 17 HMSN-specific cultured fibroblast proteins may be used as a clinical diagnostic procedure for defining the presence of this genetic disease.

Use of absorbable amine and amine-related primary agents, non-absorbable amine and amine-related co-agents, co-agents which inhibit lipid peroxidation, human growth hormone co-agent, vitamin co-agents which may be inadvertently depleted, co-agent metabolites such as glycine which may be depleted within the body, and sulfhydryl co-agents as defined in U.S. patent application Ser. No. 08/026,617, filed Feb. 23, 1993, now abandoned, is included in the present invention, in combination with use of various additional known medicament co-agents which have been shown to or may contribute to the alleviation of symptomology of the diseases addressed herein. In addition, the present invention includes use of various co-agents which may facilitate glutathione activity, such as N-acetylcysteine, oxo-thiazolidine-carboxylate, timonacic acid, cysteamine, lipoamide derivatives such as malotilate (Kantec), sulfarlem (ADT), and oltipraz (Dansette and coworkers, 1990), as these co-agents may further serve to improve the invention described in U.S. patent application Ser. No. 08/026,617, filed Feb. 23, 1993, now abandoned.

DETAILED DESCRIPTION OF THE PREFERRED EMBODIMENT

1. Physiological Basis of the Invention

These and other objects of this invention are achieved by providing a novel method for clinical treatment of neurological diseases and etiologically related clinical symptomology. While the causes of these diseases are diverse and largely undefined at present, these disorders nevertheless share many common characteristics at the cellular level.

For any one neurological disease certain nerve cells, usually with a characteristic anatomical distribution, will undergo a process of intracellular deterioration, eventually leading to cell death. In this process certain normal intracellular structures are progressively altered in terms of structure, as apparent by electron microscopy, and function, as indicated by enzyme activities. In addition, certain pathological structures, not normally present, will appear and usually develop in terms of number and size until they come to dominate the intracellular environment. These neuropathological changes end in cell death.

Biomedical information now publicly available indicates or suggests that spurious, pathological chemical crosslinking of normal intracellular structures is a fundamental aspect of the neurological diseases addressed herein. Such covalent bond crosslinking of protein and lipid subcellular elements appears to underlie the formation of at least four common neuropathological structures: (1) polymerized aggregates of structural protein filaments (e.g., excess neurofilament accumulation), (2) heterogeneous protein aggregates (e.g., neurofibrillary tangles), (3) amorphous protein and lipid aggregates (e.g., senile plaques), and (4) lipofuscin granules, which are amorphous aggregates rich in lipid chemical complexes. Spurious, excess protein chemical crosslinking is also apparent in the extracellular compartment in some of these diseases, for example, blood capillary basement membrane thickening in long term diabetes mallitis. In addition, analogous pathological chemical crosslinking of DNA can also occur under certain circumstances, thus further damaging cells prone to such attack. Based on the presence of one or more of the neuropathological events noted above, the drug treatment protocols falling within the scope of this invention may be of benefit to patients having one of the diseases addressed herein.

Moving to the chemical level, considerable biomedical literature indicates that certain sites on normal proteins and lipids are specific targets for spurious chemical crosslinking, most notably the epsilon-amino groups of lysine residues in proteins and the amine groups of phosphatidylethanolamine molecules in cell lipid membrane bilayers. These primary amine groups are especially prone to attack by small molecular weight carbonyl-containing hydrocarbons. Such carbonyl-containing molecules may originate by many pathological mechanisms still only partly defined, but, in general, they originate from peroxidation of fatty acids or as by-products of sugar metabolism. A monocarbonyl specie can bind to a protein or amino-lipid, alter its three dimensional structure and possibly affect its chemical activity. A dicarbonyl hydrocarbon can react with two amine groups, thus making a covalent chemical crosslink. The specific primary pathological changes which underlie this type of deterioration remain largely undefined, but their structural products have been characterized in many respects.

Kikugawa and Beppu (1987) noted that lipid radicals, hydroperoxides and their secondary products react with neighboring protein molecules, damaging protein structure and function. Such damage includes formation of fluorescent chromophores, lipid-protein adducts, and protein-protein crosslinks. Using sodium dodecyl sulfate-polyacrylamide gel electrophoresis, these investigators demonstrated that malonaldehyde (also known as malondialdehyde), a bifunctional molecule having two aldehyde groups, can covalently crosslink proteins. This reaction primarily involves Schiff base formation with protein epsilon-amino groups on the sidechains of lysine residues. Kikugawa and Beppu (1987) also reported that monofunctional aldehydes such as acetaldehyde, 1-hexanal, 1-heptanal and 2,4-decadienal can also crosslink proteins, generating fluorescent products. This biochemical curiosity still not well understood. Some form of self-condensation may be involved.

The generation of water soluble, carbonyl-containing products of lipid peroxidation can be readily demonstrated under simple in vitro conditions. Schauenstein (1967) incubated suspended polyunsaturated fatty acid esters with water at 40° C. in the presense of air and demonstrated the generation of numerous such products. These included oct-2-trans-en-1-al, 4-hydroperoxynon-2-en-1-al, 1-hydroxyheptan-2-one, 4-hydroxy-2-trans-octen-1-al, as well as numerous other water soluble products not characterized in Schauenstein's investigation. Other investigators have also documented the generation of numerous carbonyl-containing products of lipid peroxidation, however the exact identities of many of these agents remains undefined (Esterbauer and coworkers, 1982).

The conceptual similarities between lipid peroxidation-induced protein crosslinking and protein crosslinking associated with non-enzymatic glycosylation has been noted in the research literature (Kikugawa and Beppu, 1987). Some evidence has been presented which suggests that a slow, age-dependent deterioration of biological systems which counteract lipid peroxidation may be a fundamental part of the aging process (Harman, 1971). This concept is sometimes referred to as the free radical theory of aging.

A variety of furans, aldehydes and ketones have been identified in normal human urine (Zlatkis and Liebich, 1971; Matsumoto and coworkers, 1973). These include 2,5-dimethyl furan, 2-methyl furan, other alkyl furans, and a variety of five- to eight-carbon alkyl aldehydes and ketones. Yancey and coworkers (1986) induced lipid peroxidation in rats by use of a defined diet deficient in both vitamin E and selenium, and then studied volatile urine metabolites. The results showed that urine of vitamin E deficient animals contained 16 carbonyl compounds which were present at elevated levels of statistical significance. The greatest increases observed were for hydroxy-acetylaldehyde (676%), benzaldehyde (538%) and furfural (487%). In discussing their findings, Yancey and coworkers concluded, in part:

> Both capillary GC and LC results appear to implicate aldehydes (both normal and unsaturated) and related compounds, furan derivatives, as characteristic products of lipid peroxidation. Elevated aldehyde levels were also noticed in our earlier investigations of urinary metabolites of both long-term diabetic rats and genetically diabetic mice. Since an increased lipid peroxidation process has been associated with the diabetic condition, it is not surprising that known peroxidation metabolites should be more abundant in diabetic than normal urine samples ... Increased lipid peroxidation clearly results in a greater production of metabolites that are either proven or suspected neurotoxins.

Non-enzymatic in vitro autoxidation of furfural has been described, which yields a mixture of products which includes 2-furoic acid (Dunlop and Peters, 1953, pg. 385). Likewise, Williams (1959, pp. 550–551) has described the mammalian in vivo oxidation of 2,5-dimethyl furan to 5-methyl-2-furoic acid and of 5-hydroxymethyl-furfural to 5-hydroxymethyl-2-furoic acid. In principle, the process of enzymatically converting hydrocarbon functional groups such as a methyl group of 2,5-dimethyl furan to a carboxylic acid group involves three consecutive oxidation reactions.

As summarized above, and discussed at greater length in U.S. patent application Ser. No. 08/026,617, filed Feb. 23, 1993, now abandoned, 2,5-dimethyl furan is a recognized secondary product of lipid peroxidation and there is reason to believe that it may be oxidized in vivo to products such as 5-hydroxymethyl-2-furancarboxylic acid and 2,5-furandicarboxylic acid. This, in turn, suggests that 5-hydroxymethyl furfural and 2,5-furandialdehyde may be metabolic intermediates in this process.

It is the unique belief and understanding of this inventor that the long term generation of furan aldehyde agents as by-products of lipid peroxidation can serve as a metabolic basis or underlying contributing factor in the etiology of diabetic symptomology, the etiology of other neurological diseases featuring evidence of Schiff base type chemical crosslinking phenomena, and in the etiology of age-related symptomology. It seems reasonable to this inventor that the chromosome 17 HMSN patients discussed above were experiencing toxic long term consequences of furanaldehyde exposure as a consequence of defective ability to oxidize furanaldehydes which are normal products of lipid metabolism. Failure to dispose of these reactive metabolites efficiently may predispose the patients to pathological events initiated by spurious protein crosslinking. For diabetic patients, on the other hand, excess levels of furanaldehyde metabolites seem to appear as a consequence of chronic hyperglycemia. It appears that in the diabetic state in vivo capacity to oxidize or otherwise detoxify furanaldehydes is simply exceeded by endogenous generation of these toxic metabolites. Thus there does appear to be a degree of similarity between these two disease states, reflected in similar peripheral neuropathies, yet their metabolic origins appear to be different.

The present invention discloses protocols of drug therapy for treatment of the medical disorders addressed herein. As originally described in U.S. patent application Ser. No. 07/660,561, filed Feb. 21, 1991, now abandoned, these pharmacological reactions are based on the ability of primary amine and amine-related agents to react with aldehyde functional groups of potentially toxic agents, yielding covalently bound Schiff base products, and one may add to the beneficial effects of said treatment by compounding the primary agent with various co-agents.

U.S. patent application Ser. No. 08/026,617, filed Feb. 23, 1993, now abandoned, sets forth that absorbable pharmaceutical agents such as p-aminobenzoic acid when administered to humans in oral dosages of from one gram/day to 40 grams/day may be used as therapeutic agents for treatment of certain neurological diseases and for treatment of other pathophysiologically related clinical phenomena. U.S. patent application Ser. No. 08/026,617, filed Feb. 23, 1993, now abandoned, also comprises use of orally administered, non-absorbable polyamine polymeric co-agents such as chitosan for use in treatment of the disease entities noted above. Such non-absorbable pharmacological co-agents may act to covalently bind and sequester potentially toxic carbonyl compounds present in the diet. In addition, U.S. patent application Ser. No. 08/026,617, filed Feb. 23, 1993, now abandoned, comprises the use of such chemical agents and co-agents in combination with antioxidants such as alpha-tocopherol, suspending reagents such as carboxymethyl cellulose for the compounding of oral tablets, other vitamins, and chemical conjugating co-agents which may facilitate kidney drug elimination, such as glycine. The present disclosure describes the inventive concept of using the therapeutic technology of U.S. patent application Ser. No. 08/026,617, filed Feb. 23, 1993, now abandoned, in combination with pharmaceutical agents previously recognized as having, or possibly having some medicinal value for treatment of the disease entities noted above.

2. Examples of Orally Administered Absorbable Drug Products Useful in the Present Invention It is the central premise of U.S. patent application Ser. No. 08/026,617, filed Feb. 23, 1993, now abandoned, that an opportunity exists, heretofore unrecognized, for pharmacological intervention in some neurological diseases by use of water soluble, small molecular weight primary amine agents and chemical derivatives thereof. Such pharmacological agents, administered orally, can compete with cellular protein and lipid amine groups for reaction with disease-induced carbonyl-containing hydrocarbons. Such derivatized pharmacological agents can then be excreted by the kidneys. This process, while not necessarily addressing the primary etiology of a neuropathy, may be of practical clinical benefit to significantly delay the onset of a disease, stop disease progression for an extended period, or lead to observable improvement in patient status.

Ideally, such an absorbable pharmacological agent should have several characteristics. It should be water soluble and of small molecular weight so that it can passively and readily diffuse throughout the body, including within cells. It should have at least one chemically active trapping group, such as a primary amine group (R—$NH_2$), for reaction with carbonyl groups (R—CHO or $R_1$—CO—$R_2$) to yield covalent bonded products. It should otherwise not interact with normal cell metabolism or do so in ways which are not cytotoxic. It should be tolerated by the body in relatively high dosages (range of grams per day) and for extended periods. In addition, such an absorbable pharmacological agent and its metabolic derivatives should be readily absorbed by kidney tissue and excreted in urine without nephrotoxic consequences.

4-Aminobenzoic acid (also known as p-aminobenzoic acid or PABA) is an example of the absorbable primary agent of this invention. PABA has a small molecular weight (137, free acid) and is water soluble. It has a primary amine group which should readily react with carbonyl-containing metabolites under physiological conditions. PABA has already been commercially marketed for other health applications and it has been used effectively and safely by millions of people. It has been used as a popular sun screen topical cream additive and it has also been used as an antifibrotic prescription drug for treatment of dermatomyositis, scleroderma and several clinically related skin disorders. On a prescription basis PABA is recognized for use in a dosage of 12 grams/day for up to two years.

The metabolic fate of PABA in humans has been actively investigated and well reported in the biomedical literature. It is so actively metabolized via several mechanisms and quantitatively removed in urine that PABA excretion has become a widely recognized standard for measuring urinary clearance. Small amounts of PABA are normally present in the human diet. It is recognized as being a vitamin for many organisms and is classified as a member of the vitamin B complex. As a vitamin for human use PABA is commercially marketed in the dosage range of 5 to 550 mg/day.

For any of the chemical derivatives of PABA listed herein as useful in the present invention, it is believed that the salt forms, free acid form, ester derivatives, amide derivatives and analogous non-aromatic benzene ring derivative (i.e., cyclohexane carboxylic acid derivative) thereof will also be useful. Examples of the class of primary agents (molecular weight range 100 to 1,400) of the present invention may be summarized as noted below in chemical structures I, II and III.

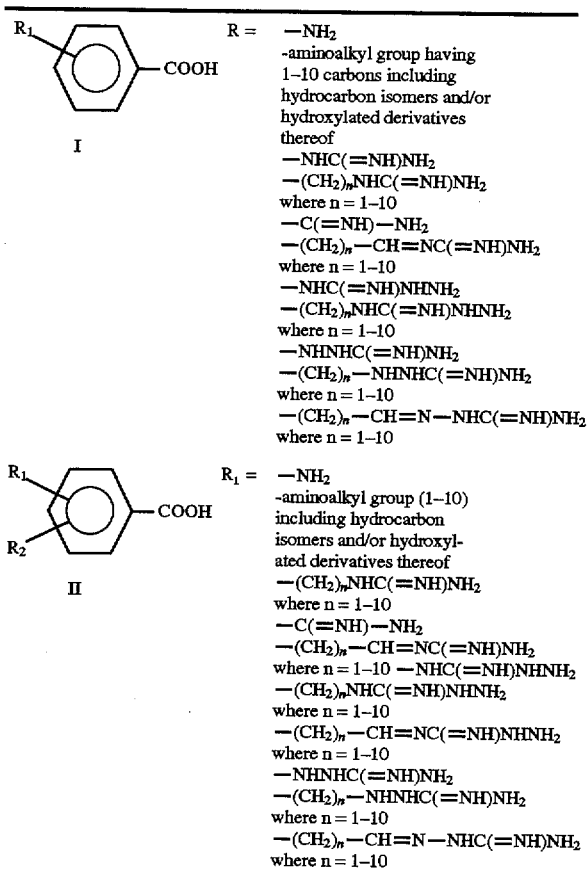

-continued

R$_2$ = NH$_2$
—OH
—O—CH$_3$
—O—R' with alkyloxy group R' having 2–10 carbons including hydrocarbon isomers and/or hydroxylated derivatives thereof
-aminoalkyl group (1–10 carbons) including hydrocarbon isomers and/or hydroxylated derivatives thereof
—SO$_3$H
—CH$_3$
—(CH$_2$)$_n$CH$_3$ where n = 1–10 including hydrocarbon isomers and/or hydroxylated derivatives thereof

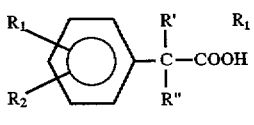

III

R$_1$ = —(CH$_2$)$_n$—NH$_2$ where n = 0–10 including isomers of the aminoalkyl group and hydroxylated derivatives thereof
—C(=NH)—NH$_2$
—NHC(=NH)NH$_2$
—(CH$_2$)$_n$NHC(=NH)NH$_2$ where n = 1–10
—(CH$_2$)$_n$—CH=NC(=NH)NH$_2$ where n = 1–10
—NHC(=NH)NHNH$_2$
—(CH$_2$)$_n$NHC(=NH)NHNH$_2$ where n = 1–10
—(CH$_2$)$_n$—CH=NC(=NH)NHNH$_2$ where n = 1–10
—NHNHC(=NC)NH$_2$
—(CH$_2$)$_n$—NHNHC(=NH)NH$_2$ where n = 1–10
—(CH$_2$)$_n$—CH=N—NHC(=NH)NH$_2$ where n = 1–10

R$_2$ = —NH$_2$
—H
—OH
—O—CH$_3$
—O—R$_3$ with alkyloxy group R$_3$ has 2–10 carbons including hydrocarbon isomers and/or hydroxylated derivatives thereof
-aminoalkyl group (1–10 carbons) including hydrocarbon isomers and/or hydroxylated derivatives thereof
—SO$_3$H
—CH$_3$
—(CH$_2$)$_n$CH$_3$ where n = 1–10 including hydrocarbon isomers and/or hydroxylated derivatives thereof

R' = —H
—CH$_3$
—OH
R" = —H
—CH$_3$
—OH

3. Examples of Orally Administered Non-Absorbable Co-Agents Useful in the Present Invention As discussed in U.S. patent application Ser. No. 08/026,617, filed Feb. 23, 1993, now abandoned, the diet is a significant source of carbonyl agents. These agents may be contributing factors in the aging process, may predispose humans for other neurodegenerative disorders, may be contributing factors in atherosclerosis, may be contributing factors in inflammatory diseases and may also be contributing factors in the initiation of carcinogenesis. Such carbonyl agents, while contributing positively in some instances to the flavor of foods or beverages (for example, cheeses or wines), have no recognized nutritional value. It was proposed in U.S. patent application Ser. No. 08/026,617, filed Feb. 23, 1993, now abandoned, that certain dietary supplements can be of public health benefit by their ability to covalently trap dietary aldehydes and ketones. The co-agents described in this subsection can accomplish this function because they bear primary amine groups or derivatives thereof. As large molecular weight molecules which are non-digestible they have the capacity to pass through the digestive tract, acting in effect as another form of dietary fiber. As defined in the original filing of U.S. patent application Ser. No. 07/660,561, filed Feb. 23, 1993, now abandoned, examples of these non-absorbable polyamine trapping substances may be divided into three classes; naturally occurring polyamine polysaccharides, chemical derivatives of naturally occurring polysaccharides, and synthetic polyamine polymers.

(a). Naturally Occurring Amine-Containing Polysaccharides

Any naturally occurring polysaccharide featuring beta-1,2, beta-1,3, beta-1,4 and/or beta-1,6 linkages which contains aminosugars may be regarded as a non-digestible, potentially active carbonyl trapping agent. The chitin class of biopolymers may be cited as an example of such an agent, having the general structure of poly-beta-(1→4)-N-acetyl-D-glucosamine. A form of microcrystalline chitin has been described in which some of the acetyl groups have been removed, revealing free amine groups (Austin and coworkers, 1981, pg. 750). Chitins obtained from different sources feature different degrees of amine deacetylation (Austin and coworkers, 1981, pg. 752).

(b). Chemical Derivatives of Naturally Occurring Polysaccharides

Various pretreatment procedures may be applied to naturally occurring polysaccharides prior to generation of chemical derivatives. Generation of microcrystalline polysaccharides is one example of such a pretreatment procedure. As applied to cellulose or chitin (Yalpani, 1988, pg. 389), this yields a colloidal processed form of polysaccharide featuring high porosity and enhanced susceptibility to chemical reactions. Generation of "microfibrillated" cellulose or chitin is another example of a pretreatment procedure which produces enhanced surface area, increased water retention capacity and enhanced chemical accessibility (Yalpani, 1988, pg. 390). Use of strong (>18%) sodium hydroxide is still another recognized pretreatment, or activation, procedure found to be helpful as a starting point for preparing chemical derivatives of polysaccharides (Yalpani, 1988, pg. 214).

(b)(1). Deacetylation of Naturally Occurring Polysaccharides.

A variety of polysaccharides have been identified which are rich in N-acetylated residues. Upon chemical deacetylation these carbohydrates yield high molecular weight derivatives bearing primary amine groups directly linked to sugar carbons, that is, no sidearm spacer units present.

(i) Chitosan. This is the deacylated form of chitin. As described in the *Merck Index* (1989, pg. 316) chitin is a cellulose-like biopolymer the composition of which consists mostly of N-acetyl-D-glucosamine residues covalvently linked by beta-1,4 bonds. Chemical deacylation removes acetate, generating primary amine groups still covalently bound to the polysaccharide. Chitosan has recognized uses in water treatment, in photographic emulsions, and in improving the dyability of synthetic fabrics and fibers. The free amine groups in this substance also give it chelating properties (Austin and coworkers, 1981).

(ii) Chondroitin sulfate. This is a mucopolysaccharide found commonly in mammalian tissue. It consists of repeating disaccharide units, each of which has a D-glucuronic acid residue beta-1,4 linked to an N-acetylchondrosine residue (*Merck Index*, 1989, pg. 344).

(iii) Hyaluronic acid. This mucopolysaccharide is also found commonly in mammalian tissues. It consists of glucuronic acid and glucosamine residues bound by beta-1,3 and beta-1,4 linkages (*Merck Index*, 1989, pp. 751–752).

(iv) Keratan sulfate. This mammalian glycosaminoglycan consists of a repeating disaccharide unit of a C-6 sulfated C-2 N-acetylated sugar residue and a galactose residue linked by beta-1,4 bonds (Yalpani, 1988, pp. 27–28).

(b)(2). Chemical Amination of Polysaccharides (i) 2-Amino-2-deoxy-cellulose. Cellulose can be aminated by a process of selective oxidation, oximation and subsequent reduction with lithium aluminum hydride (Yalpani, 1988, pp. 281–282).

(ii) Alternative amination procedures. Aminodeoxy polysaccharides can also be prepared via azide or hydrazide intermediates or by reductive amination using sodium cyanoborohydride (Yalpani, 1988, pg. 281). Besides being applied to cellulose, other non-digestible polysaccharides such as curdlan (Yalpani, 1988, pg. 22) may be aminated by such chemical procedures.

(iii) 3-Aminopropylcellulose. Reaction of cyanoethylcellulose with borane-tetrahydrofuran or borane-dimethyl sulfide complexes in tetrahydrofuran generates 3-aminopropylcellulose (Yalpani, 1988, pgs. 250 and 255). In this derivative each primary amine group is at the end of a three carbon sidearm.

(iv) Aminoethylcellulose. This chemical has been previously marketed as an anion exchange column chromatography resin (Sigma Chemical Co. catalog, February 1981) and used as such in protein purification studies (Fasold, 1975, pp 481–482).

(v) Other aminoalkyl-, amino(hydroxyalkyl)-, aminoalkyl-ether-, and amino(hydroxyalkyl)-ether-derivatives of cellulose, chitin and other naturally occurring non-digestible carbohydrates. Noting that the chemical methodology for producing such derivatives is documented in public domain literature, the biomedical application of such derivatives for therapeutic purposes described herein is also claimed. This would include:

aminoalkyl derivatives of the formula
$H_2N-(CH_2)_n$-[carbohydrate] where n=1–30, including alkyl isomers;

amino(hydroxyalkyl)-derivatives of the formula
$H_2N-(CH_2)_m-CHOH-(CH_2)_n$-[carbohydrate], where m=0–15 n=0–15;

aminoalkyl-ether-derivatives of the formula
$H_2N-(CH_2)_n-O$-[carbohydrate], where n=1–30 amino(hydroxyaklyl)-ether-der-ivatives of the formula
$H_2N-(CH_2)_m-CHOH-(CH_2)_n-O$-[carbohydrate], where m=0–15 n=0–15

(vi) Aminobenzyl-derivatives of cellulose, chitin or other naturally occurring non-digestible carbohydrates. As the aromatic amine group is a weaker base than its aliphatic counterpart, this class of non-absorbable amines should be less chemically active than amino- and aminoalkyl-derivatives described above. These derivatives are of the following general structures:

$H_2N-C_6H_4-(CH_2)_n$-[carbohydrate], $H_2N-CH_2-C_6H_4-(CH_2)_n$-[carbohydrate], $H_2N-C_6H_4-(CH_2)_n-O$-[carbohydrate] where n=0–30, and $H_2N-C_6H_4-(CH_2)_m-CHOH-(CH_2)_n-O$-[carbohydrate] where m=0–15 n=0–15

This includes p-, o- and m-benzene ring amino- and aminomethylisomers, and alkyl group isomers.

(vii) guanidine and aminoguanidine derivatives of cellulose, chitin or other naturally occurring non-absorbable carbohydrates selected from the group consisting of:

$H_2N-C(=NH)$-[carbohydrate];

$H_2N-C(=NH)-(CH_2)_n$-[carbohydrate], where n=1–10, including hydrocarbon isomers and hydroxylated derivatives thereof;

$H_2N-C(=NH)-O-(CH_2)_n$-[carbohydrate], where n=1–10, including hydrocarbon isomers, ether linkage isomers and hydroxylated derivatives thereof;

$H_2N-C(=NH)-NH$-[carbohydrate];

$H_2N-C(=NH)-NH-(CH_2)_n$-[carbohydrate], where n=1–10, including hydrocarbon isomers and hydroxylated derivatives thereof;

$H_2N-C(=NH)-NH-(CH_2)_n-O$-[carbohydrate], where n=1–10, including hydrocarbon isomers, ether linkage isomers and hydroxylated derivatives thereof;

$H_2N-C(=NH)-N=CH-(CH_2)_n$-[carbohydrate], where n=1–10, including hydrocarbon isomers and hydroxylated derivatives thereof;

$H_2N-C(=NH)-N=CH-(CH_2)_n-O$-[carbohydrate], where n=1–10, including hydrocarbon isomers and hydroxylated derivatives thereof;

$H_2N-NCH(=NH)-NH$-[carbohydrate];

$H_2N-NCH(=NH)-NH-(CH_2)_n$-[carbohydrate], where n=1–10, including hydrocarbon isomers and hydroxylated derivatives thereof;

$H_2N-NCH(=NH)-NH-(CH_2)_n-O$-[carbohydrate], where n=1–10, including hydrocarbon isomers, ether linkage isomers and hydroxylated derivatives thereof;

$H_2N-NCH(=NH)-N=CH-(CH_2)_n$-[carbohydrate], where n=1–10, including hydrocarbon isomers and hydroxylated derivatives thereof;

$H_2N-NCH(=NH)-N=CH-(CH_2)_n-O$-[carbohydrate], where n=1–10, including hydrocarbon isomers, ether linkage isomers and hydroxylated derivatives thereof;

$H_2N-C(=NH)-NH-NH$-[carbohydrate];

$H_2N-C(=NH)-NH-NH-(CH_2)_n$-[carbohydrate], where n=1–10, including hydrocarbon isomers and hydroxylated derivatives thereof;

$H_2N-C(=NH)-NH-NH-(CH_2)_n-O$-[carbohydrate], where n=1–10, including hydrocarbon isomers, ether linkage isomers and hydroxylated derivatives thereof;

$H_2N-C(=NH)-NH-N=CH-(CH_2)_n$-[carbohydrate], where n=1–10, including hydrocarbon isomers and hydroxylated derivatives thereof;

$H_2N-C(=NH)-NH-N=CH-(CH_2)_n-O$-[carbohydrate], where n=1–10, including hydrocarbon isomers, ether linkage isomers and hydroxylated derivatives thereof;

(b)(3). Aminated Sucrose Polyesters

Mixtures of fatty acid hexa-, hepta- and octaesters of sucrose, known as sucrose polyester, are not hydrolyzed by pancreatic lipase enzymes and are not absorbed in the intestine (Jandacek, 1984). It is proposed and claimed herein that primary amine, aminoguanidine and guanidine derivatives of sucrose polyesters may be of benefit in reduction of dietary carbonyl substances, analogous to the proposed action of other non-absorbable agents described herein. Such derivatives of sucrose polyesters would include structures in which the carbonyl trapping functional group is in the omega-, omega-1 or other isomeric position(s) within the fatty acyl chains, fatty acyl chains having more than one nitrogen functional group and fatty acyl chains having hydroxyl groups. Such aminated sucrose polyesters may be used in pure form as a dietary supplement, or may be prepared as a coating on a particulate carrier such as cellulose or styrene divinylbenzene copolymer resin.

(c). Synthetic Polyamine Polymers (c)(1). Synthetic polysaccharides consisting partly or entirely of aminosugars bound by beta-1,2, beta-1,3, beta-1,4 and/or beta-1,6 linkages may be regarded as non-absorbable potential carbonyl trapping agents.

(c)(2). Mixed polysaccharide polymeric derivatives. Primary amine, aminoalkyl (one to ten carbons per alkyl group), aminohydroxyalkyl (one to ten carbons per alkyl group and one to ten hydroxyl groups per alkyl group), aminoguanidine, aminoguanidinylalkyl (one to ten carbons per alkyl group), aminoalkylguanidinyl (one to ten carbons per alkyl group), guanidine, aminobenzene and aminoalkylbenzene (one to ten carbons per alkyl group) functional groups may be covalently attached to matrices such as epi-chlorohydrin copolymers of cellulose or chitin. Functional group spacer groups may include alkene as well as alkyl groups.

(c)(3). Non-polysaccharide polymeric derivatives. Primary amine, aminoalkyl (one to ten carbons per alkyl group), aminohydroxyalkyl (one to ten carbons per alkyl group and one to ten hydroxyl groups per alkyl group), aminoguanidine, aminoguanidinylalkyl (one to ten carbons per alkyl group), aminoalkylguanidinyl (one to ten carbons per alkyl group), guanidine, aminobenzene and aminoalkylbenzene (one to ten carbons per alkyl group) functional groups may be covalently attached to a wide variety of synthetic non-digestible polymers. Functional group spacer groups may include alkene as well as alkyl groups. Like their sugar-based counterparts, these agents should be capable of reacting with dietary carbonyl compounds. Nitrogen-containing functional groups may be covalently attached to synthetic supports such as polystyrene, styrene-divinylbenzene copolymer, polyvinyl alcohol and crosslinked derivatives thereof.

4. Example of the Invention of U.S. patent application Ser. No. 08/026,617 Used in a Clinical Trial Therapeutic Protocol:

Subject 1 is a male individual born in 1948 and having hereditary motor and sensory neuropathy. Family history indicates that this subject's family has the X-linked subvariety of the disease.

On Sep. 1, 1990 Subject 1 began taking three 100 mg tablets of p-aminobenzoic acid per day. This daily dosage consisted of single 100 mg tablets (Schiff Products, Moonachie, N.J.) taken one at a time approximately every eight hours. Also initiated at this time and taken three times per day: DL-methionine, 500 mg and vitamin E (as mix tocopherols in oil-based capsules), 200 I.U. His weight at the time was approximately 165 lbs. The daily dosage times were approximately 8:00 AM, 4:00 PM and 11:30 PM. This original low dosage of PABA was selected in part as a check to ensure no adverse immunologic reaction. Symptoms of allergic reaction such as bronchial constriction or skin rash were not observed. Actually, no clinical reaction to PABA was observed.

On Oct. 1, 1990 Subject 1 began taking a total of 600 mg PABA per day by doubling the original dosage noted above; 200 mg taken three times per day. Also taken with PABA: DL-methionine, 500 mg and vitamin E, 200 I.U.

On Jan. 1, 1991 Subject 1 began taking three 550 mg capsules of PABA (Solgar Co., Lynbrook, N.Y.) per day, one approximately every eight hours. DL-Methionine use was doubled to 1,000 mg every eight hours. Likewise, vitamin E deosage was doubled to 400 I.U. every eight hours. In addition, the following dietary supplements were initiated and taken once per day (4:00 PM):

pantothenic acid, 250 mg;
beta-carotene, 25,000 I.U.;
selenium (Osco, Oak Brook, Ill.), 50 µg;
vitamin $B_1$, 100 mg;
and one Osco brand "balanced B complex 50" tablet, each tablet consisting of:

| folic acid | 100 µg | vitamin $B_1$ | 50 mg |
| vitamin $B_2$ | 50 mg | niacin | 50 mg |
| vitamin $B_6$ | 50 mg | vitamin $B_{12}$ | 50 µg |
| biotin | 50 µg | pantothenic acid | 50 mg |

The ingredients as listed on the label are: "dicalcium phosphate, d-calcium pantothenate, pyridoxine hydrochloride, hydrogenated cottonseed oil, cellulose, niacinamide, rifoflavin, thiamine mono-nitrtate, stearic acid, modified cellulose gum, magnesium stearate, silica, resin, gum acacia, hydroxypropylcellulose, rice bran, yeast, para-aminobenzoic acid, alfalfa, watercress, parsley, lecithin, cyanocobalamin, folic acid, biotin." Except as noted above, the amounts of ingredients (such as PABA) were not stated.

On Feb. 24, 1991 Subject 1 began taking six 550 mg capsules of PABA per day, two every eight hours plus the dietary supplement combination initiated January 1st. DL-Methionine and vitamin E dosage were continued as initiated January 1st; 3,000 mg and 1,200 I.U. total daily, respectively. Dosage of additional dietary supplements was also continued as initiated January 1st, with the addition of 100 mg vitamin $B_1$ per day. Also, selenium daily dosage was reduced to 12 µg per day.

As of May 1st, 1991 consumption of pantothenic acid and vitamin $B_1$ were tripled to 250 mg 3× daily and 100 mg 3× daily, respectively, taken with PABA. Also initiated now, vitamin $B_6$, 100 mg taken 3× daily with PABA.

As of Jul. 1st, 1991 the methionine product was switched to "L-Methionine 500 mg Caps with Vitamin $B_6$" (Nature's Plus, Farmingdale, N.Y.). Each capsule has the free form of the L-amino acid and 50 mg vitamin $B_6$. This dose of vitamin $B_6$ is in addition to the 300 mg/day noted in the preceding paragraph.

As of Jul. 26, 1991 the vitamin E product was switched to "Natural Dry All E, 400 I.U." (Schiff Products, Moonachie, N.J.). One of these dry powder capsules is taken 3× daily with PABA, as before.

As of Aug. 7, 1991 daily doses of PABA, methionine and vitamin E were increased by 50%. Thus starting at this time, three 550 mg PABA capsules, three 500 mg methionine capsules, one 400 I.U. dry vitamin E and a 200 I.U. dry vitamin E capsule were taken at a time, three times per day. Daily totals of these agents were now: PABA, 4.95 gm; methionine, 4.5 gm: and vitamin E, 1,800 I.U. Other agents were taken as before.

As of Nov. 22, 1991 the daily dose of PABA was increased. Thus starting at this time, four 550 mg PABA capsules were taken at a time, three times per day. Daily total of PABA was now 6.6 gm. Other agents were taken as before.

Nerve Conduction Studies on Subject 1:

On Jun. 20, 1988 Subject 1 participated in a nerve conduction research study at the National Institutes of Health. Nerve conduction data was recorded from the left median and ulnar nerves, which included conduction velocity, amplitude and distal latency for each nerve. On May 6, 1992 Subject 1 was tested again at the office of a neurologist in Bryn Mawr, Pa. The results of these studies may be summarized as follows.

|  | Conduction velocity meters/sec | Amplitude mV | Latency msec |
| --- | --- | --- | --- |
| Median Nerve |  |  |  |
| 6/20/88 study | 28 | 0.4 | 12.4 |
| 5/6/92 study | 28.2 | 0.4 | 13.1 |
| Ulnar Nerve |  |  |  |
| 6/20/88 study | 29 | 1.3 | 13.8 |
| 5/6/92 study | 31.8 | 2.4 | 13.1 |

These data indicate that there was little change in the neurophysiological status of the left median nerve during the course of the experimental therapeutic drug trial; conduction velocity and amplitude remained unchanged, while the distal latency increased (that is, worsened) by six percent. However, data on the left ulnar nerve document an improvement in neurophysiological status; conduction velocity improved by ten percent, amplitude improved by eighty-five percent and distal latency improved by five percent.

This experimental drug trial involved a step-by-step increase in dosages over an extended period. Dosages of PABA, the primary agent were slowly increased from September, 1990 to November, 1991. The final PABA dosage level (6.6 gm/day) was maintained from November, 1991 to May, 1992, a period of approximately six and one half months. During this study period the left ulnar nerve, which was more intact to begin with, began to show improvement in neurophysiological status. This slow improvement in nerve conduction status is in accord with what is known of the ability of peripheral nerves to regenerate axons. As Bradley (1990) has noted:

> ... it may take as long as 18 months before regenerating axons reach the distal denervated muscles where the site of the lesion lay in proximal nerve roots or plexuses. In neuronopathies, where cell death has occurred, any degree of recovery can only occur by peripheral sprouting from axons of surviving neurons. This also appears to be a relatively slow process. Hence, therapeutic trials must extend for long enough to ensure that the slow biological reparative processes can be detected.

The available findings on the left ulnar nerve of Subject 1 indicate that conduction velocity has improved, the number of detectable axonal fibers has almost doubled (improved amplitude) and a modest increase in re-innervation of the distal muscle group has begun to occur (improved latency).

5. Use of the Invention of U.S. patent application Ser. No. 08/026,617, filed Feb. 23, 1993, now abandoned, in Combination with Known Medicaments As summarized above, it is evident that presently available pharmaceutical technology for treatment of the diseases addressed herein is almost entirely symptomatic, as well as temporary and of partial clinical benefit, at best. The dosages of any of the known medicaments discussed herein, except those which are still the subjects of preliminary laboratory studies, are well known to those skilled in the art. Significant adverse side effects accompany many of these treatments, which limit their use. The present invention defines the use of previously recognized technology in combination with the invention originally described in U.S. patent application Ser. No. 07/660,561, filed Feb. 21, 1991, now abandoned, so as to achieve greater clinical effectiveness in treatment of these diseases. In using the therapeutic technology defined herein, physicians may achieve in some cases the clinical benefits of previously recognized drugs while using lower dosage levels, thus minimizing adverse side effects. Within the context of the present invention, it is important to note the documentation provided by Flood and coworkers (1988). Their findings indicate that when drugs are used in combination they may provide beneficial effect at reduced dosages which are ineffective when drugs are administered alone. This approach may permit wider and more effective use of previously recognized drug technology. It is acknowledged herein that for many of the previously known medicaments the optimum dosage must be determined on an individualized basis, and may be below or above the dosage range generally recognized for public use. It is to be understood that in particular cases it may be desirable to go beyond the dosage ranges noted below. Except where stated otherwise, the drugs listed in the following examples are to be administered orally.

EXAMPLE 1

Clinical treatment of Parkinson's disease may be improved by use of the invention originally disclosed in U.S. patent application Ser. No. 07/660,561, filed Feb. 21, 1991, now abandoned, in combination with known medicaments, including co-agent use of:

(a) carbidopa and levodopa compositions (Sinemet tablets and Sinemet CR controlled release tablets, Du Pont Pharmaceuticals), dosage range from 30 mg carbidopa and 300 mg levodopa daily to 600 mg carbidopa and 2,400 mg levodopa daily;

(b) dopamine agonists such as
  bromocriptine mesylate (Parlodel SnapTabs and capsules, Sandoz Pharmaceuticals), dosage range from 1.25 to 140 mg daily;
  pergolide mesylate (Permaxm, Lilly), dosage range from 0.05 mg daily to 5 mg daily;
  (+)-4-propyl-9-hydroxynaphthoxazine, dosage range from 1 µg/kg/day to 0.3 mg/kg/day;
  apomorphine, dosage range from 0.1 mg/kg/day to 2 mg/kg/day; and
  ciladopa, dosage range from 0.5 mg/kg/day to 20 mg/kg/day;

(c) anticholinergic medications such as
  benztropine mesylate (Cogentin, Merck & Co.), dosage range from 0.5 mg daily to 6 mg daily; and
  biperiden, dosage range from 0.5 mg daily to 6 mg daily;

(d) antihistamines such as
  orphenadrine citrate (Norflex sustained-release tablets, Norgesic tablets and Norgesic Forte tablets, 3M Pharmaceuticals), dosage range from 100 mg daily to 200 mg daily;

(e) tricyclic antidepressants such as
  amitriptyline HCl (Elavil, Stuart), dosage range from 50 mg daily to 300 mg daily;
  amitriptyline HCl/perphenazine combinations (Etrafon, Schering), dosage range from 4 mg perphenazine and 50 mg amitriptyline daily to 16 mg perphenazine and 100 mg amitriptyline daily;

amitriptyline/chlordiazepoxide combinations (Limbitrol, Roche Products), dosage range from 5 mg chlordiazepoxide and 12.5 mg amitriptyline daily to 60 mg chlordiazepoxide and 150 mg amitriptyline daily;

nortriptyline HCl (Pamelor, Sandoz Pharmaceutical), dosage range from 25 mg daily to 150 mg daily;

imipramine, dosage range from 2 mg daily to 150 mg daily; and doxepin, dosage range from 2 mg daily to 150 mg daily;

(f) serotonin reuptake inhibitor antidepressants such as
fluoxetine HCl (Prozac, Dista), dosage range from 20 mg daily to 80 mg daily; and sertraline (Zoloft, Pratt Pharmaceuticals), dosage range from 50 mg daily to 200 mg daily;

(g) beta blocker agents such as
propranolol HCl (Inderal, Wyeth-Ayerst Laboratories), dosage range from 30 mg daily to 640 mg daily;

pindolol (Visken, Sandoz Pharmaceuticals), dosage range from 10 mg daily to 60 mg daily;

metoprolol tartrate (Lopressor, Geigy), dosage range from 100 mg daily to 450 mg daily;

metoprolol succinate (Toprol XL, Astra), dosage range from 50 mg daily to 400 mg daily; and atenolol (Tenormin, ICI Pharma), dosage range from 50 mg daily to 200 mg daily;

(h) selegiline (Eldepryl, Somerset), dosage range from 5 mg daily to 10 mg daily;

(i) selegiline in combination with tocopherol, dosage range from 5 mg selegiline and 500 I. U. tocopherol daily to 10 mg selegiline and 3500 I. U. tocopherol daily;

(j) D-cycloserine with or without a cholinesterase inhibitor co-agent, dosage range from 0.1 mg/kg daily to 15 mg/kg daily;

(k) neurotransmission enhancer drugs such as
lisuride, dosage range from 0.1 mg daily to 2 mg daily;

(l) peripheral decarboxylase inhibitors other than carbidopa such as
benserazide used in combination with levodopa, dosage range from 25 mg benserazide and 500 mg levodopa daily to 200 mg benserazide and 2,400 mg levodopa daily;

(m) N-methyl-D-aspartate glutamate receptor antagonists administered orally, intramuscularly, subcutaneously or intraveneously such as
trihexyphenidyl (Artane, Lederle), dosage range from 0.1 mg daily to 20 mg daily;

ethopropazine (Paridol), dosage range from 10 mg daily to 400 mg daily;

procyclidine (Kemadrin, Burroughs Wellcome), dosage range from 1 mg daily to 40 mg daily;

diphenhydramine (Benadryl, Parke-Davis), dosage range from 5 mg daily to 200 mg daily;

dizocilpine (Neurogard, Merck Sharp & Dohme), dosage range from 0.1 µg/kg daily to 10 mg/kg daily;

amantadine (Symmetrel, Du Pont Multi-Source Products), dosage range from 10 mg daily to 400 mg daily;

memantine, dosage range from 10 mg daily to 400 mg daily; and milacemide, dosage range from 50 mg daily to 2.5 grams daily;

(n) tacrine (Cognex, Warner-Lambert), dosage range from 5 mg daily to 200 mg daily, optionally with phosphatidylcholine co-agent, dosage range from zero to 15 gm daily;

(o) (±)-9-amino-1,2,3,4-tetrahydroacridin-1-ol, dosage range from 2 mg daily to 200 mg daily;

(p) lazabemide (Hoffmann-La Roche), dosage range from 10 mg daily to 200 mg daily;

(q) tiapride, dosage range from 1 mg daily to 400 mg daily; and (r) antioxidant agents which may be used in combination such as
ascorbic acid, dosage range from 1 mg daily to 60 mg daily;

alpha-tocopherol, dosage range from 100 I. U. daily to 3,500 I. U. daily;

N-acetylcysteine, dosage range from 100 mg daily to 1 gm daily;

beta-carotene, dosage range from 20 mg daily to 300 mg daily;

penicillamine, dosage range from 25 mg daily to 2 gm daily; and cysteamine, dosage range from 200 mg daily to 4 gm daily.

EXAMPLE 2

Clinical treatment of Alzheimer's disease may be improved by use of the invention originally disclosed in U.S. patent application Ser. No. 07/660,561, filed Feb. 21, 1991, now abandoned, in combination with known medicaments, including co-agent use of:

(a) vasodilator or other nootropic direct brain metabolic enhancer drugs such as
idebenone, dosage range from 5 mg/kg daily to 150 mg/kg daily;

propentophylline, intravenous, intramuscular, subcutaneous or oral dosage range from 50 mg daily to 3 grams daily;

pentoxifylline, dosage range from 50 mg daily to 3 grams daily;

citicoline, dosage range from 50 mg daily to 5 grams daily;

ebiratide, subcutaneous dosage range from 3 µg/kg daily to 1 mg/kg daily;

vinpocetine (Cavinton, Chemical Works of Gedeon Richter, Ltd.), intravenous, intramuscular, subcutaneous or oral dosage range from 5 mg/kg daily to 300 mg/kg daily;

bromvincamine, dosage range from 25 mg daily to 3 grams daily;

cyclandelate, dosage range from 25 mg daily to 3 grams daily;

isoxsuprene, dosage range from 25 mg daily to 3 grams daily;

nafronyl, dosage range from 25 mg daily to 3 grams daily;

papaverine, dosage range from 25 mg daily to 3 grams daily;

suloctidil, dosage range from 25 mg daily to 3 grams daily;

vinburnine, dosage range from 25 mg daily to 3 grams daily;

vincamine, dosage range from 25 mg daily to 3 grams daily;

vindeburnol, dosage range from 25 mg daily to 3 grams daily;

naloxone, intravenous, intramuscular, subcutaneous or oral dosage range from 5 mg daily to 300 mg daily;

ethyl 5-isopropyloxy-4-methyl-beta-carboline-3-carboxylate, intravenous, intramuscular, subcutaneous or oral dosage range from 2 mg/kg daily to 100 mg/kg daily;

N'-methyl-beta-carboline-3-carboxamide, intravenous, intramuscular, subcutaneous or oral dosage range from 2 mg/kg daily to 100 mg/kg daily;

methyl 6,7-dimethoxy-4-ethyl-beta-carboline-3-carboxylate, intravenous, intramuscular, subcutaneous or oral dosage range from 0.1 mg/kg daily to 10 mg/kg daily;

ethyl 5-methoxy-4-ethyl-beta-carboline-3-carboxylate, intravenous, intramuscular, subcutaneous or oral dosage range from 1 mg/kg daily to 30 mg/kg daily;

ifenprodil tartrate, dosage range from 0.5 mg/kg daily to 120 mg/kg daily;

piracetam, dosage range from 1 mg daily to 100 mg daily;

aniracetam, dosage range from 50 mg/kg daily to 1 gram/kg daily;

pyroglutamic acid, intravenous, intramuscular, subcutaneous or oral dosage range from 100 mg/kg daily to 5 grams/kg daily;

tenilsetam, dosage range from 10 mg daily (or alternate day) to 1 gram daily (or alternate day), or from 25 mg once a week to 1 gram once a week;

pramiracetam, dosage range from 50 mg/kg daily to 8 grams/kg daily;

oxiracetam, dosage range from 200 mg daily to 2 grams daily;

rolziracetam, intravenous, intramuscular, subcutaneous or oral dosage range from 1 mg daily to 1 gram daily;

razobazam, intravenous, intramuscular, subcutaneous or oral dosage range from 0.1 mg/kg daily to 25 mg/kg daily;

exifone, intravenous, intramuscular, subcutaneous or oral dosage range from 1 mg daily to 1 gram daily;

rolipram, intravenous, intramuscular, subcutaneous or oral dosage range from 1 mg daily to 1 gram daily;

sabeluzole, dosage range from 2 mg daily to 40 mg daily;

nimodipine (Nimotop, Miles Pharmaceutical), dosage range from 300 mg daily to 3.6 gm daily;

flunarizine, dosage range from 2 mg daily to 100 mg daily;

nicergoline (Sermion), intravenous, intramuscular, subcutaneous or oral dosage range from 6 mg daily to 10 grams daily;

phosphatidylserine, intravenous or oral dosage range from 1 mg/kg daily to 250 mg/kg daily;

etiracetam, dosage range from 50 mg/kg daily to 8 grams/kg daily;

dupracetam, intravenous, intramuscular, subcutaneous or oral dosage range from 1 mg daily to 1 gram daily; and ergoloid mesylates (Hydergine, Sandoz Pharmaceuticals), dosage range from 0.5 mg daily to 40 mg daily;

(b) neurotransmission enhancer drugs such as amantadine (Symmetrel, Du Pont Multi-Source Products), dosage range from 10 mg daily to 400 mg daily;

calcium hopantenate, dosage range from 100 mg daily to 4 grams daily;

lisuride, dosage range from 0.1 mg daily to 2 mg daily; and indeloxazine, dosage range from 50 mg daily to 1.5 grams daily;

(c) tiapride, dosage range from 1 mg daily to 400 mg daily;

(d) psychotherapeutic drugs such as haloperidol (Haldol, McNeil Pharmaceutical), dosage range from 0.2 mg daily to 15 mg daily;

bromperidol, dosage range from 20 µg/kg daily to 0.25 mg/kg daily;

thioridazine (Mellaril, Sandoz Pharmaceutical), dosage range from 10 mg daily to 800 mg daily;

thiothixene (Navane, Roerig), dosage range from 2 mg daily to 60 mg daily;

fluphenazine (Prolixin, Apothecon), dosage range from 0.2 mg daily to 40 mg daily;

perphenazine in amitriptyline/perphenazine combinations (Etrafon, Schering), dosage range from 4 mg perphenazine and 50 mg amitriptyline daily to 16 mg perphenazine and 100 mg amitriptyline daily; and molindone (Moban, Du Pont Multi-Source Products), dosage range from 3 mg daily to 225 mg daily;

(e) acetylcholinesterase inhibitors such as physostigmine (Antilirium Injectable, Forest Pharmaceuticals), oral dosage range from 0.1 mg daily to 20 mg daily, or intravenous, intramuscular or subcutaneous dosage range from 5 µg daily to 3 mg daily, optionally with phosphatidylcholine co-agent, oral dosage range from zero to 15 gm daily;

heptylphysostigmine, dosage range from 1 mg daily to 1 gram daily;

tacrine (Cognex, Warner-Lambert), dosage range from 5 mg daily to 200 mg daily, optionally with phosphatidylcholine co-agent, dosage range from zero to 15 gm daily;

(±)-9-amino-1,2,3,4-tetrahydroacridin-1-ol, dosage range from 2 mg daily to 200 mg daily;

metrifonate, intramuscular, intravenous, subcutaneous or oral dosage range from 0.1 mg/kg daily to 125 mg/kg daily;

velnacrine (Mentane, Hoechst-Roussel), dosage range from 10 mg daily to 350 mg daily;

phenylmethylsulfonyl fluoride, intravenous, subcutaneous, intramuscular or oral dosage range from 5 mg/kg daily to 60 mg/kg daily;

methanesulfonyl fluoride, intravenous, intramuscular, subcutaneous or oral dosage range from 5 mg/kg daily to 350 mg/kg daily;

huperzine A, intramuscular, intravenous, subcutaneous or oral dosage range from 10 ug/kg daily to 1 mg/kg daily;

huperzine B, intramuscular, intravenous, subcutaneous or oral dosage range from 10 µg/kg daily to 1 mg/kg daily;

edrophonium chloride (Hoffman LaRoche), intravenous, intramuscular, subcutaneous or oral dosage range from 2 mg daily to 400 mg daily;

galanthamine, intravenous, intramuscular, subcutaneous or oral dosage range from 5 mg daily to 100 mg daily; and miotine, intravenous, intramuscular, subcutaneous or oral dosage range from 2 mg daily to 400 mg daily;

(f) calcium channel blocker agents such as diltiazem (Cardizem or Cardizem SR), dosage range from 10 mg daily to 360 mg daily;

verapamil (Calan or Calan SR), dosage range from 10 mg daily to 480 mg daily;

nifedipine (Procardia), dosage range from 3 mg daily to 180 mg daily;

nifedipine (Procardia XL), dosage range from 3 mg daily to 90 mg daily;

nicardipine (Cardene), dosage range from 6 mg daily to 120 mg daily;

isradipine (DynaCirc), dosage range from 0.5 mg daily to 20 mg daily;

amlodipine (Norvasc, Pfizer Labs Division), dosage range from 0.5 mg daily to 10 mg daily; and felodipine (Plendil, Merck & Co.), dosage range from 0.5 mg daily to 20 mg daily;

(g) biogenic amines and agents related thereto such as
clonidine (Catapres, Boehringer Ingelheim), dosage range from 0.25 mg daily to 2.4 mg daily;

guanfacine (Tenex, Robins), dosage range from 0.25 mg daily to 3 mg daily;

alaproclate, dosage range from 0.25 mg daily to 3 mg daily;

fipexide, dosage range from 0.25 mg daily to 3 mg daily;

zimeldine, dosage range from 0.25 mg daily to 3 mg daily; and citalopram, dosage range from 0.25 mg daily to 3 mg daily;

(h) antirage drugs such as
propranolol (Inderal, Wyeth-Ayerst Laboratories), dosage range from 30 mg daily to 640 mg daily;

carbamazepine (Tegretol, Geigy), dosage range from 40 mg daily to 1.6 gm daily; and fluoxetine (Prozac Pulvules, Dista), dosage range from 20 mg daily to 80 mg daily;

(i) minor tranquilizers such as benzodiazepine agents including diazepam (Valium, Roche Products), dosage range from 0.5 mg daily to 40 mg daily;

lorazepam (Ativan, Wyeth-Ayerst Laboratories), dosage range from 0.5 mg daily to 10 mg daily;

prazepam (Centrax, Parke-Davis), dosage range from 5 mg daily to 60 mg daily;

chlordiazepoxide (Libritabs, Roche Products), dosage range from 5 mg daily to 300 mg daily;

chlordiazepoxide/clidinium combination (Librax, Roche Products), dosage range from 5 mg chlordiazepoxide and 2.5 mg clidinium daily to 20 mg chlordiazepoxide and 10 mg clidinium daily;

chlordiazepoxide/amitriptyline combination (Limbitrol DS, Roche Products), dosage range from 10 mg chlordiazepoxide and 25 mg daily to 60 mg chlordiazepoxide and 150 mg amitriptyline daily;

chlordiazepoxide/esterified estrogen combination (Menrium, Roche Products), dosage range from 5 mg chlordiazepoxide and 0.2 mg esterified estrogen daily to 30 mg chlordiazepoxide and 1.2 mg esterified estrogen daily;

oxazepam (Serax, Wyeth-Ayerst), dosage range from 10 mg daily to 120 mg daily; and clorazepate dipotassium (Tranxene, Abbott Laboratories), dosage range from 3.75 mg daily to 60 mg daily;

(j) angiotensin-converting enzyme inhibitors such as
captopril (Capoten, Squibb), dosage range from 5 mg daily to 300 mg daily;

captopril in combination with hydrochlorothiazide (Capozide, Squibb), dosage range from 5 mg captopril and 3 mg hydrochlorothiazide daily to 150 mg captopril and 50 mg hydrochlorothiazide daily;

enalapril maleate (Vasotec, Merck & Co.), dosage range from 0.5 mg daily to 100 mg daily;

enalaprilat, dosage range from 0.5 mg daily to 100 mg daily;

enalapril maleate/hydrochlorothiazide combination (Vaseretic, Merck & Co.), dosage range from 2.5 mg enalapril maleate and 6.25 mg hydrochlorothiazide daily to 20 mg enalapril maleate and 50 mg hydrochlorothiazide daily;

fosinopril (Monopril, Mead Johnson Pharmaceuticals), dosage range from 2 mg daily to 60 mg daily;

lisinopril (Zestril, Stuart), dosage range from 1 mg daily to 40 mg daily;

ramipril (Altace, Hoechst-Roussel), dosage range from 0.5 mg daily to 10 mg daily;

epi-captopril, dosage range from 1 mg daily to 300 mg daily;

alacepril, dosage range from 5 mg daily to 300 mg daily;

quinapril, dosage range from 0.5 mg daily to 40 mg daily;

perindopril, dosage range from 0.2 mg daily to 40 mg daily;

delapril, dosage range from 4 mg daily to 1.5 grams daily;

cilazapril, dosage range from 0.2 mg daily to 40 mg daily;

pivalopril, dosage range from 2 mg daily to 250 mg daily;

rentiapril, dosage range from 1 mg daily to 150 mg daily;

zofenopril, dosage range from 1 mg daily to 150 mg daily; and zofenoprilat, dosage range from 1 mg daily to 150 mg daily;

(k) agents which may enhance acetylcholine synthesis, storage or release such as
phosphatidylcholine, dosage range from 1 gm daily to 15 gm daily;

4-aminopyridine, intravenous, intramuscular, subcutaneous or oral dosage range from 0.25 mg/kg daily to 10 mg/kg daily;

3,4-diaminopyridine, intravenous, intramuscular, subcutaneous or oral dosage range from 50 μg daily to 100 mg daily;

choline chloride, dosage range from 500 mg daily to 30 grams daily;

choline bitartrate, dosage range from 500 mg daily to 30 grams daily;

bifemelane, dosage range from 1 mg/kg daily to 1.2 grams/kg daily;

vesamicol, dosage range from 50 μg/kg daily to 500 mg/kg daily;

secoverine, dosage range from 50 μg/kg daily to 500 mg/kg daily;

tetraphenylurea, dosage range from 50 μg/kg daily to 500 mg/kg daily; and nicotinamide, dosage range from 1 mg/kg daily to 500 mg/kg daily;

(l) postsynaptic receptor agonists such as
arecoline, intravenous, intramuscular, subcutaneous or oral dosage range from 2 mg daily to 25 mg daily;

oxotremorine, intravenous, intramuscular, subcutaneous or oral dosage range from 1 μg/kg daily to 0.2 mg/kg daily;

ethyl nipecotate, intravenous, intramuscular, subcutaneous or oral dosage range from 2 mg daily to 250 mg daily;

bethanechol (Urecholine, Merck & Co.), dosage range from 5 mg daily to 200 mg daily; and levacecarnine (acetyl-L-carnitine or Alcar, Sigma-Tau), dosage range from 500 mg daily to 5 grams daily;

(m) ganglioside GM$_1$, intravenous, intramuscular or subcutaneous dosage range from 20 mg daily to 200 mg daily;

(n) mixed cow brain gangliosides (Cronassial, Fidia Pharmaceutical, marketed in several countries in Western Europe, South America and the Far East), intravenous, intramuscular or subcutaneous dosage range from 20 mg daily to 200 mg per day;

(o) specific monoamine oxidase-A inhibitors such as moclobemide (Aurorix, Hoffmann-La Roche), dosage range from 50 mg daily to 600 mg daily;

(p) N-methyl-D-aspartate glutamate receptor antagonists administered orally, intravenously, intramuscularly or subcutaneously such as milacemide, dosage range from 50 mg daily to 2.5 grams daily;

trihexyphenidyl (Artane, Lederle), dosage range from 0.1 mg daily to 20 mg daily;

ethopropazine (Paridol), dosage range from 10 mg daily to 400 mg daily;

procyclidine (Kemadrin, Burroughs Wellcome), dosage range from 1 mg daily to 40 mg daily;

diphenhydramine (Benadryl, Parke-Davis), dosage range from 5 mg daily to 200 mg daily;

dizocilpine (Neurogard, Merck Sharp a Dohme), dosage range from 0.1 μg/kg daily to 10 mg/kg daily;

amantadine (Symmetrel, Du Pont Multi-Source Products), dosage range from 10 mg daily to 400 mg daily; and memantine, dosage range from 10 mg daily to 400 mg daily;

(q) nonsteroidal anti-inflammatory agents such as those recognized for treatment of rheumatoid arthritis, including flurbiprofen (Ansaid, Upjohn), dosage range from 20 mg daily to 300 mg daily;

aspirin (Arthritis Pain Formula, Whitehall Laboratories), dosage range from 250 mg aspirin daily to 4 gm daily;

mesalamine (Asacol, Procter & Gamble Pharmaceuticals), dosage range from 250 mg daily to 2.4 gm daily;

phenylbutazone (Butazolidin, Geigy), dosage range from 30 mg daily to 400 mg daily;

sulindac (Clinoril, Merck & Co), dosage range from 40 mg daily to 400 mg daily;

penicillamine (Cuprimine, Merck & Co.), dosage range from 25 mg daily to 2 gm daily;

oxaprozin (Daypro, Searle), dosage range from 25 mg daily to 2 gm daily;

salsalate (Disalcid, 3M Pharmaceuticals), dosage range from 300 mg daily to 3 gm daily;

diflunisal (Dolobid, Merck a Co.), dosage range from 100 mg daily to 1.5 gm daily;

piroxicam (Feldene, Pfizer Labs Division), dosage range from 2 mg daily to 20 mg daily;

indomethacin (Indocin, Merck & Co.), dosage range from 10 mg daily to 200 mg daily;

etodolac (Lodine, Wyeth-Ayerst Laboratories), dosage range from 100 mg daily to 1.2 gm daily;

meclofenamate sodium (Meclomen, Parke-Davis), dosage range from 20 mg daily to 400 mg daily;

ibuprofen (Motrin, Upjohn), dosage range from 100 mg daily to 3.2 gm daily;

fenoprofen calcium (Nalfon, Dista), dosage range from 100 mg daily to 3.2 gm;

naproxen sodium (Anaprox, Syntax), dosage range from 50 mg daily to 1.65 gm daily;

naproxen (Naprosyn, Syntex), dosage range from 50 mg daily to 1.5 gm daily;

ketoprofen (Orudis, Wyeth-Ayerst), dosage range from 15 mg daily to 300 mg daily;

mefenamic acid (Ponstel, Parke-Davis), dosage range from 150 mg daily to 1.5 gm daily;

nabumetone (Relafen, SmithKline Beecham), dosage range from 100 mg daily to 2 gm daily;

auranofin (Ridaura, SmithKline Beecham), dosage range from 1 mg daily to 9 mg daily;

tolmetin sodium (Tolectin, McNeil Pharmaceutical), dosage range from 100 mg daily to 1.8 gm daily;

ketorolac tromethamine (Toradol, Syntex Laboratories), dosage range from 4 mg daily to 40 mg daily;

diclofenac sodium (Voltaren, Geigy), dosage range from 10 mg daily to 200 mg daily; and deferoxamine mesylate (Desferal, CIBA Pharmaceutical), intravenous, intramuscular or subcutaneous dosage range from 100 mg daily to 2 gm daily;

(r) selegiline (Eldepryl, Somerset), dosage range from 5 mg daily to 10 mg daily;

(s) thiamine, dosage range from 500 mg daily to 3 gm daily;

(t) anfacine, intravenous, intramuscular, subcutaneous or oral dosage range from 1 mg/kg daily to 350 mg/kg daily;

(u) sulbutiamine (Arcalion, Laboratories Servier), dosage range from 1 mg/kg daily to 350 mg/kg daily;

(v) antioxidant agents which may be used in combination such as ascorbic acid, dosage range from 1 mg daily to 60 mg daily;

alpha-tocopherol, dosage range from 100 I. U. daily to 3,500 I. U. daily;

N-acetylcysteine, dosage range from 100 mg daily to 1 gm daily;

beta-carotene, dosage range from 20 mg daily to 300 mg daily;

penicillamine, dosage range from 25 mg daily to 2 gm daily;

cysteamine, dosage range from 200 mg daily to 4 gm daily; and deferoxamine mesylate (Desferal, CIBA Pharmaceutical), intravenous, intramuscular or subcutaneous dosage range from 100 mg daily to 2 gm daily;

(w) specific monoamine oxidase-B inhibitors such as lazabemide (Hoffmann-La Roche), dosage range from 10 mg daily to 200 mg daily;

(x) linopirdine (Aviva, DuPont Merck), dosage range from 1 mg daily to 500 mg daily;

(y) D-cycloserine, dosage range from 0.1 mg/kg daily to 15 mg/kg daily; and (z) serotonergic receptor antagonists such as ketanserin (Ketan, Janssen Pharmaceutica), intravenous, intramuscular, subcutaneous or oral dosage range from 0.1 mg/kg daily to 20 mg/kg daily; and mianserin (Mian, Organon International), intravenous, intramuscular, subcutaneous or oral dosage range from 0.1 mg/kg daily to 20 mg/kg daily.

EXAMPLE 3

Clinical treatment of various forms of diabetes may be improved by use of the invention originally disclosed in U.S.

patent application Ser. No. 07/660,561, filed Feb. 21, 1991, now abandoned, in combination with known medicaments, including co-agent use of:

(a) various insulin derivatives and compositions such as
  human isophane insulin suspension (Mixtard Human 70/30, Novo Nordisk), available in 100 unit/ml vials, dosage as per the *Physician's Desk Reference* [Dowd, Ala., 1993, pg. 1684]);
  human zinc suspension insulin (Novolin L, Novo Nordisk), available in 100 unit/ml vials, dosage as per the *Physician's Desk Reference* [Dowd, Ala., 1993, pgs. 1683–1684]); and
  human insulin (HUMULIN compositions, Eli Lilly, available in seven formulations for intravenous use, dosage as per the *Physician's Desk Reference* [Dowd, Ala., 1993, pgs. 1301–1308]);

(b) various oral sulfanilamide derivative hypoglycemic agents such as
  tolbutamide (Orinase, Upjohn), dosage range from 100 mg daily to 3 gm daily;
  acetohexamide, dosage range from 25 mg daily to 1.5 gm daily;
  tolazamide (Tolinase, Upjohn), dosage range from 10 mg daily to 1 gm daily;
  chlorpropamide (Diabinase, Pfizer Labs Division), dosage range from 10 mg daily to 500 mg daily;
  glipizide (Glucotrol, Pratt Pharmaceuticals), dosage range from 1 mg daily to 40 mg daily; and
  glyburide (Micronase, Upjohn), dosage range from 0.5 mg daily to 20 mg daily;

(c) angiotensin-converting enzyme inhibitors such as
  captopril (Capoten, Squibb), dosage range from 10 mg daily to 450 mg daily;
  captopril in combination with hydrochlorothiazide (Capozide, Squibb), dosage range from 6.25 mg captopril and 3.75 mg hydrochlorothiazide daily to 150 mg captopril and 50 mg hydrochlorothiazide daily;
  enalapril maleate (Vasotec, Merck & Co.), dosage range from 1 mg daily to 40 mg daily;
  enalapril maleate/hydrochlorothiazide combination (Vaseretic, Merck & Co.), dosage range from 2.5 mg enalapril and 6.25 mg hydrochlorothiazide daily to 20 mg enalapril and 50 mg hydrochlorothiazide daily;
  epi-captopril, dosage range from 1 mg daily to 300 mg daily; and
  zofenoprilat, dosage range from 1 mg daily to 150 mg daily;

(d) anti-hyperlipidemia agents such as
  fibric acid derivatives including
    gemfibrozil (Lopid, Parke-Davis), dosage range from 100 mg daily to 1.2 gm daily;
    clofibrate (Atromid-S, Wyeth-Ayerst), dosage range from 20 mg daily to 2 gm daily;
    bezafibrate, dosage range from 100 mg daily to 1.3 grams daily;
    fenofibrate, dosage range from 40 mg daily to 500 mg daily;
    metformin, dosage range from 100 mg daily to 4 grams daily;
    guar gum, dosage range from 2 grams daily to 20 grams daily;
  3-hydroxy-3-methyl-glutaryl-CoA reductase inhibitors such as
    lovastatin (Mevacor, Merck & Co.), dosage range from 2 mg daily to 80 mg daily;
    pravastatin sodium (Pravachol, Squibb), dosage range from 1 mg daily to 40 mg daily; and
    simvastatin (Zocor, Merck & Co.), dosage range from 1 mg daily to 40 mg daily;
  dextrothyroxine sodium (Choloxin, Boots-Flint), dosage range from 0.25 mg daily to 8 mg daily;
  probucol (Lorelco, Marion Merrell Dow), dosage range from 100 mg daily to 1 gm daily;
  nicotinic acid (Nicolar, Rhone-Poulenc Rorer), dosage range from 500 mg daily to 6 gm daily;
  acipimox, dosage range from 1 mg/kg daily to 500 mg/kg daily;
  or bile acid sequestrants such as
    cholestyramine resin (Questran Light, Bristol Laboratories), dosage range from 400 mg anhydrous cholestyramine resin daily to 20 gm anhydrous cholestyramine resin daily; and
    colestipol (Colestid, Upjohn), dosage range from 500 mg daily to 30 gm daily;

(e) antioxidants such as
  probucol (Lorelco, Marion Merrell Dow), dosage range from 100 mg daily to 1 gm daily;
  prostaglandin $B_1$ oligomers (also known as polymeric 15-keto prostaglandin B or $PGB_x$), intravenous, intramuscular, subcutaneous or oral dosage range from 5 mg/kg daily to 400 mg/kg daily;
  2-aminomethyl-4-tert-butyl-6-iodophenol, dosage range from 0.5 mg/kg daily to 600 mg/kg daily;
  2-aminomethyl-4-tert-butyl-6-propionylphenol, dosage range from 20 mg/kg daily to 500 mg/kg daily;
  2,5-di-tert-butyl-4-[2'-thenoyl]phenol, dosage range from 3 mg/kg daily to 300 mg/kg daily;
  and antioxidant combinations such as that of ascorbic acid (dosage range from 1 mg daily to 60 mg daily), alpha-tocopherol (dosage range from 200 I. U. daily to 3,500 I. U. daily), beta-carotene (1 mg daily to 100 mg daily) and the antioxidant co-agent selenium (dosage range from 25 µg daily to 0.5 mg daily);

(f) immunosuppressive drugs such as
  cyclosporine (Sandimmune, Sandoz Pharmaceutical), dosage range from 1 mg/kg daily to 15 mg/kg daily;
  azathioprine (Imuran, Burroughs Wellcome), dosage range from 0.25 mg/kg daily to 5 mg/kg daily; and
  azathioprine/glucocorticoid combinations such as azathioprine in a dosage range from 0.25 mg/kg daily to 5 mg/kg daily in combination with intravenous, intramuscular, subcutaneous or oral methyl prednisolone, dosage range from 0.1 mg/kg daily (or alternate day) to 5 mg/kg daily (or alternate day);

(g) agents which decrease blood platelet aggregation such as
  acetylsalicylic acid (Ecotrin, SmithKline Beecham Consumer Brands), dosage range from 25 mg daily to 4 gm daily; and
  dipyridamole (Persantine, Boehringer Ingelheim), dosage range from 25 mg daily to 400 mg daily;

(h) agents which decrease blood viscosity such as
  pentoxifylline (Trental, Hoechst-Roussel), dosage range from 100 mg daily to 1.2 gm daily;

(t) mixed cow brain gangliosides (Cronassial, Fidia Pharmaceutical, marketed in several countries in Western Europe, South America and the Far East), intravenous, intramuscular or subcutaneous dosage in the range of 20 mg daily to 100 mg daily;

(j) analgesic agents for treatment of chronic pain such as acetaminophen (Extra Strength Tylenol, McNeil Consumer), dosage range from 300 mg daily to 4 gm daily;

(k) various agents for treatment of diabetes-related nephrotic syndrome such as
  furosemide (Lasix, Hoechst-Roussel), dosage range from 5 mg daily to 600 mg daily;
  metolazone (Mykrox, Fisions Pharmaceuticals), dosage range from 0.1 mg daily to 1 mg daily;
  lovastatin (Mevacor, Merck & Co.), dosage range from 2 mg daily to 80 mg daily;
  heparin sodium (Tubex, Wyeth-Ayerst), intravenous, intramuscular or subcutaneous dosage range from 1,000 USP units daily to 20,000 USP units daily;
  warfarin sodium (Coumadin, Du Pont Pharmaceutical), dosage range from 0.25 mg daily to 10 mg daily; and
  aminoguanidine (Alteon), intravenous, intramuscular, subcutaneous or oral dosage range from 5 mg/kg daily to 100 mg/kg daily; and
(l) aldose reductase inhibitors such as
  sorbinil (Pfizer), intravenous, intramuscular, subcutaneous or oral dosage range from 1 mg/kg daily to 25 mg/kg daily;
  (E)-3-carboxymethyl-5-[(2E)-methyl-3-phenylpropenylidene]rhodanine, intravenous, intramuscular, subcutaneous or oral dosage range from 1 mg/kg daily to 40 mg/kg daily;
  alrestatin, intravenous, intramuscular, subcutaneous or oral dosage range from 1 mg/kg daily to 100 mg/kg daily;
  statil, intravenous, intramuscular, subcutaneous or oral dosage range from 1 mg/kg daily to 25 mg/kg daily; and
  tolrestat (Ayerst-Wyeth Laboratories), intravenous, intramuscular, subcutaneous or oral dosage range from 1 mg/kg daily to 25 mg/kg daily.

EXAMPLE 4

Clinical treatment of symptomology related to aging may be improved by use of the invention originally disclosed in U.S. patent application Ser. No. 07/660,561, filed Feb. 21, 1991, now abandoned, in combination with known medicaments, including co-agent use of:

(a) monoamine oxidase B inhibitors such as
  selegiline (Eldepryl, Somerset), dosage range from 5 mg daily to 10 mg daily;
(b) acetylcholinesterase inhibitors such as
  physostigmine (Antilirium Injectable, Forest Pharmaceuticals), oral dosage range from 0.1 mg daily to 20 mg daily, or intravenous, intramuscular or subcutaneous dosage range from 5 µg daily to 3 mg daily, optionally with phosphatidylcholine co-agent, oral dosage range from zero to 15 gm daily;
  heptylphysostigmine, dosage range from 1 mg daily to 1 gram daily;
  tacrine (Cognexo Warner-Lambert), dosage range from 5 mg daily to 200 mg daily, optionally with phosphatidylcholine co-agent, dosage range from zero to 15 gm daily;
  (±)-9-amino-1,2,3,4-tetrahydroacridin-1-ol, dosage range from 2 mg daily to 200 mg daily;
  metrifonate, intramuscular, intravenous, subcutaneous or oral dosage range from 0.1 mg/kg daily to 125 mg/kg daily;
  velnacrine maleate (Mentane, Hoechst-Roussel), dosage range from 10 mg daily to 350 mg daily;
  methanesulfonyl fluoride, intravenous, intramuscular, subcutaneous or oral dosage range from 5 mg/kg daily to 350 mg/kg daily;
  phenylmethylsulfonyl fluoride, intravenous, subcutaneous, intramuscular or oral dosage range from 5 mg/kg daily to 60 mg/kg daily;
  huperzine A, intramuscular, intravenous, subcutaneous or oral dosage range from 10 µg/kg daily to 1 mg/kg daily;
  huperzine B, intramuscular, intravenous, subcutaneous or oral dosage range from 10 µg/kg daily to 1 mg/kg daily;
  edrophonium chloride (Hoffman LaRoche), intravenous, intramuscular, subcutaneous or oral dosage range from 2 mg daily to 400 mg daily;
  galanthamine, intravenous, intramuscular, subcutaneous or oral dosage range from 5 mg daily to 100 mg daily; and
  miotine, intravenous, intramuscular, subcutaneous or oral dosage range from 2 mg daily to 400 mg daily;
(c) angiotensin-converting enzyme inhibitors such as
  captopril (Capoten, Squibb), dosage range from 5 mg daily to 300 mg daily;
  captopril in combination with hydrochlorothiazide (Capozide, Squibb), dosage range from 5 mg captopril and 3 mg hydrochlorothiazide daily to 150 mg captopril and 50 mg hydrochlorothiazide daily;
  enalapril maleate (Vasotec, Merck & Co.), dosage range from 0.5 mg daily to 100 mg daily;
  enalaprilat, dosage range from 0.5 mg daily to 100 mg daily;
  enalapril maleate/hydrochlorothiazide combination (Vaseretic, Merck & Co.), dosage range from 2.5 mg enalapril maleate and 6.25 mg hydrochlorothiazide daily to 20 mg enalapril maleate and 50 mg hydrochlorothiazide daily;
  fosinopril (Monopril, Mead Johnson Pharmaceuticals), dosage range from 2 mg daily to 60 mg daily;
  lisinopril (Zestril, Stuart), dosage range from 1 mg daily to 40 mg daily;
  ramipril (Altace, Hoechst-Roussel), dosage range from 0.5 mg daily to 10 mg daily;
  epi-captopril, dosage range from 1 mg daily to 300 mg daily;
  alacepril, dosage range from 5 mg daily to 300 mg daily;
  quinapril, dosage range from 0.5 mg daily to 40 mg daily;
  perindopril, dosage range from 0.2 mg daily to 40 mg daily;
  delapril, dosage range from 4 mg daily to 1.5 grams daily;
  cilazapril, dosage range from 0.2 mg daily to 40 mg daily;
  pivalopril, dosage range from 2 mg daily to 250 mg daily;
  rentiapril, dosage range from 1 mg daily to 150 mg daily;
  zofenopril, dosage range from 1 mg daily to 150 mg daily; and
  zofenoprilat, dosage range from 1 mg daily to 150 mg daily;
(d) N-methyl-D-aspartate glutamate receptor antagonists administered orally, subcutaneously, intramuscularly or intravenously such as
  milacemide, dosage range from 50 mg daily to 2.5 grams daily;
  trihexyphenidyl (Artane, Lederle), dosage range from 0.1 mg daily to 20 mg daily;
  ethopropazine (Paridol), dosage range from 10 mg daily to 400 mg daily;

procyclidine (Kemadrin, Burroughs Wellcome), dosage range from 1 mg daily to 40 mg daily;

diphenhydramine (Benadryl, Parke-Davis), dosage range from 5 mg daily to 200 mg daily;

dizocilpine (Neurogard, Merck Sharp & Dohme), dosage range from 0.1 µg/kg daily to 10 mg/kg daily;

amantadine (Symmetrel, Du Pont Multi-Source Products), dosage range from 10 mg daily to 400 mg daily; and memantine, dosage range from 10 mg daily to 400 mg daily;

(e) antioxidant agents which may be used in combination such as ascorbic acid, dosage range from 1 mg daily to 60 mg daily;

alpha-tocopherol, dosage range from 200 I. U. daily to 3,500 I. U. daily;

beta-carotene, 1 mg daily to 100 mg daily; and selenium, dosage range from 25 µg daily to 0.5 mg daily;

(f) vasodilator and other nootropic direct brain metabolic enhancer drugs such as flunarizine, dosage range from 2 mg daily to 100 mg daily;

nimodipine (Nimotop, Miles Pharmaceutical), dosage range from 300 mg daily to 3.6 gm daily;

idebenone, dosage range from 5 mg/kg daily to 150 mg/kg daily;

ebiratide, subcutaneous dosage range from 3 µg/kg daily to 1 mg/kg daily;

vinpocetine (Cavinton, Chemical Works of Gedeon Richter, Ltd.), intravenous or oral dosage range from 5 mg/kg daily to 300 mg/kg daily;

pentoxifylline, dosage range from 50 mg daily to 3 grams daily;

citicoline, dosage range from 50 mg daily to 5 grams daily;

bromvincamine, dosage range from 25 mg daily to 3 grams daily;

cyclandelate, dosage range from 25 mg daily to 3 grams daily;

isoxsuprene, dosage range from 25 mg daily to 3 grams daily;

nafronyl, dosage range from 25 mg daily to 3 grams daily;

papaverine, dosage range from 25 mg daily to 3 grams daily;

suloctidil, dosage range from 25 mg daily to 3 grams daily;

vinburnine, dosage range from 25 mg daily to 3 grams daily;

vincamine, dosage range from 25 mg daily to 3 grams daily;

vindeburnol, dosage range from 25 mg daily to 3 grams daily;

nicergoline (Sermion), intravenous, intramuscular, subcutaneous or oral dosage range from 6 mg daily to 10 grams;

razobazam, intravenous, intramuscular, subcutaneous or oral dosage range from 0.1 mg/kg daily to 25 mg/kg daily;

exifone, intravenous, intramuscular, subcutaneous or oral dosage range from 1 mg daily to 1 gram daily;

rolipram, intravenous, intramuscular, subcutaneous or oral dosage range from 1 mg daily to 1 gram daily;

naloxone, intravenous, intramuscular, subcutaneous or oral dosage range from 5 mg daily to 200 mg daily;

ethyl 5-isopropyloxy-4-methyl-beta-carboline-3-carboxylate, intravenous, intramuscular, subcutaneous or oral dosage range from 2 mg/kg daily to 100 mg/kg daily;

N'-methyl-beta-carboline-3-carboxamide, intravenous, intramuscular, subcutaneous or oral dosage range from 2 mg/kg daily to 100 mg/kg daily;

methyl 6,7-dimethoxy-4-ethyl-beta-carboline-3-carboxylate, intravenous, intramuscular, subcutaneous or oral dosage range from 0.1 mg/kg daily to 10 mg/kg daily;

ethyl 5-methoxy-4-ethyl-beta-carboline-3-carboxylate, intravenous, intramuscular, subcutaneous or oral dosage range from 1 mg/kg daily to 30 mg/kg daily;

sabeluzole, dosage range from 2 mg daily to 40 mg daily;

phosphatidylserine, intravenous, intramuscular, subcutaneous or oral dosage range from 1 mg/kg daily to 250 mg/kg daily;

piracetam, dosage range from 50 mg/kg daily to 8 grams/kg daily;

aniracetam, dosage range from 50 mg/kg daily to 1 gram/kg daily;

pyroglutamic acid, intravenous, intramuscular, subcutaneous or oral dosage range from 100 mg/kg daily to 5 grams/kg daily;

tenilsetam, dosage range from 10 mg daily (or alternate day) to 1 gram daily (or alternate day), or from 25 mg once a week to 1 gram once a week;

pramiracetam, dosage range from 50 mg/kg daily to 8 grams/kg daily;

oxiracetam, dosage range from 200 mg daily to 2 grams daily;

rolziracetam, intravenous, intramuscular, subcutaneous or oral dosage range from 1 mg daily to 1 gram daily;

etiracetam, dosage range from 50 mg/kg daily to 8 grams/kg daily;

propentophylline, intravenous, intramuscular, subcutaneous or oral dosage range from 50 mg daily to 3 grams daily;

dupracetam, intravenous, intramuscular, subcutaneous or oral dosage range from 1 mg daily to 1 gram daily; and ergoloid mesylates (Hydergine, Sandoz Pharmaceuticals), dosage range from 0.5 mg daily to 40 mg daily;

(g) postsynaptic receptor agonists such as arecoline, subcutaneous or oral dosage range from 2 mg daily to 25 mg daily;

oxotremorine, intravenous, intramuscular, subcutaneous or oral dosage range from 1 µg/kg daily to 0.2 mg/kg daily; and bethanechol (Urecholine, Merck & Co.), dosage range from 5 mg daily to 200 mg daily;

levacecarnine (acetyl-L-carnitine or Alcar, Sigma-Tau), dosage range from 500 mg daily to 5 grams daily; and ethyl nipecotate, intravenous, intramuscular, subcutaneous or oral dosage range from 2 mg daily to 250 mg daily;

(h) biogenic amines and co-agents related thereto such as clonidine (Catapres, Boehringer Ingelheim), dosage range from 20 µg daily to 2.4 mg daily;

guanfacine (Tenex, Robins), dosage range from 0.25 mg daily to 3 mg daily;

alaproclate, dosage range from 0.25 mg daily to 3 mg daily;

fipexide, dosage range from 0.25 mg daily to 3 mg daily;

zimeldine, dosage range from 0.25 mg daily to 3 mg daily; and citalopram, dosage range from 0.25 mg daily to 3 mg daily;

(i) anfacine, intravenous, intramuscular, subcutaneous or oral dosage range from 1 mg/kg daily to 350 mg/kg daily;

(j) agents which may enhance acetylcholine synthesis, storage or release such as phosphatidylcholine, dosage range from 1 gm daily to 15 gm daily;

4-aminopyridine, intravenous, intramuscular, subcutaneous or oral dosage range from 0.25 mg/kg daily to 10 mg/kg daily;

3,4-diaminopyridine, intravenous, intramuscular, subcutaneous or oral dosage range from 50 µg daily to 100 mg daily;

choline chloride, dosage range from 500 mg daily to 30 grams daily;

choline bitartrate, dosage range from 500 mg daily to 30 grams daily;

bifemelane, dosage range from 1 mg/kg daily to 1.2 grams/kg daily;

vesamicol, dosage range from 50 µg/kg daily to 500 mg/kg daily;

secoverine, dosage range from 50 µg/kg daily to 500 mg/kg daily;

tetraphenylurea, dosage range from 50 µg/kg daily to 500 mg/kg daily; and nicotinamide, dosage range from 1 mg/kg daily to 500 mg/kg daily;

(k) prostaglandin $B_1$ oligomers (also known as polymeric 15-keto prostaglandin B or $PGB_x$), intravenous, intramuscular, subcutaneous or oral dosage range from 5 mg/kg daily to 400 mg/kg daily;

(l) acetylhomocysteine thiolactone, intravenous, intramuscular, subcutaneous or oral dosage range from 0.5 mg/kg daily to 25 mg/kg daily;

(m) ganglioside $GM_1$, intravenous, intramuscular or subcutaneous dosage range from 20 mg daily to 200 mg daily;

(n) sulbutiamine, dosage range from 1 mg/kg daily to 350 mg/kg daily; and (o) serotonergic receptor antagonists such as ketanserin (Ketan, Janssen Pharmaceutica), intravenous, intramuscular, subcutaneous or oral dosage range from 0.1 mg/kg daily to 20 mg/kg daily; and mianserin (Mian, Organon International), intravenous, intramuscular, subcutaneous or oral dosage range from 0.1 mg/kg daily to 20 mg/kg daily.

EXAMPLE 5

Clinical treatment of tinnitus (nerve deafness) may be improved by use of the invention originally disclosed in U.S. patent application Ser. No. 07/660,561, filed Feb. 21, 1991, now abandoned, in combination with known medicaments, including co-agent use of:

(a) antidepressants or antianxiety medications such as
amitriptyline (Elavil, Stuart), dosage range from 50 mg daily to 300 mg daily;
amitriptyline/perphenazine combinations (Etrafon, Schering), dosage range from 4 mg perphenazine and 50 mg amitriptyline daily to 16 mg perphenazine and 100 mg amitriptyline daily;
alprazolam (Xanax, Upjohn), dosage range from 125 µg daily to 4 mg daily; and
triptolene, dosage range from 0.1 mg daily to 20 mg daily;

(b) anticonvulsants such as
primidone (Mysoline, Wyeth-Ayerst), dosage range from 10 mg daily to 2 gm daily;
phenytoin (Dilantin, Parke-Davis), dosage range from 10 mg daily to 600 mg daily; and
carbamazepine (Tegretol, Basel), dosage range from 40 mg daily to 1.6 gm daily;

(c) lidocaine (Xylocaine, Astra), intravenous, intramuscular or subcutaneous dosage range from 1 mg daily to 300 mg daily, or oral forms of lidocaine in a dosage range of 1 mg daily to 300 mg daily;

(d) tocainide, dosage range from 10 mg daily to 400 mg daily;

(e) flecinide, dosage range from 10 mg daily to 400 mg daily;

(f) nicotinamide, dosage range from 1 mg/kg daily to 500 mg/kg daily;

(g) aminooxyacetic acid, dosage range from 10 mg daily to 500 mg daily;

(h) praxilene, dosage range from 5 mg/kg daily to 100 mg/kg daily;

(i) aniracetam, dosage range from 50 mg/kg daily to 1 gram/kg daily;

(j) piracetam, dosage range from 1 mg daily to 100 mg daily;

(k) 13-cis-retinoic acid, dermal, subcutaneous, intravenous, intramuscular or oral dosage range from 50 µg/kg daily to 25 mg/kg daily; and (l) 13-trans-retinoic acid, dermal, subcutaneous, intravenous, intramuscular or oral dosage range from 50 µg/kg daily to 25 mg/kg daily.

EXAMPLE 6

Clinical treatment of multiple sclerosis may be improved by use of the invention originally disclosed in U.S. patent application Ser. No. 07/660,561 in combination with known medicaments, including co-agent use of:

(a) azathioprine (Imuran, Burroughs Wellcome), dosage range from 5 mg daily to 300 mg daily;

(b) copolymer-1 (random polymer of L-alanine, L-glutamic acid, L-lysine and L-tyrosine, ratio of 6.0:1.9:4.7:1.0, of molecular weight between 14,000 and 23,000 Daltons), intravenous, subcutaneous or intramuscular dosage range 2 mg daily to 40 mg daily;

(c) cyclosporine (Sandimmune, Sandoz Pharmaceutical), dosage range from 1 mg/kg daily to 15 mg/kg daily;

(d) interferons such as
alfa-2a interferon (Roferon-A, Roche Laboratories), intravenous, intramuscular or subcutaneous dosage range from 300,000 IU daily to 36,000,000 IU daily;
alfa-2b interferon (Intron-A, Schering), intravenous, intramuscular or subcutaneous dosage range from 300,000 IU daily to 5,000,000 IU daily; alfa-N3 interferon (Alferon N Injection, Purdue Frederick), intravenous, intramuscular or subcutaneous dosage range from 250,000 IU daily to 2,500,000 IU daily;
beta interferon (Betaseron, Berlex), intravenous, intramuscular or subcutaneous dosage range from 5,000 U/kg daily to 50,000 U/kg daily; and gamma-1b interferon (Actimmune, Genentech), intramuscular or subcutaneous dosage range from 5,000 U/kg daily to 50,000 U/kg daily;

(e) corticosteroids such as
prednisone (Deltasone, Upjohn), dosage range from 0.5 mg daily or every other day to 200 mg daily or every other day; and
dexamethasone (Decadron, Merck & Co.), dosage range from 0.1 mg daily or every other day to 10 mg daily or every other day;

(f) cyclophosphamide (Cytoxan, Bristol-Myers Oncology), intravenous, intramuscular, subcutaneous or oral dosage range from 0.1 mg/kg daily to 10 mg/kg daily;

(g) 4-aminopyridine, intravenous, intramuscular, subcutaneous or oral dosage range from 0.25 mg/kg daily to 10 mg/kg daily;

(h) baclofen (Atrofen, Athena Neurosciences), dosage range from 1 mg daily to 80 mg daily; and (i) 3,4-diaminopyridine, dosage range from 50 µg daily to 100 mg daily.

EXAMPLE 7

Clinical treatment of amyotrophic lateral sclerosis may be improved by use of the invention originally disclosed in U.S. patent application Ser. No. 07/660,561, filed Feb. 21, 1991, now abandoned, in combination with known medicaments, including co-agent use of:

(a) mixed cow brain gangliosides (Cronassial, Fidia Pharmaceutical, marketed in several countries in Western Europe, South America and the Far East), intramuscular, intravenous or subcutaneous dosage range from 20 mg daily to 100 mg daily;

(b) thyrotropin releasing factor (Relefact TRH, Ferring); intravenous, subcutaneous or intramuscular dosage range from 0.5 mg daily to 500 mg daily;

(c) serine, dosage range from 500 mg daily to 15 gm daily;

(d) L-threonine, dosage range from 500 mg daily to 15 gm daily;

(e) glycine, dosage range from 500 mg daily to 15 gm daily;

(f) N-methyl-D-aspartate glutamate receptor antagonists administered orally, intramuscularly, subcutaneously or intravenously such as
milacemide, dosage range from 50 mg daily to 2.5 grams daily;
trihexyphenidyl (Artane, Lederle), dosage range from 0.1 mg daily to 20 mg daily;
ethopropazine (Paridol), dosage range from 10 mg daily to 400 mg daily;
procyclidine (Kemadrin, Burroughs Wellcome), dosage range from 1 mg daily to 40 mg daily;
diphenhydramine (Benadryl, Parke-Davis), dosage range from 5 mg daily to 200 mg daily;
dizocilpine (Neurogard, Merck Sharp & Dohme), dosage range from 0.1 µg/kg daily to 10 mg/kg daily;
amantadine (Symmetrel, Du Pont Multi-Source Products), dosage range from 10 mg daily to 400 mg daily; and
memantine, dosage range from 10 mg daily to 400 mg daily.

EXAMPLE 8

Clinical treatment of Huntington's disease may be improved by use of the invention originally disclosed in U.S. patent application Ser. No. 07/660,561, filed Feb. 21, 1991, now abandoned, in combination with known medicaments including (a) N-methyl-D-aspartate glutamate receptor antagonists administered orally, intramuscularly, subcutaneously or intravenously such as
milacemide, dosage range from 50 mg daily to 2.5 grams daily;
trihexyphenidyl (Artane, Lederle), dosage range from 0.1 mg daily to 20 mg daily;
ethopropazine (Paridol), dosage range from 10 mg daily to 400 mg daily;
procyclidine (Kemadrin, Burroughs Wellcome), dosage range from 1 mg daily to 40 mg daily;
diphenhydramine (Benadryl, Parke-Davis), dosage range from 5 mg daily to 200 mg daily;
dizocilpine (Neurogard, Merck Sharp & Dohme), dosage range from 0.1 µg/kg daily to 10 mg/kg daily;
amantadine (Symmetrel, Du Pont Multi-Source Products), dosage range from 10 mg daily to 400 mg daily; and
memantine, dosage range from 10 mg daily to 400 mg daily;

(b) agents which may enhance acetylcholine synthesis, storage or release such as
phosphatidylcholine, dosage range from 1 gm daily to 15 gm daily;
3,4-diaminopyridine, dosage range from 50 µg daily to 100 mg daily;
choline chloride, dosage range from 500 mg daily to 20 grams daily;
and choline bitartrate, dosage range from 500 mg daily to 20 grams daily; and (c) postsynaptic receptor agonists such as
arecoline, intravenous, intramuscular, subcutaneous or oral dosage range from 2 mg daily to 25 mg daily.

EXAMPLE 9

Clinical treatment of olivopontocerebellar atrophy may be improved by use of the invention originally disclosed in U.S. patent application Ser. No. 07/660,561, filed Feb. 21, 1991, now abandoned, in combination with known medicaments including N-methyl-D-aspartate glutamate receptor antagonists administered orally, subcutaneously, intramusculary or intravenously such as
milacemide, dosage range from 50 mg daily to 2.5 grams daily;
trihexyphenidyl (Artane, Lederle), dosage range from 0.1 mg daily to 20 mg daily;
ethopropazine (Paridol), dosage range from 10 mg daily to 400 mg daily;
procyclidine (Kemadrin, Burroughs Wellcome), dosage range from 1 mg daily to 40 mg daily;
diphenhydramine (Benadryl, Parke-Davis), dosage range from 5 mg daily to 200 mg daily;
dizocilpine (Neurogard, Merck Sharp & Dohme), dosage range from 0.1 µg/kg daily to 10 mg/kg daily;
amantadine (Symmetrel, Du Pont Multi-Source Products), dosage range from 10 mg daily to 400 mg daily; and
memantine, dosage range from 10 mg daily to 400 mg daily.

EXAMPLE 10

Clinical treatment of alcoholic polyneuropathy may be improved by use of the invention originally disclosed in U.S.

patent application Ser. No. 07/660,561, filed Feb. 21, 1991, now abandoned, in combination with known medicaments, including (a) mixed cow brain gangliosides (Cronassial, Fidia Pharmaceutical, marketed in several countries in Western Europe, South America ana the Far East, intravenous, intramuscular or subcutaneous dosage in the range from 20 mg daily to 100 mg daily;

(b) tiapride, dosage range from 1 mg daily to 400 mg daily;

(c) physostigmine (Antilirium Injectable, Forest Pharmaceuticals), oral dosage range from 0.1 mg daily to 20 mg daily, or intravenous, intramuscular or subcutaneous dosage range from 5 µg daily to 3 mg daily, optionally with phosphatidylcholine co-agent, oral dosage range from zero to 15 gm daily;

(d) piracetam, dosage range from 1 mg daily to 100 mg daily; and (e) cyclandelate, dosage range from 25 mg daily to 3 grams daily.

EXAMPLE 11

Clinical treatment of hereditary motor and sensory neuropathies may be improved by use of the invention originally disclosed in U.S. patent application Ser. No. 07/660,561, filed Feb. 21, 1991, now abandoned, in combination with known medicaments, including (a) mixed cow brain gangliosides (Cronassial, Fidia Pharmaceutical, marketed in several countries in Western Europe, South America and the Far East, intravenous, intramuscular or subcutaneous dosage in the range from 20 mg daily to 100 mg daily; and (b) 3,4-diaminopyridine, intravenous, intramuscular or subcutaneous dosage range from 50 µg daily to 100 mg daily.

EXAMPLE 12

Clinical treatment of urinary incontinence resulting from Alzheimer's senile dementia, demyelinating diseases such as multiple sclerosis, peripheral nerve lesions, diabetes mellitus and alcoholic polyneuropathy may be improved by use of the invention originally disclosed in U.S. patent application Ser. No. 07/660,561, filed Feb. 21, 1991, now abandoned, in combination with known medicaments, including co-agent use of:

(a) cholinergics such as
bethanechol (Urecholine, Merck & Co.), dosage range from 5 mg daily to 200 mg daily alone, or in combination with prazosin, dosage range from 0.5 mg daily to 4 mg daily;

(b) anti-cholinergics such as
hyoscyamine sulfate, dosage range from 0.1 mg daily to 1 mg daily;
atropine sulfate, dosage range from 25 µg daily to 0.2 mg daily; propantheline (Pro-Banthine, Schiapparelli Searle), dosage range from 2.5 mg daily to 75 mg daily;
oxybutynin (Ditropan, Marion Merrell Dow), dosage range from 2.5 mg daily to 20 mg daily; and
dicyclomine (Bentyl, Marion Merrell Dow), dosage range from 10 mg daily to 160 mg daily;

(c) alpha-adrenergics such as
ephedrine, dosage range from 10 mg daily to 150 mg daily; and phenylpropanolamine, dosage range from 10 mg daily to 150 mg daily;

(d) tricyclic agents such as
imipramine (Tofranil, Geigy), dosage range from 10 mg daily to 200 mg daily; and
doxepin (Adapin, Lotus Biochemical), dosage range from 10 mg daily to 300 mg daily;

(e) flavoxate (Uripas, SmithKline Beecham Pharmaceuticals), dosage range from 30 mg daily to 800 mg daily;

(f) beta-adrenergic blockers such as propranolol (Inderal, Wyeth-Ayerst Laboratories), dosage range from 30 mg daily to 640 mg daily;
pindolol (Visken, Sandoz Pharmaceuticals), dosage range from 10 mg daily to 60 mg daily;
metoprolol tartrate (Lopressor, Geigy), dosage range from 100 mg daily to 450 mg daily;
metoprolol succinate (Toprol XL, Astra), dosage range from 50 mg daily to 400 mg daily; and
atenolol (Tenormin, ICI Pharma), dosage range from 50 mg daily to 200 mg daily; and (g) vasopressin analogues such as
desmopressin (DDAVP Nasal Spray, Rhone-Poulenc Rorer Pharmaceuticals), dosage range from 10 µg daily to 40 µg daily.

EXAMPLE 13

Clinical treatment of gastroesophageal reflux disease, hypoperistalsis and/or delayed gastric emptying may be improved by use of the invention originally disclosed in U.S. patent application Ser. No. 07/660,561 in combination with known medicaments, including co-agent use of:

(a) metoclopramide (Reglan, A. H. Robins), intravenous, intramuscular, subcutaneous or oral dosage range from 2 mg daily to 60 mg daily;

(b) cisapride (Prepulsid, Janssen Pharmaceutica), intravenous, intramuscular, subcutaneous or oral dosage range from 1 mg daily to 100 mg daily;

(c) famotidine (Pepcid, Merck & Co.), dosage range from 2 mg daily to 80 mg daily;

(d) cimetidine (Tagamet, SmithKline Beecham), dosage range from 40 mg daily to 1.6 gm daily;

(e) ranitidine (Zantac, Glaxo Pharmaceuticals), dosage range from 30 mg daily to 6 gm daily;

(f) omeprazole (Prilosec, Merck & Co.), dosage range from 5 mg daily to 400 mg daily; and (g) galanthamine, intravenous, intramuscular, subcutaneous or oral dosage range from 5 mg daily to 100 mg daily.

EXAMPLE 14

Clinical treatment of symptomology related to onset and development of atherosclerosis may be improved by use of the invention originally disclosed in U.S. patent application Ser. No. 07/660,561, filed Feb. 21, 1991, now abandoned, in combination with known medicaments, including co-agent use of:

(a) angiotensin-converting enzyme inhibitor free radical scavenging agents possessing sulfhydryl groups such as
captopril (Capoten, Squibb), dosage range from 5 mg daily to 300 mg daily;
captopril in combination with hydrochlorothiazide (Capozide, Squibb), dosage range from 5 mg captopril and 3 mg hydrochlorothiazide daily to 150 mg captopril and 50 mg hydrochlorothiazide daily;

epi-captopril, dosage range from 1 mg daily to 300 mg daily;

alacepril, dosage range from 5 mg daily to 300 mg daily;

pivalopril, dosage range from 2 mg daily to 250 mg daily; and rentiapril, dosage range from 1 mg daily to 150 mg daily;

(b) fibric acid derivative anti-hyperlipidemia agents such as gemfibrozil (Lopid, Parke-Davis), dosage range from 100 mg daily to 1.2 gm daily;

clofibrate (Atromid-S, Wyeth-Ayerst Laboratories), dosage range from 20 mg daily to 2 gm daily;

bezafibrate, dosage range from 100 mg daily to 1.3 grams daily; and fenofibrate, dosage range from 40 mg daily to 500 mg daily;

(c) metformin, dosage range from 100 mg daily to 4 grams daily;

(d) nicotinic acid (Nicolar, Rhone-Poulenc Rorer), dosage range from 500 mg daily to 6 gm daily;

(e) natural hydroscopic non-digestible edible plant carbohydrate polymers such as guar gum, dosage range from 2 grams daily to 20 grams daily;

(f) 3-hydroxy-3-methylglutaryl-CoA reductase inhibitors such as lovastatin (Mevacor, Merck & Co.), dosage range from 2 mg daily to 80 mg daily;

pravastatin (Pravachol, Squibb), dosage range from 1 mg daily to 40 mg daily; and simvastatin (Zocor, Merck & Co.), dosage range from 1 mg daily to 40 mg daily;

(g) acipimox, dosage range from 1 mg/kg daily to 500 mg/kg daily;

(h) bile acid sequestrants such as cholestyramine resin (Questran Light, Bristol Laboratories), dosage range from 400 mg anhydrous cholestyramine resin daily to 16 gm anhydrous cholestyramine resin daily; and colestipol (Colestid, Upjohn), dosage range from 500 mg daily to 30 gm daily;

(t) antioxidants such as probucol (Lorelco, Marion Merrell Dow), dosage range from 100 mg daily to 1 gm daily; and prostaglandin $B_1$ oligomers (also known as polymeric 15-keto prostaglandin B or $PGB_x$), intravenous, intramuscular or subcutaneous dosage range from 5 mg/kg daily to 40 mg/kg daily;

(j) anti-hypertensive agents including oral diuretics such as bendroflumethiazide (Naturetin), dosage range from 0.5 mg daily to 5 mg daily;

benzthiazide (Exna), dosage range from 1 mg daily to 50 mg daily;

chlorothiazide (Diuril), dosage range from 10 mg daily to 500 mg daily;

chlorthalidone (Hygroton), dosage range from 1 mg daily to 50 mg daily;

cyclothiazide (Anhydron), dosage range from 0.1 mg daily to 2 mg daily;

hydrochlorothiazide (Hydro-Diuril), dosage range from 1 mg daily to 50 mg daily;

hydroflumethiazide (Saluron), dosage range from 1 mg daily to 50 mg daily;

indapamide (Lozol), dosage range from 0.25 mg daily to 5 mg daily;

methylclothiazide (Enduron), dosage range from 0.25 mg daily to 5 mg daily;

metolazone (Zaroxolyn), dosage range from 0.1 mg daily to 10 mg daily;

polythiazide (Renese), dosage range from 0.2 mg daily to 4 mg daily;

quinethazone (Hydromox), dosage range from 2.5 mg daily to 100 mg daily;

trichlormethiazide (Naqua), dosage range from 0.1 mg daily to 4 mg daily; and idebenone, dosage range from 5 mg/kg daily to 150 mg/kg daily;

loop diuretics such as bumetanide (Bumex), 50 µg daily to 10 mg daily;

ethacrynic acid (Edecrin), dosage range from 2.5 mg daily to 100 mg daily;

furosemide (Lasix), dosage range from 2 mg daily to 600 mg daily; and torsemide (Presaril, Boehringer-Manheim), dosage range of 0.5 mg daily to 20 mg daily;

and potassium-sparing diuretics such as amiloride (Midamor), dosage range from 0.5 mg daily to 10 mg daily;

spironolactone (Aldactone), dosage range from 2.5 mg daily to 400 mg daily; and triamterene (Dyrenium), dosage range from 5 mg daily to 150 mg daily;

beta-adrenergic antagonists such as acebutolol (Sectral), dosage range from 20 mg daily to 1.2 gm daily;

atenolol (Tenormin), dosage range from 2.5 mg daily to 200 mg daily;

betaxolol (Kerlone), dosage range from 1 mg daily to 20 mg daily;

carteolol (Cartrol), dosage range from 0.25 mg daily to 10 mg daily;

labetalol (Normodyne), dosage range from 20 mg daily to 1.8 gm daily;

metoprolol (Lopressor), 5 mg daily to 200 mg daily;

nadolol (Corgard), dosage range from 4 mg daily to 240 mg daily;

penbutolol (Levatol), dosage range from 2 mg daily to 80 mg daily;

pindolol (Visken), dosage range from 0.5 mg daily to 60 mg daily;

propranolol (Inderal or Inderal LA), dosage range from 4 mg daily to 320 mg daily;

timolol (Blocadren), dosage range from 1 mg daily to 60 mg daily;

and bisoprolol (Zebeta, Lederle), dosage range from 0.5 mg daily to 10 mg daily;

calcium antagonists such as diltiazem (Cardizem or Cardizem SR), dosage range from 10 mg daily to 360 mg daily;

verapamil (Calan or Calan SR), dosage range from 10 mg daily to 480 mg daily;

nifedipine (Procardia), dosage range from 3 mg daily to 180 mg daily;

nifedipine (Procardia XL), dosage range from 3 mg daily to 90 mg daily;

nicardipine (Cardene), dosage range from 6 mg daily to 120 mg daily;

isradipine (DynaCirc), dosage range from 0.5 mg daily to 20 mg daily;

amlodipine (Norvasc, Pfizer Labs Division), dosage range from 0.5 mg daily to 10 mg daily;

felodipine (Plendil, Merck & Co.), dosage range from 0.5 mg daily to 20 mg daily;

nimodipine (Nimotop, Miles Pharmaceutical), dosage range from 300 mg daily to 3.6 gm daily;

flunarizine, dosage range from 2 mg daily to 100 mg daily;

angiotensin-converting enzyme inhibitors such as captopril (Capoten), dosage range from 2.5 mg daily to 300 mg daily;

enalapril (Vasotec), dosage range from 0.25 mg daily to 40 mg daily;

fosinopril (Monopril), dosage range from 1 mg daily to 60 mg daily;

lisinopril (Zestril), dosage range from 0.5 mg daily to 40 mg daily;

ramipril (Altace), dosage range from 0.25 mg daily to 10 mg daily;

quinapril (Accupril, Parke-Davis), dosage range from 1 mg daily to 80 mg daily;

quinapril/hydrochlorothiazide combinations (Accuretic, Parke-Davis), dosage range from 2 mg quinapril and 1.25 mg hydrochlorothiazide daily to 80 mg quinapril and 125 mg hydrochlorothiazide daily; and benazepril (Loretsin, CIBA Pharmaceutical), dosage range from 0.1 mg daily to 80 mg daily;

peptide-based renin inhibitors such as [(2S)-3-(4-methylpiperazin-1-yl)sulfonyl-2-(phenylmethyl)-propionyl]-N-[(1S,2R,3S)-1-(cyclohexylmethyl)-2,3-dihydroxy-5-methylhexyl]-L-[3-(thiazol-4-yl)alaninamide] (A-72517, Abbott Laboratories), oral, intravenous, intramuscular or subcutaneous dosage range from 0.1 mg/kg daily to 120 mg/kg daily;

centrally acting alpha-adrenergic agonists such as clonidine (Catapres), dosage range from 10 µg daily to 1.2 mg daily;

clonidine TTS (Catapres TTS transdermal skin patch), dosage range from 0.1 mg daily to 0.3 mg daily;

guanabenz (Wytensin), dosage range from 0.4 mg daily to 64 mg daily;

guanfacine (Tenex), 0.1 mg daily to 3 mg daily; and methyldopa (Aldomet), dosage range from 25 mg daily to 2 gm daily;

peripherally acting adrenergic antagonists such as guanadrel (Hylorel), dosage range from 1 mg daily to 100 mg daily;

guanethidine (Ismelin), dosage range from 1 mg daily to 150 mg daily;

whole root Rauwolfia alkaloids (Raudixin), dosage range from 5 mg daily to 100 mg daily; and reserpine (Serpasil), dosage range from 10 µg daily to 0.25 mg daily;

alpha-adrenergic antagonists such as prazosin (Minipress, Pfizer Labs Division), dosage range from 0.1 mg daily to 20 mg daily;

prazosin/polythiazide combination (Minizide, Pfizer Labs Division), dosage range from 0.1 mg prazosin and 50 ug polythiazide daily to 20 mg prazosin and 2 mg polythlazide daily;

terazosin (Hytrin), dosage range from 0.1 mg daily to 20 mg daily; and doxazosin (Cardura), dosage range from 0.1 mg daily to 16 mg daily;

direct-acting vasodilators such as hydralazine (Apresoline), dosage range from 3 mg daily to 300 mg daily; and minoxidil (Loniten), 0.25 mg daily to 100 mg daily; and (k) drugs for use in treatment of ischemic heart disease including nitrates such as oral isosorbide dinitrate, dosage range from 2 mg daily to 240 mg daily; and sustained-release trinitroglycerin, dosage range from 1 mg daily to 540 mg daily;

beta-adrenergic antagonists such as acebutolol (Sectral), dosage range from 20 mg daily to 1.2 gm daily;

atenolol (Tenormin), dosage range from 2.5 mg daily to 200 mg daily;

betaxolol (Kerlone), dosage range from 1 mg daily to 20 mg daily;

carteolol (Cartrol), dosage range from 0.25 mg daily to 10 mg daily;

labetalol (Normodyne), dosage range from 20 mg daily to 1.8 gm daily;

metoprolol (Lopressor), dosage range from 5 mg daily to 200 mg daily;

nadolol (Corgard), dosage range from 4 mg daily to 240 mg daily;

penbutolol (Levatol), dosage range from 2 mg daily to 80 mg daily;

pindolol (Visken), dosage range from 0.5 mg daily to 60 mg daily;

propranolol (Inderal or Inderal LA), dosage range from 4 mg daily to 320 mg daily;

timolol (Blocadren), dosage range from 1 mg daily to 60 mg daily;

and bisoprolol (Zebeta, Lederle), dosage range from 0.5 mg daily to 10 mg daily;

and calcium channel antagonists such as dilitiazem (Cardizem or Cardizem SR), dosage range from 10 mg daily to 360 mg daily;

verapamil (Calan or Calan SR), dosage range from 10 mg to 480 mg;

nifedipine (Procardia), dosage range from 3 mg daily to 180 mg daily;

nifedipine (Procardia XL), dosage range from 3 mg daily to 90 mg daily;

nicardipine (Cardene), dosage range from 6 mg daily to 120 mg daily;

isradipine (DynaCirc), dosage range from 0.5 mg daily to 20 mg daily;

amlodipine (Norvasc, Pfizer Labs Division), dosage range from 0.5 mg daily to 10 mg daily; and felodipine (Plendil, Merck & Co.), dosage range from 0.5 mg daily to 20 mg daily; and (l) ventricular antiarrhythmic drugs such as sotalol (Betapace, Berlex), dosage range from 30 mg daily to 320 mg daily;

mexilitene (Mexitil, Boehringer Ingelheim), dosage range from 60 mg daily to 1.2 gm daily;

propafenone (Rythmol, Knoll), dosage range from 45 mg daily to 900 mg daily;

quinidine (Quinaglute Dura-Tabs, Berlex), dosage range from 20 mg daily to 1.2 gm daily;

procainamide (Procan SR, Parke-Davis), dosage range from 200 mg daily to 5 gm daily;

pirmenol (Pimavar, Warner-Lambert), intravenous or oral dosage range from 25 mg daily to 500 mg daily.

6. Clinical Diagnosis of Chromosome 17 Hereditary Motor and Sensory Neuropathy by Electrophoretic Analysis of Cultured Fibroblast Proteins The results of a study conducted by this inventor and disclosed in U.S. patent application Ser. No. 08/026,617, filed Feb. 23, 1993, now abandoned, provide additional evidence that chemical crosslinking of neurofilaments may underlie at least part of the etiology of the chromosome 17 HMSN disorder. Cultured skin fibroblasts from three chromosome 17 HMSN donors and three control donors matched for age and sex were analyzed by two dimensional gel electrophoresis and subsequent computer image analysis. The HMSN patient skin biopsies came from donors who had previously participated in the organic acid metabolic profiling study noted above. Protein analysis by gel electrophoresis and subsequent computer image analysis were carried out at Protein Databases, Inc. (Huntington Station, N.Y.), with financial support provided by the National Foundation for Jewish Genetic Diseases (New York).

Cultured human fibroblast strains used in this study were obtained from the collection established by this inventor in the Microbiology Department of the University of Pennsylvania School of Medicine. For each of the six skin biopsy fibroblast strains examined cells were grown in vitro in pH 7.4 RPMI 1640 media supplemented with 10% fetal calf serum, L-glutamine, and penicillin-streptomycin antibiotics. Fibroblasts were grown to confluency and then divided 1:3 for each sub-culture. Sixth sub-culture fibroblasts were used for protein analysis by gel electrophoresis.

At Protein Databases, Inc. the protein contents of these six cultured fibroblast strains were subjected to two dimensional gel electrophoresis according to the procedure of Garrels (1979). Cultured fibroblast proteins were extracted into a sample buffer containing 0.3% sodium dodecyl sulfate, 5.0% 2-mercaptoethanol and Tris buffer, pH 8.0. For each sample, 30 µg protein was applied to a 2.7% acrylamide gel containing 2.0% ampholytes (pH range 5–7). After isoelectric focusing electrophoresis, the proteins of each sample were resolved in the second dimension according to molecular weight on a 12.5% acrylamide gel.

Cell proteins were not labeled with one or more radioactive amino acid. Instead, protein gel spots were visualized by use of silver staining according to the methods of Merril and coworkers (1979, 1981) and Morrissey (1981). Identification of individual protein spots on each gel was accomplished by electronic image processing followed by use of the PDQUEST™ computer analysis system (Protein Databases, Inc.).

In this study 145 protein spots were always seen in each of the three normal fibroblast strains, and 126 corresponding protein spots were always seen in each of the HMSN strains. However, each of the HMSN samples also showed 25 additional protein spots which were never seen in any of the control samples. There were no examples of a protein always seen in each of the control samples but never seen in any of the HMSN samples. The distribution of molecular weights of the additional HMSN-specific protein spots did not correspond to the molecular weight distribution of control protein spots. Rather, it was comparatively shifted up scale. Of the protein spots always seen in control samples, the largest had a molecular weight of 118,000. Of the 25 HMSN-specific protein spots, nine had molecular weights in the range of 130,000 to 192,000. The available information on these HMSN-specific proteins may be summarized as follows.

| designated protein number | apparent molecular weight | apparent isoelectric point (pI) |
|---|---|---|
| 1 | 89,300 | 4.53 |
| 2 | 33,100 | 4.95 |

-continued

| designated protein number | apparent molecular weight | apparent isoelectric point (pI) |
|---|---|---|
| 3 | 55,100 | 5.03 |
| 4 | 94,200 | 5.10 |
| 5 | 130,700 | 4.92 |
| 6 | 130,400 | 4.97 |
| 7 | 149,000 | 4.97 |
| 8 | 149,000 | 5.01 |
| 9 | 150,600 | 5.11 |
| 10 | 53,000 | 5.35 |
| 11 | 145,400 | 5.37 |
| 12 | 37,000 | 5.71 |
| 13 | 47,600 | 5.46 |
| 14 | 63,700 | 5.42 |
| 15 | 71,400 | 5.57 |
| 16 | 73,400 | 5.48 |
| 17 | 67,900 | 5.92 |
| 18 | 67,700 | 5.84 |
| 19 | 109,500 | 5.77 |
| 20 | 29,000 | 6.42 |
| 21 | 46,300 | 6.48 |
| 22 | 80,300 | 6.30 |
| 23 | 138,200 | 6.31 |
| 24 | 159,500 | 6.25 |
| 25 | 192,800 | 6.26 |

Such protein mapping data cannot readily be explained by simple genetic principles. The appearance of many supernumerary protein spots associated with a genetic defect might be explained by a post-translational event, such as excess protein phosphorylation. Such events, however, would be expected to have relatively small effects on observed protein molecular weights. Hence such an explanation appears to lack credence in this case. In fact, the information available from this study can most directly be interpreted as evidence of excess, pathological chemical crosslinking of fibroblast proteins.

Without further elaboration the foregoing will so fully illustrate my invention that others may, by applying current or future knowledge, adapt the same for use under various conditions of service.

REFERENCES CITED

Acierno, G. "Impiego della 1-acetilcarnitina nella malattia di Alzheimer (presenile e senile). Risultati preliminari" *Clin. Ter.* 105:135–145 (1983)

Amaducci, L. et al. "Phosphatidylserine in the treatment of clinically diagnosed Alzheimer's disease" *J. Neural. Transm.* 24[suppl]:287–292 (1987)

Anand, R. and Wesnes, K. A. "Cognition-enhancing effects of moclobemide, a reversible MAO inhibitor, in humans" *Adv. Neurol.* 51:261–268 (1990)

Ananth, J. et al. "Cyclandelate therapy for memory disorders" *Curr. Ther. Res.* 38:627–631 (1985)

Appenzeller, O. and Richardson, E. P. "The sympathetic chain in patients with diabetic and alcoholic polyneuropathy" *Neurology* (Minneap) 16:1205–1209 (1966)

Austin, P. R. et al. "Chitin: New facets of research" *Science* 212:749–753 (1981)

Baratti, C. M. et al. "Possible interaction between central cholinergic muscarinic and opioid peptidergic systems during memory consolidation in mice" *Behav. Neural Biol.* 40:155–169 (1984)

Bartus, R. T. and Dean, R. L. "Tetrahydroaminoacridine, 3,4-diaminopyridine and physostigmine: direct comparison of effects on memory in aged primates" *Neurobiol. Aging* 9:351–356 (1988)

Battaglia, A. et al. "Nicergoline in mild to moderate dementia. A multicenter, double-blind, placebo-controlled study" *J. Am. Geriatr. Soc.* 37:295–302 (1989)

Becker, R. E. and Giacobini, E. "Mechanisms of cholinesterase inhibition in senile dementia of the Alzheimer type: clinical, pharmacological, and therapeutic aspects" *Drug Dev. Res.* 12:163–195 (1988)

Beller, S. A. et al. "Long-term outpatient treatment of senile dementia with oral physostigmine" *J. Clin. Psychiatry* 49:400–404 (1988)

Bergmann, J.-F. et al. "Simultaneous noninvasive evaluation of gastric emptying and orocaecal transit times. Use in studying the actions of cisapride in diabetic patients" *Eur. J. Clin. Pharmacol.* 43:121–124 (1992)

Bever, C. T. et al. "Preliminary trial of 3,4-diaminopyridine in patients with multiple sclerosis" *Ann. Neurol.* 27:421–427 (1990)

Berkow, R., sr. ed. *The Merck Manual*, 16th ed. (Rahway, N.J., Merck Research Laboratories, 1992)

Bhuyan, K. C. et al. "Lipid peroxidation in cataract of the human" *Life Sci.* 38:1463–1471 (1986)

Bonavita, E. "Study of the efficacy and tolerability of L-acetyl-carnitine therapy in the senile brain" *Int. J. Clin. Pharmacol. Ther. Toxicol.* 24:511–516 (1986)

Bornstein, M. B. et al. "Clinical experience with COP-1 in multiple sclerosis" *Neurology* 38[Suppl. 2]:66–69 (1988)

Bradley, W. G. "Critical review of gangliosides and thyrotropin-releasing hormone in peripheral neuromuscular diseases" *Muscle & Nerve* 13:833–842 (1990)

Brimijoin, S. et al. "Axonal transport of dopamine-beta-hydroxylase by human sural nerves in vitro" *Science* 180:1295–1297 (1973)

Brownlee, M. et al. "Aminoguanidine prevents diabetes-induced arterial wall protein cross-linking" *Science* 232:1629–1632 (1986)

Brownlee, M. "Advanced products of nonenzymatic glycosylation and the pathogenesis of diabetic complications" in *Diabetes Mellitis Theory and Practice*, Rifkin, H. and Porte, Jr, D., eds. (New York, Elsevier, 1990) pp. 279–291

Brufani, M. et al. "A long-lasting cholinesterase inhibitor affecting neural and behavioral processes" *Pharmacol. Biochem. Behav.* 26:625–629 (1987)

Budavari, S. et al. *Merck Index*, 11th ed. (Rahway, N.J., Merck a Co., 1989)

Burkard, W. P. et al. "Pharmacological profile of moclobemide, a short-acting and reversible inhibitor of monoamine oxidase type A" *J. Pharmacol. Exp. Ther.* 248:391–399 (1989)

Carden, M. J. et al. "2,5-Hexanedione neuropathy is associated with the covalent crosslinking of neurofilament proteins" *Neurochem. Pathol.* 5:25–35 (1986)

Carpenter, S. "Proximal axonal enlargement in motor neuron disease" *Neurology* 18:841–851 (1968)

Carton, C. et al. "Synthesis and pharmacological properties of a series of 2-piperidino alkanol derivatives" *Arzneim.-Forsch/Drug Res.* 21:1992–1998 (1971)

Carter, J. L. et al. "Immunosuppression with high-dose IV cyclophosphamide and ACTH in progressive multiple sclerosis: cumulative 6-year experience in 164 patients" *Neurology* 38[Suppl. 2]:9–14 (1988).

Ceballos, I. et al. "Parkinson's disease and Alzheimer's disease: neurodegenerative disorders due to brain antioxidant system deficiency?" *Antioxidants in Therapy and Preventive Medicine*, Emerit, I., sr. ed. (New York, Plenum Press, 1990) pp. 493–498

Chan-Palay, V. "Hyperinnervation of surviving neurons of the human basal nucleus of Meynert by galanin in dementias of Alzheimer's and Parkinson's disease" *Adv. Neurol.* 51:253–255 (1990)

Chan-Palay, V. "Depression and senile dementia of the Alzheimer type: a role for moclobemide" *Psychopharmacology* 106:S137–S139 (1992)

Cho, A. K. et al. "The metabolism of tremorine" in *Biochemical and Neurophysiological correlation of centrally acting drugs*, vol. 2, trabucchi, E., sr. ed. (New York, Macmillan, 1964), pp. 75–79

Chojkier, M. et al. "Stimulation of collagen gene expression by ascorbic acid in cultured human fibroblasts" *J. Biol. Chem.* 264:16957–16962 (1989)

Clincke, G. H. et al. "The effect of R 58 735 (Sabeluzole) on memory functions in healthy elderly volunteers" *Psychopharmacology* 94:52–57 (1988)

Clineschmidt, B. V. et al. "Anticonvulsant activity of (+)-5-methyl-10,11-dihydro-5H-dibenzo[a,d]cyclohepten-5,10-imine (MK-801), a substance with potent anticonvulsant, central sympathomimetic, and apparent anxiolytic properties" *Drug Dev. Res.* 2:123–134 (1982)

Cohan, S. L. "Neurologic diseases in the elderly" in *Clinical Aspects of Aging*, third edition, Reichel, W., ed. (Baltimore, Williams & Wilkens, 1989) pp. 163–176

Cooper, J. K. "Drug treatment of Alzheimer's disease" *Arch. Intern. Med.* 151:245–249 (1991)

Crook, T. H. "Assessment of drug efficacy in age-associated memory impairment" *Adv. Neurol.* 51:211–216 (1990)

Crook, T. H. and Larrabee, G. J. "Diagnosis, assessment and treatment of age-associated memory impairment" *J. Neurol. Transm.* 33[Suppl]:1–6 (1991)

Cumin, R. et al. "Effects of the novel compound aniracetam (Ro 13-5057) upon impaired learning and memory in rodents" *Psychopharmacology* 78:104–111 (1982)

Cutler, N. R. et al. "Implications of the study population in the early evaluation of anticholinesterase inhibitors for Alzheimer's disease" *Ann. Pharmacother.* 26:1118–1122 (1992)

Daniels, B. S. and Hostetter, T. H. "Aldose reductase inhibition and glomerular abnormalities in diabetic rats" *Diabetes* 38:981–986 (1989)

Dansette, P. M. et al. "Sulfur containing compounds as antioxidants" *Antioxidants in Therapy and Preventive Medicine*, Emerit, I., sr. ed. (New York, Plenum Press, 1990) pp. 209–215

Davies, P. "Therapy for Alzheimer's disease: choosing a target" *Clin. Neuropharmacol.* 14[Suppl. 1]:S24–S33 (1991)

Davis, K. L. et al. "Physostigmine: improvement of long-term memory processes in normal humans" *Science* 201:272–274 (1978)

Delwaide, P. J. et al. "Double-blind randomized controlled study of phosphatidylserine in senile demented patients" *Acta Neurol. Scand.* 73:136–140 (1986)

Dommasch, D. "Comparative clinical trial of cyclosporine in multiple sclerosis: the pros" *Neurology* 38[Suppl. 2]:28–29 (1988)

Dunlop, A. P. and Peters, F. N. The Furans (New York, Reinhold Publishing, 1953)

Durrington, P. N. "Specific lipid lowering therapy in the management of diabetes" *Postgrad. Med. J.* 67:947–952 (1991)

Dyck, P. J. "Aldose reductase inhibitors & diabetic neuropathy" *Diabetes Forecast* (May 1989):41–44

Dysken, M. W. et al. "Milacemide: a placebo-controlled study in senile dementia of the Alzheimer type" *J. Am. Geriatr. Soc.* 40:503–506 (1992)

Egawa, M. et al. "Effects of bifemelane hydrochloride on cortical neuronal activity in cats" *Neuropharmacology* 26:379–384 (1987)

Ellison, G. W. et al. "Clinical experience with azathioprine: the pros" *Neurology* 98[Suppl]. 21:20–23 (1988)

Elsom, L. F. et al. "Identification of a major metabolite of the new hypolipidaemic agent, isopropyl 2-[4'(p- chlorobenzoyl)phenoxy]-2-methylpropionate (procetofene) in humans by gas chromatography-mass spectrometry" *J. Chromatogr.* 123:463–467 (1976)

Esterbauer, H. et al. "Separation and characterization of the aldehydic products of lipid peroxidation stimulated by ADP-Fe2$^+$ in rat liver microsomes" *Biochem. J.* 208:129–140 (1982)

Esterbauer, H. et al. "Autoxidation of human low density lipoprotein: Loss of polyunsaturated fatty acids and vitamin E and generation of aldehydes" *J. Lipid Res.* 28:495–509 (1987)

Fahn, S. "The endogenous toxin hypothesis of the etiology of Parkinson's disease and a pilot trial of high-dosage antioxidants in an attempt to slow the progression of the illness" *Ann. N Y Acad. Sci.* 570:186–196 (1989)

Fasold, H. "Chromatography of proteins" in *Chromatography: A Laboratory Handbook of Chromatographic and Electrophoretic Methods*, 3rd ed., Heftmann, E., ed. (New York, Van Nostrand Reinhold, 1975) pp. 466–526

Feeney, R. E. et al. "Carbonyl-amine reactions in protein chemistry" *Adv. Protein Chem.* 29:135–203 (1975)

Ferris, S. H. "Therapeutic strastegies in dementia disorders" *Acta Neurol. Scand. Suppl.* 129:23–26 (1990)

Fischer, P.-A. et al. "Die Wirkung intravenoser Gaben yon Memantin bei Parkinson-Kranken" *Arzneim.-Forsch/Drug Res.* 27(II):1487–1489 (1977)

Flood, J. F. et al. "Two-drug combinations of memory enhancers: effect of dose ratio upon potency and therapeutic window, in mice" *Life Sci.* 42:2145–2154 (1988)

Francis, P. T. et al. "A glycine site as therapeutic target" *Ann N Y Acad. Sci.* 640:184–188 (1991)

Franklin, S. R. et al. "Amnesia produced by intracerebroventricular injections of hemicholinium-3 in mice was prevented by pretreatment with piracetam-like compounds" *Pharmacol. Biochem. Behav.* 25:925–927 (1986)

Franson, R. C. et al. "Mechanism(s) of cytoprotective and anti-inflammatory activity of PGB$_1$ oligomers: PGBx has potent anti-phospholipase A$_2$ and anti-oxidant activity" *Prostaglandins Leukot. Essent. Fatty Acids* 43:63–70 (1991)

Fuccella, L. M. et al. "Inhibition of lipolysis by nicotinic acid and by actpimox" *Clin. Pharmacol. Ther.* 28:790–795 (1980)

Garg, A. and Grundy, S. M. "Management of dyslipidemia in NIDDM" *Diabetes Care* 13:153–169 (1990)

Garrels, J. I. "Two-dimensional gel electrophoresis and computer analysis of proteins synthesized by clonal cell lines" *J. Biol. Chem.* 254:7961–7977 (1979)

Gerster, M. "Review: antioxidant protection of the ageing macula" *Age Ageing* 20:60–69 (1991)

Ghose, A. et al. "Protection with combinations of hydroxytryptophan and some thiol compounds against whole-body gamma irradiation" *Int. J. Radiat. Biol.* 44:175–181 (1983)

Giuffra, M. E. et al. "Glutamatergic therapy of Huntington's chorea" *Clin. Neuropharmacol.* 15:148–151 (1992)

Goebel, H. H. et al. "Neuropathologic and morphometric studies in hereditary motor and sensory neuropathy type II with neurofilament accumulation" *Ital. J. Neurol. Sci.* 7:325–332 (1986)

Goldstein, M. et al. "The antiparkinsonian activity of dopamine agonists and their interaction with central dopamine receptor subtypes" *Adv. Neurol.* 53:101–106 (1990)

Goodin, D. S. "The use of immunosuppressive agents in the treatment of multiple sclerosis: a critical review" *Neurology* 41:980–985 (1991)

Goodison, K. L. et al. "Neuronal mRNA levels are maintained in Down's brains with Alzheimer pathology" *Soc. Neurosci. Abstr.* 15(pt. 2): 329 (abstract 135.6) (1989)

Greenamyre, J. T. and O'Brien, C. F. "N-methyl-D-aspartate antagonists in the treatment of Parkinson's disease" *Arch. Neurol.* 48:977–981 (1991)

Groo, D. et al. "Effects of vinpocetine in scopolamine-induced learning and memory impairments" *Drug Dev. Res.* 11:29–36 (1987)

Guthrie, R. A. "New approaches to improve diabetes control" *Am. Fam. Physician* 43:570–578 (1991)

Gutteridge, M. C. and Wilkins, S. "Copper-dependent hydroxyl radical damage to ascorbic acid. Formation of a thiobarbituric acid-reactive product" *FEBS Letters* 137:327–330 (1982)

Halliwell, B. "Drug antioxidant effects—A basis for drug selection?" *Drugs* 42:569–605 (1991)

Harman, D. "Free radical theory of aging: Effect of the amount and degree of unsaturation of dietary fat on mortality rate" *J. Gerontol.* 26:451–457 (1971)

Harris, A. L. "Paracetamol-induced acute renal failure" *BMJ* 284:825 (1982)

Harvey, A. L. and Rowan, E. G. "Effects of tacrine, aminopyridines, and physostigmine on acetylcholinesterase, acetylcholine release, and potassium currents" *Adv. Neurol.* 51:227–233 (1990)

Hayes, A. G. and Chang, T. "Determination of indeloxazine, a new anti-depressant agent, in human plasma by gas-liquid chromatography with electron-capture detection" *J. Chromatogr.* 272:176–180 (1983)

Henderson, V. W. et al. "Multicenter trial of naloxone in Alzheimer's disease" *Ann. Neurol.* 25:404–406 (1989)

Hermann, L. S. "Metformin: a review of its pharmacological properties and therapeutic use" *Diabete Metab.* 5:233–245 (1979)

Higson, F. K. et al. "Iron enhancement of ascorbate toxicity" *Free Rad. Res. Comms.* 5:107–115 (1988)

Hindmarch, I. and Subhan, Z. "A preliminary investigation of 'Albert 285' (HWA 285) on psychomotor performance, mood, and memory" *Drug Dev. Res.* 5:379–386 (1985)

Hjelle, J. J. and Petersen, D. R. "Hepatic aldehyde dehydrogenases and lipid peroxidation" *Pharmacol. Biochem. Behav.* 18:155–160 (1983)

Hock, F. J. and McGaugh, J. L. "Enhancing effects of Hoe 175 on memory in mice" *Psychopharmacology* 86:114–117 (1985)

Hock, F. J. et al. "Learning and memory processes of an ACTH$_{4-9}$ analog (ebiratide; Hoe 427) in mice and rats" *Peptides* 9:575–581 (1988)

Holmes, B. et al. "Flunarizine: a review of its pharmacodynamic and pharmacokinetic properties and therapeutic use" *Drugs* 27:6–44 (1984)

Hughes, J. T. and Brownell, B. "Pathology of peroneal muscular atrophy (Charcot-Marie-Tooth disease)" *J. Neurol. Neurosurg. Psych.* 35:648–657 (1972)

Hunter, M. I. et al. "Lipid peroxidation products and antioxidant proteins in plasma and cerebrospinal fluid from multiple sclerosis patients" *Neurochem. Res.* 10:1645–1652 (1985)

Hunter, M. I. and Mohamed, J. B. "Plasma antioxidants and lipid peroxidation products in Duchenne muscular dystrophy" *Clin. Chim. Acta* 155:123–132 (1986)

Iqbal, K. et al. "Chemical relationship of the paired helical filaments of Alzheimer's dementia to normal human neurofilaments and neurotubules" *Brain Res.* 142:321–332 (1978)

Jackson, M. J. et al. "Techniques for studying free radical damage in muscular dystrophy" *Med. Biol.* 62:135–138 (1984)

Jandacek, R. J. "Studies with sucrose polyester" *Int. J. Obes.* 8(suppl. 1):13–21 (1984)

Jellum, E. et al. "The presence of furan derivatives in patients receiving fructose-containing solutions intravenously" *Clin. Chim. Acta* 47:191–201 (1973)

Jensen, R. A. et al. "Memory, opiate receptors, and aging" *Peptides* 1[Suppl. 1]:197–201 (1980)

Jensen, L. H. et al. "Bidirectional effects of beta-carbolines and benzodiazepines on cognitive processes" *Brain Res. Bull.* 19:359–364 (1987)

Jurgens, G. et al. "Modification of human low-density lipoprotein by the lipid peroxidation product 4-hydroxynonenal" *Biochim. Biophys. Acta* 875:103–114 (1986)

Kar, N. C. and Pearson, C. M. "Catalase, superoxide dismutase, glutathione reductase and thiobarbituric acid-reactive products in normal and dystrophic human muscle" *Clin. Chim. Acta* 94:277–280 (1979)

Kikkawa, R. et al. "Effect of a new aldose reductase inhibitor, (E)-3-carboxymethyl-5-[(2EO-methyl-3-phenylpropenylidene]rhodanine (ONO-2235) on peripheral nerve disorders in streptozotocin-diabetic rats" *Diabetologia* 24:290–292 (1983)

Kikugawa, K. and Beppu, M. "Involvement of lipid oxidation products in the formation of fluorescent and cross-linked proteins" *Chem. Phys. Lipids* 44:277–296 (1987)

Kikumoto, R. et al. "Synthesis and antidepressant activity of substituted (omega-aminoalkoxy)benzene derivatives" *J. Med. Chem.* 24:145–148 (1981)

Kleinert, H. D. et al. "Discovery of a peptide-based renin inhibitor with oral bioavailability and efficacy" *Science* 257:1940–1943 (1992)

Knobler, R. L. "Systemic interferon therapy of multiple sclerosis: the pros" *Neurology* 38[Suppl. 2]:58–61 (1988)

Koller, W. C. et al. "Evaluation of ciladopa hydrochloride as a potential anti-parkinson drug" *Neuropharmacology* 25:973–979 (1986)

Krasavage, W. J. et al. "The relative neurotoxicity of methyl-n-butyl ketone, n-hexane and their metabolites" *Toxicol. Appl. Pharmacol.* 52:433–441 (1980)

Lalor, B. C. et al. "Placebo-controlled trial of the effects of guar gum and metformin on fasting blood glucose and serum lipids in obese, type 2 diabetic patients" *Diabetic Med.* 7:242–245 (1990)

Lamarche, J. et al. "Ultrastructural observations on spinal ganglion biopsy in Friedreich's ataxia: A preliminary report" *Can. J. Neurol. Sci.* 9:137–139 (1982)

Larsen, J. K. et al. "Moclobemide and clomipramine in the treatment of depression. A randomized clinical trial" *Acta Psychiatr. Scand.* 70:254–260 (1984)

Lee, S. et al. "A study of infantile motor neuron disease with neurofilament and ubiquitin immunocytochemistry" *Neuropediatrics* 20:107–111 (1989)

Lindahl, R. and Evces, S. "Comparative subcellular distribution of aldehyde dehydrogenase in rat, mouse and rabbit liver" *Biochem. Pharmacol.* 33:3383–3389 (1984)

Lovisolo, P. P. et al. "Pharmacological profile of a new antilipolytic agent: 5-methylpyrazine-2-carboxylic acid 4-oxide (acipimox). II-Antilipolytic and blood lipid lowering activity" *Pharmacol. Res. Commun.* 13:163–174 (1981)

Maccari, F. et al. "Levels of carnitines in brain and other tissues of rats of different ages: effect of acetyl-L-carnitine administration" *Exp. Gerontol.* 25:127–134 (1990)

Marks, J. B. and Skyler, J. S. "Clinical review 17. Immunotherapy of type I diabetes mellitus" *J. Clin. Endocrinol. Metab.* 72:3–9 (1991)

Martin, G. E. et al. "Pharmacologic profile of a novel potent direct-acting dopamine agonist, (+)-4-propyl-9-hydroxynaphthoxazine [(+)-PHNO]" *J. Pharmacol. Exp. Ther.* 230:569–576 (1984)

Mathews-Roth, M. M. "Photoprotection by carotenoids" *Fed. Proc.* 46:1890–1893 (1987)

Matsumoto, K. E. et al. "The identification of volatile compounds in human urine" *J. Chromatogr.* 85:31–34 (1973)

McGeer, P. L. and Rogers, J. "Anti-inflammatory agents as a therapeutic approach to Alzheimer's disease" *Neurology* 42:447–449 (1992)

Merril, C. R. et al. "Trace polypeptides in cellular extracts and human body fluids detected by two-dimensional electrophoresis and a highly sensitive silver stain" *Proc. Nat. Acad. Sci.* (U.S.A.) 76:4335–4339 (1979)

Merril, C. R. et al. "Ultrasensitive stain for proteins in polyacrylamide gels shows regional variation in cerebrospinal fluid proteins" *Science* 211:1437–1438 (1981)

Mesulam, M.-M. and Geula, C. "Shifting patterns of cortical cholinesterases in Alzheimer's disease: implications for treatment, diagnosis, and pathogenesis" *Adv. Neurol.* 51:235–240 (1990)

Micheau, J. et al. "Chronic administration of sulbutiamine improves long term memory formation in mice: possible cholinergic mediation" *Pharmacol. Biochem. Behav.* 23:195–198 (1985)

Milgram, N. W. "Use of L-deprenyl for retention of specific physiological functions" U.S. Pat. No. 5,151,449, issued Sep. 29, 1992

Mizuno, Y. et al. "Effects of indeloxazine, (+)-2-[inden-7-yloxy)-morpholine hydrochloride on cerebrospinal fluid monoamine metaboties" *Eur. Neurol.* 28:84–86 (1988)

Monk, J. P. and Todd, P. A. "Bezafibrate. A review of its pharmacodynamic and pharmacokinetic properties, and therapeutic use in hyperlipidaemia" *Drugs* 33:539–576 (1987)

Moos, W. H. et al. "Cognition activators" *Med. Res. Rev.* 8:353–391 (1988)

Moos, W. H. and Hershenson, F. M. "Potential therapeutic strategies for senile cognitive disorders" *Drug New Perspective* 2:397–409 (1989)

Moran, M. A. and Gomez-Ramos, P. "Initial stages of tangle formation in degenerating neurons of aged and Alzheimer patients" *Soc. Neurosci. Abstr.* 15(pt. 2):1039 (abstract 414.8) (1989)

Morrissey, J. H. "Silver stain for proteins in polyacrylamide gels: a modified procedure with enhanced uniform sensitivity" *Anal. Biochem.* 117:307–310 (1981)

Moss, G. et al. "Immediate restoration of central nervous system autonomic cardiopulmonary control: survival of 'lethal' cerebral hypoxia by treatment with prostaglandin $B_x$" *Surgical Forum* 39:513–516 (1978)

Muller, D. P. "Antioxidant therapy in neurological disorders" *Anti-oxidants in Therapy and Preventive Medicine,* Emerit, I., sr. ed. (New York, Plenum Press, 1990) pp. 475–484

Nagaoka, A. et al. "Inhibitory effect of idebenone (CV-2619), a novel compound, on vascular lesions in hypertensive rats" *Japan. J. Pharmacol.* 36:291–299 (1984)

Niemegeers, C. J. and Janssen, P. A. "A systemic study of the pharmacological activities of dopamine antagonists" *Life Sci.* 24:2201–2216 (1979)

Normile, H. J. and Altman, H. J. "Enhanced passive avoidance retention following posttrain serotonergic receptor antagonist administration in middle-aged and aged rats" *Neurobiol. Aging* 9:377–382 (1988)

Ochoa, J. and Mair, W. G. "The normal sural nerve in man. II. Changes in the axons and Schwann cells due to ageing" *Acta Neuropath.* (Berl.) 13:217–239 (1969)

Olivieri, N. F. et al. "Visual and auditory neurotoxicity in patients receiving subcutaneous deferoxamine infusions" *N. Engl. J. Med.* 314:969–873 (1986)

Olsson, A. G. and Lang, P. D. "Dose-response study of bezafibrate on serum lipoprotein concentrations in hyperlipoproteinaemia" *Atherosclerosis* 31:421–428 (1978a)

Olsson, A. G. and Lang, P. D. "One-year study of the effect of bezafibrate on serum lipoprotein concentrations in hyperlipoproteinaemia" *Atherosclerosis* 31:429–433 (1978b)

Ondetti, M. A. "Structural relationships of angiotensin converting-enzyme inhibitors to pharmacologic activity" *Circulation* 77[Suppl. I]:I-74–I-78 (1988)

Oppenheimer, D. R. "Diseases of the basal ganglia, cerebellum and motor neurons" in *Greenfield's Neuropathology*, Blackwood, W. and Corsellis, J. A. N., eds. (Chicago, Year Book Medical Publishers, 1976) pp. 608–651

Ortwerth, B. J. and Olesen, P. R. "Ascorbic acid-induced crosslinking of lens proteins: evidence supporting a Maillard reaction" *Biochim. Biophys. Acta* 956:10–22 (1988)

Ott, D. B. and Lachance, P. A. "Retinoic acid—a review" *Am. J. Clin. Nutr.* 32:2522–2531 (1979)

Palmer, M. H. *Urinary Incontinence* (Thorofare, N. J., Slack Publishing, 1985)

Parnetti, L. et al. "Pharmacokinetics of IV and oral acetyl-L-carnitine in a multiple dose regimen in patients with senile dementia of Alzheimer type" *Eur. J. Clin. Pharmacol.* 42:89–93 (1992)

Pepeu, G. and Spignoli, G. "Nootropic drugs and brain cholinergic mechanisms" *Prog. Neuro-Psychopharmacol. & Biol. Psychiat.* 13:S77–S88 (1989)

Pepeu, G. and Spignoli, G. "Neurochemical actions of 'nootropic drugs'" *Adv. Neurol.* 51:247–252 (1990)

Peselow, E. D. and Stanley, M. "Clinical trials of benzamides in psychiatry" in *The Benzamides: Pharmacology, Neurobiology, and Clinical Aspects*, Rotrosen, J. and Stanley, M., eds. (New York, Raven Press, 1982), pp. 163–194

Pinder, R. M. et al. "Levodopa and decarboxylase inhibitors: a review of their clinical pharmacology and use in the treatment of Parkinsonism" *Drugs* 11:329–377 (1976)

Pletscher, A. "Levodopa treatment of Parkinson's syndrome: past and future" *Adv. Neurol.* 53:469–473 (1990)

Polis, B. D. and Polis, E. "Dose dependence of $PGB_x$, a polymeric derivative of prostaglandin $B_1$, for normalization of hereditary diabetes of the mouse" *Physiol. Chem. & Physics* 11:3–8 (1979)

Polis, E. and Cope, F. W. "Dose-dependent reduction of hereditary obesity in the non-diabetic mouse by polymeric prostaglandin $PGB_x$." *Physiol. Chem. & Physics* 12:564–568 (1980)

Pongor, S. et al. "Aging of proteins: Isolation and identification of a fluorescent chromophore from the reaction of polypeptides with glucose" *Proc. Natl. Acad. Sci.* (U.S.A.) 81:2684–2688 (1984)

Pope, C. N. and Padilla, S. "Potentiation of organophosphorus-induced delayed neurotoxicity by phenylmethylsulfonyl fluoride" *J. Toxicol. Envirn. Health* 31:261–273 (1990)

Porsolt, R. D. et al. "Antiamnesic effects of magnesium pyrrolidone carboxylate (MAG 2) in three models of amnesia in the mouse" *Drug Dev. Res.* 13:57–67 (1988)

Price, P. et al. "Tiapride in Parkinson's disease" *Lancet* 2:1106 (1978)

Prineas, J. W. et al. "Giant axonal neuropathy—A generalized disorder of cytoplasmic microfilament formation" *J. Neuropathol. Exp. Neurol.* 35:458–470 (1976)

Propper, R. and Nathan, D. "Clinical removal of iron" *Ann. Rev. Med.* 33:509–519 (1982)

Rao, G. N. and Cotlier, E. "Free epsilon amino groups and 5-hydroxymethylfurfural contents in clear and cataractous human lenses" *Invest. Ophthalmol. Vis. Sci.* 27:98–102 (1986)

Reed, R. L. and Mooradian, A. D. "Treatment of diabetes in the elderly" *Am. Fam. Physician* 44:915–924 (1991)

Reisberg, B. et al. "Effects of naloxone in senile dementia: a double-blind trial" *N. Engl. J. Med.* 308:722–722 (1983)

Rinne, U. K. "Lisuride, a dopamine agonist in the treatment of early Parkinson's disease" *Neurology* 39:336–339 (1989)

Rinne, U. K. "New strategies in the treatment of early Parkinson's disease" *Acta. Neurol Scand.* 84[Suppl. 136]:95–98 (1991)

Robin, D. W. "Pergolide in the treatment of Parkinson's disease" *Am. J. Med. Sci.* 301:277–280 (1991)

Roufs, J. B. "L-Threonine as a symptomatic treatment for amyotrophic lateral sclerosis (ALS)" *Med. Hypotheses* 34:20–23 (1991)

Rush, D. K. "Reversal of scopolamine-induced amnesia of passive avoidance by pre- and post-training naloxone" *Psychopharmacology* 89:296–300 (1986)

Saletu, B. et al. "Psychophysiological research in psychiatry and neuropsychopharmacology. II. The investigation of antihypoxidotic/nootropic drugs (tenilsetam and co-dergocrine-mesylate) in elderlies with the Viennese Psychophysiological Test-System (VPTS)" *Meth. Find. Exp. Clin. Pharmacol.* 11:43–55 (1989)

Sanchez-Ramos, J. R. "Banisterine and Parkinson's disease" *Clin. Neuropharmocol.* 14:391–402 (1991)

Schauenstein, E. "Autoxidation of polyunsaturated esters in water: Chemical structure and biological activity of the products" *J. Lipid Res.* 8:417–428 (1967)

Schleuning, A. J. "Management of the patient with tinnitus" *Med. Clin. North Am.* 75:1225–1237 (1991)

Schmidt, W. J. et al. "Excitatory amino acids and Parkinson's disease" *Trends Neurosci.* 13:46–47 (1990)

Schwendemann, G. "Diagnosis of juvenile ceroid-lipofuscinosis by electron microscopy of lymphocytes and of rectal, skin and sural nerve biopsy tissues" in *Ceroid-Lipofuscinosis (Batten Disease)*, Armstrong, D., sr. ed. (New York, Elsevier Biomedical Press, 1982) pp. 117–136

Selkoe, D. J. et al. "Alzheimer's disease: insolubility of partially purified paired helical filaments in sodium dodecyl sulfate and urea" *Science* 215:1243–1245 (1982)

Sellin, L. C. and Laakso, P. S. "Antagonism of ethanol-induced depressant effects by 4-aminopyridine in the central nervous system of the rat" *Neuropharmacology* 26:385–390 (1987)

Shapiro, H. K. et al. "Metabolic screening of Charcot-Marie-Tooth disease patients by gas chromatography/mass spectrometry" *Muscle & Nerve* 9(suppl. 5S):128 (1986)

Shapiro, H. K. and Kahn, G. C. "Metabolic screening studies on Charcot-Marie-Tooth disease" in *Charcot-Marie-Tooth Disorders: Pathophysiology, Molecular Genetics, and Therapy*, Lovelace, R. E. and Shapiro, H. K., eds. (New York, Wiley-Liss, 1990) pp. 365–371

Shaw, G. K. et al. "Tiapride in the long-term management of alcoholics of anxious or depressive temperament" *Brit. J. Psychiatry* 150:164–168 (1987)

Shimasaki, H. et al. "Formation of age pigment-like fluorescent substances during peroxidation of lipids in model membranes" *Biochim. Biophys. Acta* 792:123–129 (1984)

Shimizu, M. "Current clinical trials of cognitive enhancers in Japan" *Alzheimer's Dis. Assoc. Disord.* 5[Suppl. 1]:S13–S24 (1991)

Shutske, G. M. et al. "(±)-9-amino-1,2,3,4-tetrahydroacridin-1-ol. A potential Alzheimer's disease therapeutic of low toxicity" *J. Med. Chem.* 31:1278–1279 (1988)

Sidenius, P. and Jakobsen, J. "Reversibility and preventability of the decrease in slow axonal transport velocity in experimental diabetes" *Diabetes* 31:689–693 (1982)

Sima, A. A. et al. "Regeneration and repair of myelinated fibers in sural-nerve biopsy specimens from patients with diabetic neuropathy treated with sorbinil" *N. Engl. J. Med.* 319:548–555 (1988)

Sitaram, N. et al. "Choline: selective enhancement of serial learning and encoding of low imagery words in man" *Life Sci.* 22:1555–1560 (1978a)

Sitaram, N. et al. "Human serial learning: enhancement with arecholine and choline and impairment with scopolamine" *Science* 201:274–276 (1978b)

Skyler, J. S. "Strategies in diabetes mellitus—start of a new era" *Postgrad. Med.* 89:45–56 (1991)

Slight, S. H. et al. "Glycation of lens proteins by the oxidation products of ascorbic acid" *Biochim. Biophys. Acta* 1038:367–374 (1990)

Smilkstein, M. J. et al. "Efficacy of oral N-acetylcysteine in the treatment of acetaminophen overdose" *N. Engl. J. Med.* 319:1557–1562 (1988)

Spignoli, G. and Pepeu, G. "Interactions between oxiracetam, aniracetam and scopolamine on behavior and brain acetylcholine" *Pharmacol. Biochem. Behav.* 27:491–495 (1987)

Spignoli, G. et al. "Effect of pyroglutamic acid stereoisomers on ECS and scopolamine-induced memory disruption and brain acetylcholine levels in the rat" *Pharmacol. Res. Commun.* 19:901–912 (1987)

Sporn, M. B. et al. "13-cis-Retinoic acid: inhibition of bladder carcinogenesis in the rat" *Science* 195:487–489 (1977)

Steinbrecher, U. P. "Oxidation of human low density lipoprotein results in derivatization of lysine residues of apolipoprotein B by lipid peroxide decomposition products" *J. Biol. Chem.* 262:3603–3608 (1987)

Stern, Y. et al. "Long-term administration of oral physostigmine in Alzheimer's disease" *Neurology* 38:1837–1841 (1988)

Stern, M. P. and Haffner, S. M. "Dyslipidemia in type II diabetes—implications for therapeutic intervention" *Diabetes Care* 14:1144–1159 (1991)

Stojek, A. et al. "Physostigmine in alcohol withdrawal: a new clinical approach" *J. Clin. Psychiatr.* 47:530 (1986)

Summers, W. K. et al. "Oral tetrahydroaminoacridine in long-term treatment of senile dementia, Alzheimer type" *New Engl. J. Med.* 315:1242–1245 (1986)

Sweeney, J. E. et al. "Effects of different doses of galanthamine, a long-acting acetylcholinesterase inhibitor, on memory in mice" *Psychopharmacology* 102:191–200 (1990)

Swingle, K. F. et al. "Anti-inflammatory activity of antioxidants" in *Anti-Inflammatory and Anti-Rheumatic Drugs. Volume III. Anti-Rheumatic Drugs, Experimental Agents, and Clinical Aspects of Drug Use*, Rainsford, K. D., ed. (Boca Raton, Fla., CRC Press, 1985), pp. 105–126

Tachikawa, S. et al. "Pharmacological and biochemical studies on a new compound, 2-(7-indenyloxymethyl) morpholine hydrochloride (YM-08054-1), and its derivatives with potential antidepressant properties" *Arch. Int. Pharmacodyn.* 238:81–95 (1979)

Tan, N. T. et al. "Neuropathology of the cortical lesions of the Parkinsonian-dementia (PD) complex of Guam" *Clin. Exp. Neurol.* 17:227–234 (1981)

Tang, X.-C. et al. "Effect of huperzine A, a new cholinesterase inhibitor, on the central cholinergic system of the rat" *J. Neurosci. Res.* 24:276–285 (1989)

Tariot, P. N. et al. "Multiple-dose arecoline infusions in Alzheimer's disease" *Arch. Gen. Psychiatry* 45:901–905 (1988)

Tellez-Nagel, I. et al. "Studies on brain biopsies of patients with Huntington's chorea" *J. Neuropathol. Exp. Neurol.* 33:308–332 (1974)

Tempesta, E. et al. "L-Acetylcarnitine in depressed elderly subjects. A cross-over study vs placebo" *Drugs Exptl. Clin. Res.* 13:417–423 (1987)

Thal, L. J. and Altman Fuld, P. "Memory enhancement with oral physostigmine in Alzheimer's disease" *N. Engl. J. Med.* 308:720 (1983)

Thal, L. J. et al. "Chronic oral physostigmine without lecithin improves memory in Alzheimer's disease" *J. Am. Geriatr. Soc.* 37:42–48 (1989)

Tobe, A. et al. "Pharmacological evaluation of 2-(4-methylaminobutoxy)diphenylmethane hydrochloride (MCI-2016), a new psychotropic drug with antidepressant activity" *Arzneim.-Forsch./Drug Res.* 31:1278–1285 (1981)

Toivonen, L. K. et al. "Pirmenol in the long-term treatment of chronic ventricular arrhythmias: a placebo-controlled study" *J. Cardiovasc. Pharmacol.* 8:156–160 (1986)

Tomlinson, D. R. and Mayer, J. H. "Defects of axonal transport in diabetes mellitus—A possible contribution to the aetiology of diabetic neuropathy" *J. Auton. Pharmac.* 4:59–72 (1984)

Totaro, E. A. et al. "Morphological evaluation of the lipofuscinolytic effect of acetylhomocysteine thiolactone" *Arch. Gerontol. Geriatr.* 4:67–72 (1985)

Travis, J. "Can 'hair cells' unlock deafness?" *Science* 257:1344–1345 (1992)

Tsuchida, M. et al. "Lipofuscin and lipofuscin-like substances" *Chem. Phys. Lipids* 44:297–325 (1987)

Umeno, Y. et al. "Gas chromatographic-mass fragmentographic determination of homopantothenic acid in plasma" *J. Chromatogr.* 226:333–339 (1981)

van Gilst, W. H. et al. "Reduction of reperfusion arrhythmias in the ischemic isolated rat heart by angiotensin converting enzyme inhibitors: a comparison of captopril, enalapril, and HOE 498" *J. Cardiovasc. Pharmacol.* 8:722–728 (1986)

van Weerden, T. W. et al. "Variability in nerve biopsy findings in a kinship with dominantly inherited Charcot-Marie-Tooth disease" *Muscle & Nerve* 5:185–196 (1982)

Villardita, C. et al. "Clinical and neuropsychological study with oxiracetam versus placebo in patients with mild to moderate dementia" *J. Neural. Transm.* 24[Suppl]:293–298 (1987)

Weglicki, W. B. et al. "Mechanisms of cardiovascular drugs as anti-oxidants" *J. Mol. Cell. Cardiol.* 22:1199–1208 (1990)

Westlin, W. and Mullane, K. "Does captopril attenuate reperfusion-induced myocardial dysfunction by scavenging free radicals?" *Circulation* 77[Suppl. I]:I-30–I-39 (1988)

Whitehouse, P. J. "Treatment of Alzheimer disease" *Alzheimer Dis. Assoc. Disord.* 5[Suppl. 1]:S32–S36 (1991)

Wiesel, F.-A. et al. "Pharmacokinetics of oral moclobemide in healthy human subjects and effects on MAO-activity in platelets and excretion of urine monoamine metabolites" *Eur. J. Clin. Pharmacol.* 28:89–95 (1985)

Williams, R. T. *Detoxication Mechanisms: The Metabolism and Detoxication of Drugs, Toxic Substances and Other Organic Compounds* (New York, John Wiley & Sons, 1959)

Williams, L. L. et al. "Review: effects of a dietary linoleic (omega-6) fatty acid and vitamin E supplementation on type I CMT serum fatty acids and physical performance" *Neurology and Neurobiology* 53:403–407 (1990)

Wisniewski, H. M. et al. "Neurofibrillary pathology" *J. Neuropath. Exp. Neurol.* 29:163–176 (1970)

Wisniewski, H. M. et al. "Neurofibrillary and synaptic pathology in the aged brain" in *Aging and Cell Structure*, volume 1, Johnson, Jr., J. E., ed. (New York, Plenum Press, 1982) pp. 105–142

Woggon, B. et al. "Der Einfluss von Diagnose, Klinik und Geschlecht auf die Wirkung von Bromperidol" *Int. Pharmacopsychiat.* 14:213–227 (1979)

Wong, S. F. et al. "The role of superoxide and hydroxyl radicals in the degradation of hyaluronic acid induced by metal ions and by ascorbic acid" *J. Inorganic Biochemistry* 14:127–134 (1981)

Woodley, M. and Whelan, A., ads. *Manual of Medical Therapeutics*, 27th ed. (Boston, Little, Brown, 1992)

Woodruff, G. N. et al. "The interaction between MK-801 and receptors for N-methyl-D-aspartate: functional consequences" *Neuropharmacology* 26:903–909 (1987)

Wulfert, E. et al. "Antilipidemic drugs. Part 6; L. F. 178 in man. A preliminary note on a multicenter investigation bearing on 393 subjects with pure or mixed forms of hyperlipidemia" *Arzneim.-Forsch./Drug Res.* 26:906–909 (1976)

Wurtman, R. J. et al. "Choline metabolism in cholinergic neurons: implications for the pathogenesis of neurodegenerative diseases" *Adv. Neurol.* 51:117–125 (1990)

Yalpani, M. *Polysaccharides: Syntheses, Modifications and Structure-Property Relations* (New York, Elsevier, 1988)

Yamamura, Y. et al. "Morphological studies on human and experimental diabetic neuropathy" in *Diabetic Neuropathy*, Goto, Y, sr. ed. (Princeton, Excerpta Medica, 1982) pp. 80–85

Yancey, M. et al. "Quantitative alterations in the metabolism of carbonyl compounds due to diet-induced lipid peroxidation in rats" *J. Chromatogr.* 382:47–56 (1986)

Ylikoski, J. et al. "Vestibular nerve in Meniere's disease" *Arch. Otolaryngol.* 106:477–483 (1980)

Yoshimura, N. "Topography of Pick body distribution in Pick's disease: a contribution to understanding the relationship between Pick's and Alzeheimer's diseases" *Clin. Neuropath.* 8:1–6 (1989)

Youdim, M. B. "Platelet monoamine oxidase B: use and misuse" *Experientia* 44:137–141 (1988)

Youdim, M. B. "Inhibitors of dopamine inactivating systems as anti-parkinson drugs" *Adv. Neurol.* 53:483–488 (1990)

Zanotti, A. et al. "Reversal of scopolamine-induced amnesia by phosphatidylserine in rats" *Psychopharmacology* 90:274–275 (1986)

Zimmermann, R. et al. "The effect of bezafibrate on the fibrinolytic enzyme system and the drug interaction with racemic phenprocoumon" *Atherosclerosis* 29:477–485 (1978)

Zlatkis, A. and Liebich, H. M. "Profile of volatile metabolites in human urine" *Clin. Chem.* 17:592–594 (1971)

I claim:

1. A composition for treating a mammal suffering from a neurological disease characterized in part by covalent bond crosslinking between the mammal's nerve cells, other cellular structures and their intracellular and extracellular components with disease-induced carbonyl-containing aliphatic or aromatic hydrocarbons present in the mammal, said composition comprising a therapeutically effective amount of a dosage in the range of one gram/day to forty grams/day of at least one carbonyl trapping agent to compete with and covalently bind to said disease-induced carbonyl-containing aliphatic or aromatic hydrocarbons, said carbonyl trapping agent being a compound of the formula

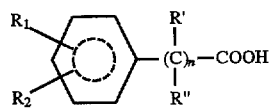

wherein $R_1$ is selected from the group consisting of $-NH_2$; -aminoalkyl having 1–10 carbons; $-NHC(=NH)NH_2$; $-(CH_2)_n NHC(=NH)NH_2$ wherein n is 1–10; $C(=NH)NH_2$; $-(CH_2)_n-CH=NH(=NH)NH_2$ wherein n is 1–10; $-NHC(=NH)NHNH_2$; $-(CH_2)_n NHC(=NH)NHNH_2$ wherein n is 1–10; $-(CH_2)_n-CH=NC(=NH)NHNH_2$ wherein n is 1–10; $-NHNHC(=NH)NH_2$; $-(CH_2)_n-NHNHC(=NH)NH_2$ wherein n is 1–10; and $-(CH_2)_n-CH=N-NHC(=NH)NH_2$ wherein n is 1–10;

$R_2$ is selected from the group consisting of H; $-OH$; $-O-CH_3$; $-OR'$ wherein R' is alkyl of 2–10 carbons; aminoalkyl wherein the alkyl group is 1–10 carbons; $-SO_3H$; $-CH_3$; and $-(CH_2)_n CH_3$ wherein n is 1–10; and R' and R" are H, OH or $CH_3$; and n is 0 or 1.

2. A composition effective in treating a human suffering from Parkinson's disease, the composition comprising an effective amount of at least one of the carbonyl trapping primary amine agents of claim 1 in combination with an effective amount of at least one of the following medicaments: (a) levodopa, levodopa with carbidopa; (b) amantadine (1-amino-adamantane); (c) a dopamine agonist; (d) an anticholinergic medication; (e) an antihistamine; (f) a tricyclic antidepressant; (g) a serotonin reuptake inhibitor antidepressant; (h) a beta blocker co-agent; (i) selegiline, selegiline with tocopherol; (j) D-cycloserine, D-cycloserine with a cholinesterase inhibitor; (k) a neurotransmission enhancer co-agent; (l) a peripheral decarboxylase inhibitor; (m) a N-methyl-D-aspartate glutamate receptor antagonist; (n) tacrine, tacrine with phosphatidylcholine; (o) lazabemide; (p) tiapride; and (q) at least one antioxidant, wherein the composition is adapted to administer both the carbonyl trapping primary amine and the medicament via the same route.

3. The composition of claim 2 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

4. A composition effective in treating a human suffering from Alzheimer's disease, the composition comprising an effective amount of at least one of the carbonyl trapping primary amine agents of claim 1 in combination with an effective amount of at least one of the following medicaments: (a) a vasodilator or other nootropic direct brain metabolic enhancer co-agent; (b) a neuro-transmission enhancer co-agent; (c) ifenprodil; (d) tiapride; (e) a psychotherapeutic co-agent; (f) an acetylcholinesterase inhibitor; (g) a calcium channel blocker co-agent; (h) a biogenic amine and a co-agent related thereto; (i) an antirage co-agent; (j) a benzodiazepine tranquilizer; (k) an angiotensin-converting enzyme inhibitor; (l) a co-agent which enhances acetylcholine synthesis, storage or release; (m) an acetylcholine postsynaptic receptor agonist; (n) ganglioside $GM_1$; (o) mixed cow brain gangliosides; (p) a specific monoamine oxidase-A inhibitor; (q) an N-methyl-D-aspartate glutamate receptor antagonist; (r) a nonsteroidal anti-inflammatory co-agent; (s) selegiline; (t) thiamine; (u) sulbutiamine; (v) anfacine; (w) an antioxidant co-agent; (x) a specific monoamine oxidase-B inhibitor; (y) linopirdine; (z) D-cycloserine; and (a') a serotonergic receptor antagonist, wherein the composition is adapted to administer both the carbonyl trapping primary amine and the medicament via the same route.

5. The composition of claim 4 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

6. A composition effective in treating a human suffering from diabetes, the composition comprising an effective amount of at least one of the carbonyl trapping primary amine agents of claim 1 in combination with an effective amount of at least one of the following medicaments: (a) insulin derivatives and compositions; (b) sulfanilamide derivative hypoglycemic agents; (c) angiotensin-converting enzyme inhibitors; (d) anti-hyperlipidemia co-agents; (e) antioxidants; (f) immunosuppressive drugs; (g) co-agents which decrease blood platelet aggregation; (h) co-agents which decrease blood viscosity; (i) mixed cow brain gangliosides; (j) analgesic co-agents for treatment of chronic pain; (k) co-agents for treatment of diabetes-related nephrotic syndrome; and (l) aldose reductase inhibitors wherein the composition is adapted to administer both the carbonyl trapping primary amine and the medicament via the same route.

7. The composition of claim 6 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

8. A composition effective in treating a human suffering from aging symptomology, the composition comprising an effective amount of at least one of the carbonyl trapping primary amine agents of claim 1 in combination with an effective amount of at least one of the following medicaments: (a) monoamine oxidase B inhibitors; (b) acetylcholinesterase inhibitors; (c) angiotensin-converting enzyme inhibitors; (d) N-methyl-D-aspartate glutamate receptor antagonists; (e) antioxidant combinations; (f) nootropic drugs; (g) postsynaptic receptor agonists; (h) biogenic amines and co-agents related thereto; (i) anfacine; (j) acetylcholine synthesis, storage or release co-agents; (k) prostaglandin $B_1$ oligomers (also known as polymeric 15-keto prostaglandin B or $PGB_x$); (l) acetylhomocysteine thiolactone; (m) ganglioside $GM_1$; (n) sulbutiamine; and (o) serotonergic receptor antagonists, wherein the composition is adapted to administer both the carbonyl trapping primary amine and the medicament via the same route.

9. The composition of claim 8 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

10. A composition effective in treating a human suffering from tinnitus, the composition comprising an effective amount of at least one of the carbonyl trapping primary amine agents of claim 1 in combination with at least one of the following medicaments: (a) antidepressants or antianxiety medications; (b) anti-convulsants; (c) lidocaine; (d) tocainide; (e) flecinide; (f) nicotinamide; (g) aminooxyacetic acid; (h) praxilene; (i) aniracetam; (j) piracetam; (k) 13-cis-retinoic acid; and (l) 13-trans-retinoic acid, wherein the composition is adapted to administer both the carbonyl trapping primary amine and the medicament via the same route.

11. The composition of claim 10 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

12. A composition effective in treating a human suffering from multiple sclerosis, the composition comprising an effective amount of at least one of the carbonyl trapping primary amine agents of claim 1 in combination with an effective amount of at least one of the following medicaments: (a) azathioprine; (b) copolymer-1; (c) cyclosporine; (d) interferons; (e) corticosteroids; (f) cyclophos-phamide; (g) 4-aminopyridine; (h) baclofen; and (i) 3,4-diaminopyridine, wherein the composition is adapted to administer both the carbonyl trapping primary amine and the medicament via the same route.

13. The composition of claim 12 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

14. A composition effective in treating a human suffering from amyotrophic lateral sclerosis, the composition comprising an effective amount of at least one of the carbonyl trapping primary amine agents of claim 1 in combination with at least one of the following medicaments: (a) mixed cow brain gangliosides; (b) a thyrotropin releasing factor; (c) serine; (d) L-threonine; (e) glycine; (f) an N-methyl-D-aspartate glutamate receptor antagonist, wherein the composition is adapted to administer both the carbonyl trapping primary amine and the medicament via the same route.

15. The composition of claim 14 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

16. A composition effective in treating a human suffering from Huntington's disease, the composition comprising an effective amount of at least one of the carbonyl trapping primary amine agents of claim 1 in combination with an effective amount of at least one of the following medicaments: (a) an N-methyl-D-aspartate glutamate receptor antagonist; (b) a co-agent which enhances acetylcholine synthesis, storage or release; and (c) a postsynaptic receptor agonist, wherein the composition is adapted to administer both the carbonyl trapping primary amine and the medicament via the same route.

17. The composition of claim 16 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

18. A composition effective in treating a human suffering from olivopontocerebellar atrophy, the composition comprising an effective amount of at least one of the carbonyl trapping primary amine agents of claim 1 in combination with an effective amount of at least one of the following medicaments: an N-methyl-D-aspartate glutamate receptor antagonist, wherein the composition is adapted to administer both the carbonyl trapping primary amine and the medicament via the same route.

19. The composition of claim 18 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

20. A composition effective in treating a human suffering from alcoholic polyneuropathy, the composition comprising an effective amount of at least one of the carbonyl trapping primary amine agents of claim 1 in combination with an effective amount of at least one medicament selected from the group consisting of (a) mixed cow brain gangliosides; (b) tiapride; (c) physostigmine optionally with phosphatidylcholine; (d) piracetam; and (e) cyclandelate, wherein the composition is adapted to administer both the carbonyl trapping primary amine and the medicament via the same route.

21. The composition of claim 20 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

22. A composition effective in treating a human suffering from a hereditary motor and sensory neuropathy, the composition comprising an effective amount of at least one of the carbonyl trapping primary amine agents of claim 1 in combination with an effective amount of selected from the group consisting of: (a) mixed cow brain gangliosides; and (b) 3,4-diaminopyridine, wherein the composition is adapted to administer both the carbonyl trapping primary amine and the medicament via the same route.

23. The composition of claim 22 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

24. A composition effective in treating a human suffering from urinary incontinence resulting from Alzheimer's senile dementia, demyelinating diseases, multiple sclerosis, peripheral nerve lesions, diabetes mellitus and alcoholic polyneuropathy, the composition comprising an effective amount of at least one of the carbonyl trapping primary amine agents of claim 1 in combination with an effective amount of at least one of the following medicaments: (a) cholinergics; (b) anti-cholinergics; (c) alpha-adrenergics; (d) tricyclic co-agents; (e) flavoxate; (f) beta-adrenergic blockers; and (g) vasopressin analogues, wherein the composition is adapted to administer both the carbonyl trapping primary amine and the medicament via the same route.

25. The composition of claim 24 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

26. A composition effective in treating a human suffering from gastroesophageal reflux disease, hypoperistalsis and/or delayed gastric emptying, the composition comprising an effective amount of at least one of the carbonyl trapping primary amine agents of claim 1 in combination with an effective amount of at least one of the following medications: (a) metoclopramide; (b) cisapride; (c) famotidine; (d) cimetidine; (e) ranitidine; (f) omeprazole; and (g) galanthamine, wherein the composition is adapted to administer both the carbonyl trapping primary amine and the medicament via the same route.

27. The composition of claim 26 additionally comprising an effective amount of at least one co-agent selected from the group consisting of non-absorbable polyamine polymers, polyamine-related polymers, antioxidants, suspending reagents, vitamins, co-agents which facilitate glutathione biological activity, hormones, chemical conjugating agents which facilitate kidney drug elimination, metabolites at risk of depletion, sulfhydryl containing agents and derivatives thereof, and free radical trapping compounds.

28. A composition effective in treating a human suffering from atherosclerosis, the composition comprising an effective amount of at least one of the carbonyl trapping primary amine agents of claim 1 in combination with at least one of the following medicaments: (a) an angiotensin-converting enzyme inhibitor free radical scavenging co-agent possessing sulfhydryl groups; (b) a fibric acid derivative antihyperlipidemia co-agent; (c) metformin; (d) nicotinic acid; (e) a natural hydroscopic non-digestable edible plant carbohydrate polymer; (f) 3-hydroxy-3-methyl-glutaryl-CoA reductase inhibitors; (g) acipimox; (h) a bile acid sequestant;

(i) at least one antioxidant; (j) an anti-hypertensive agent; (k) a drug for use in treatment of ischemic heart disease; and (l) a ventricular antiarrhythmic drug, wherein the composition is adapted to administer both the carbonyl trapping primary amine and the medicament via the same route.

29. The composition of claim 28 additionally comprising an effective amount of at least one co-agent selected from the group consisting of non-absorbable polyamine polymers, polyamine polymers or non-absorbable polyamine-related polymers, antioxidants, suspending reagents, vitamins, co-agents which facilitate glutathione biological activity, hormones, chemical conjugating agents which facilitate kidney drug elimination, metabolites at risk of depletion, sulf-hydryl containing agents and derivatives thereof, and free radical trapping compounds.

* * * * *